(12) United States Patent
Floudas et al.

(10) Patent No.: US 6,832,162 B2
(45) Date of Patent: Dec. 14, 2004

(54) METHODS OF AB INITIO PREDICTION OF α HELICES, β SHEETS, AND POLYPEPTIDE TERTIARY STRUCTURES

(75) Inventors: Christodoulos A. Floudas, Princeton, NJ (US); John L. Klepeis, New Fairfield, CT (US)

(73) Assignee: The Trustees of Princeton University, Princeton, NJ (US)

( * ) Notice: Subject to any disclaimer, the term of this patent is extended or adjusted under 35 U.S.C. 154(b) by 145 days.

(21) Appl. No.: 09/788,006

(22) Filed: Feb. 16, 2001

(65) Prior Publication Data

US 2003/0036093 A1 Feb. 20, 2003

(51) Int. Cl.[7] .......................... G06F 17/00; G06F 17/30
(52) U.S. Cl. .......................................... 702/19; 702/27
(58) Field of Search ..................................... 702/19, 27

(56) References Cited

U.S. PATENT DOCUMENTS 5,878,373 A * 3/1999 Cohen et al. ................. 702/22

OTHER PUBLICATIONS

Zhou et al. Biochemistry, 32, 6190–6197, 1993.*
Parodi et al. Computational Chemistry, vol. 10, 527–535, 1994.*
Sun et al. Protein Science, 9, 750–754, 2000.*
Adjiman, C. et al., "Rigorous convex underestimators for general twice–differentiable problems", *J. Glob. Opt.*, 1996, vol. 9, pp. 23–40.
Adjiman, C. et al., "A global optimization method, αBB, for general twice–differentiable constrained NLPs. I. Theoretical advances", *Computers Chem. Engng.*, 1998, vol. 22, No. 9, pp. 1137–1158.
Adjiman, C. et al., "A global optimization method, αBB, for general twice–differentiable constrained NLPs. II. Implementation and computational results", *Computers Chem. Engng.*, 1998, vol. 22, pp. 1159–1179.
Adjiman, C. et al., "A global optimization method, αBB, for process design", *Computers Chem Engng.*, 1996, vol. 20, Suppl., pp. S419–S424.
Adjiman, C. et al., "Global optimization of MINLP problems in process synthesis and design", *Computers Chem. Engng.*, 1997, vol. 21, Suppl., pp. S445–S450.
Altschul, S. et al., "Gapped BLAST and PSI–BLAST: a new generation of protein database search programs", *Nucleic Acids Research*, 1997, vol. 25, No. 17, pp. 3389–3402.
Androulakis, I. et al., "αBB: A global optimization method for general constrained nonconvex problems", *J. Glob. Opt.*, 1995, vol. 7, pp. 337–363.
Androulakis, I. et al., "Prediction of oligopeptide conformations via deterministic global optimization", *J. Glob. Opt.*, 1997, vol. 11, No. 1, pp. 1–34.
Anfinsen,, C. et al., "Experimental and theoretical aspects of protein folding", *Advances in Protein Chemistry*, 1975, vol. 29, pp. 205–301.
Anfinsen, C. et al., "Principles that govern the folding of protein chains", *Science*, 1973, vol. 181, No. 4096, pp. 223–230.
Baldwin, R. et al., "Is protein folding hierarchic? I. Local structure and peptide folding", *TIBS*, 1999, vol. 24, pp. 26–33.

(List continued on next page.)

Primary Examiner—Michael Borin
(74) Attorney, Agent, or Firm—Woodcock Washburn LLP

(57) ABSTRACT

The present invention provides a novel four stage ab initio approach for predicting the tertiary structure of polypeptides. The methods of the invention combine the classical and modern views of protein folding, while using free energy calculations and integer linear optimization to predict helical and β-sheet structures. Derivation of restraints, detailed atomistic modeling, and a deterministic global optimization method, αBB, coupled with torsion angle dynamics, form the basis for the final tertiary structure prediction. The performance of the methods of the invention is illustrated using several different polypeptides.

10 Claims, 29 Drawing Sheets

OTHER PUBLICATIONS

Baldwin, R. et al., "Is protein folding hierarchic? II. Folding intermediates and transition states", *TIBS*, 1999, vol. 24, pp. 77–73.

Baldwin, R. et al., "α–Helix formation by peptides of defined sequence", *Biophys. Chem.*, 1995, vol. 55, pp. 127–135.

Bryant, Z. et al., "Mechanical unfolding of a α–Hairpin using molecular dynamics", *Biophys. J.*, 2000, vol. 78, pp. 584–589.

Burgess, A. et al., "Assessment of some problems associated with prediction of the three–dimensional structure of protein from its amino–acid sequence", *PNAS, USA*, Apr. 1975, vol. 72, No. 4, pp. 1221–1225.

Caves, L. et al., "Locally accessible conformations of proteins: Multiple molecular dynamics simulations of crambin", *Protein Science*, 1998, vol. 7, pp. 649–666.

Cornette, J. et al., "Hydrophobicity scales and computational techniques for detecting amphipathic structures in proteins", *J. Mol. Biol.*, 1987, vol. 195, pp. 659–685.

Creighton, T. et al., "Protein folding", *Biochem. J.*, 1990, vol. 270, No. 1, pp. 1–16.

Creighton, T. et al., "Kinetic role of a meta–stable native–like two–disulphide species in the folding transition of bovine pancreatic trypsin inhibitor", *J. Mol. Biol.*, 1984, vol. 179, pp. 497–526.

Creighton, T. et al., "Immunochemical analysis of the conformational properties of intermediates trapped in the folding and unfolding of bovine pancreatic trypsin inhibitor", *J. Mol. Biol.*, 1978, vol. 123, pp. 129–147.

Daggett, V. et al., "Combined molecular dynamics and Φ–Value analysis of structure–reactivity relationships in the transition state and unfolding pathway of barnase: Structural basis of hammond and anti–hammond effects", *J. Am. Chem. Soc.*, 1998, vol. 120, pp. 12740–12754.

Deisenhofer, J. et al., "Crystallographic refinement of the structure of bovine pancreatic trypsin at 1·5 Å resolution", *Acta Cryst.*, 1975, Section B31, pp. 238–250.

Dill, K. et al., "Protein structure and energy landscape dependence on sequence using a continuous energy function", *J. Computational Biology*, 1997, vol. 4, No. 3, pp. 227–239.

Dill, K. et al., "Polymer principles and protein folding", *Protein Science*, 1999, vol. 8, pp. 1166–1180.

Dinner, A. et al., "Understanding β–haripin formation", *PNAS USA*, Aug. 1999, 96, 9068–9073.

Duan, Y. et al., "Pathways to a protein folding intermediate observed in a 1–microsecond simulation in aqueous solution", *Science*, 1998, 282, 740–744.

Flory, P.J., "Foundations of rotational isometric state theory and general methods for generating configurational averages", *Macromolecules*, 1974, vol. 7, No. 3, pp. 381–392.

Floudas, C., "Large–Scale Optimization with Applications, Part II: Optimal Design and Control", vol. 93, pp. 129–184, in IMA Volumes in Mathematics and its Applications, Springer–Verlag, (Biegler et al., eds.), 1997.

Gallagher, T. et al., "Two crystal structures of the B1 immunoglobulin–binding domain of streptococcal protein G and comparison with NMR", *Biochem.*, 1994, vol. 33, pp. 4721–4729.

Garnier, J. et al., "Analysis of the accuracy and implications of simple methods for predicting the secondary structure of globular proteins", *J. Mol. Biol.*, 1978, vol. 120, pp. 97–120.

Gilson, M. et al., "Calculating the electrostatic potential of molecules in solution: Method and error assessment", *J. Comp. Chem.*, 1987, vol. 9, No. 4, pp. 327–335.

Gilson, M. et al., "Calculating the total electrostatic energy of a macromolecular system: Solvation energies, binding energies, and conformational analysis", *Proteins*, 1988, vol. 4, pp. 7–18.

Gō, N. et al., "Analysis of the contribution of internal vibrations to the statistical weights of equilibrium conformations of macromolecules", *J. Chem. Phys.*, 1969, vol. 51, No. 11, pp. 4751–4767.

Gō, N. et al., "On the use of classical statistical mechanics in the treatment of polymer chain conformation", *Macromolecules*, 1976, vol. 9, No. 4, pp. 535–542.

Gronenborn, A. et al., "a novel highly stable fold of the immunoglobulin binding domain of Streptococcal protein G", *Science*, 1991, vol. 253, pp. 657–660.

Güntert, P. et al., "Torison angle dynamics for NMR structure calculation with the new program DYANA", *J. Mol. Biol.*, 1997, vol. 273, pp. 283–298.

Hao, M.–H. et al., "Unfolding and refolding of the native structure of bovine pancreatic trypsin inhibitor studied by computer simulations", *Biochem.*, 1993, vol. 32, pp. 9614–9631.

Hertz, D. et al., "Two results on bounding the roots of interval polynomials", *Comput. Chem. Eng.*, 1999, vol. 23, pp. 1333–1339.

Hinds, D. et al., "Exploring conformational space with a simple lattice model for protein structure", *J. Mol. Biol.*, 1994, vol. 243, pp. 668–682.

Honig, B. et al., "Macroscopic models of aqueous solutions: Biological and chemical applications", *J. Phys. Chem.*, 1993, vol. 97, pp. 1101–1109.

Honig, B. et al., "Free energy balance in protein folding", *Adv. Prot. Chem.*, 1995, vol. 46, pp. 27–58.

Honig, B. Et al., "Classical electrostatics in biology and chemistry", *Science*, 1995, vol. 268, pp. 1144–1149.

Honig, B. et al., "Adding backbone to protein folding: why proteins are polypeptides", *Fold. Des.*, 1996, vol. 1, No. 1, pp. R17–R20.

Itzhaki, L. et al., "The structure of the transition state for folding of chymotrypsin inhibitor 2 analysed by protein engineering methods. Evidence for a nucleation–condensation mechanism for protein folding", *J. Mol. Biol.*, 1995, vol. 254, pp. 260–288.

Jackson, S. et al., "Folding of Chymotrypsin Inhibitor 2: 1. Evidence for a two–state transition", *Biochemistry*, 1991, vol. 30, pp. 10428–10435.

Jain, A. et al., "A fast recursive algorithm for molecular dynamics simulation", *J. Comp. Phys.*, 1993, vol. 106, pp. 258–268.

Jones, D., "Protein secondary structure prediction based on position–specific scoring matrices", *J. Mol. Biol.*, 1999, vol. 292, pp. 195–202.

Kabsch, W. et al., "Dictionary of protein secondary structure: Pattern receognition of hydrogen–bonded and geometrical features", *Biopolymers*, 1983, vol. 22, pp. 2577–2637.

Karplus, P. et al., "Hydrophobicity regained", *Protein Science*, 1997, vol. 6, pp. 1302–1307.

Klepeis, J. et al., "Predicting solvated peptide conformations via global minimization of energetic atom–to–atom interactions", *Comput. Chem. Engng.*, 1998, vol. 22, No. 6, pp. 765–788.

Klepeis, J. et al., "Free–energy calculations for peptides via deterministic global optimization", *J. Chem. Phys.*, 1999, vol. 110, No. 15, pp. 7491–7512.

Klepeis, J. et al., "Predicting peptide structures using NMR data and deterministic global optimization", *J. Comp. Chem.*, 1999, vol. 20, No. 13, pp. 1354–1370.

Klepeis, J. et al., "Comparative study of global minimum energy conformations of hydrated peptides", *J. Comp. Chem.*, 1999, vol. 20, No. 6, pp. 636–654.

Koehl, P. et al., "A brighter future for protein structure prediction", *Nature Structural Biology*, 1999, vol. 6, No. 2, pp. 108–111.

Lazaridis, T. et al., "'New View' of protein folding reconciled with the old through multiple unfolding simulations", *Science*, 1997, vol. 278, pp. 1928–1931.

Lee, J. et al., "Conformational analysis of the 20–residue membrane–bound portion of melittin by conformational space annealing", *Biopolymers*, 1998, vol. 46, pp. 103–115.

Lee, J. et al., "New optimization method for conformational energy calculations on polypeptides: Conformational space annealing", *J. Comput. Chem.*, vol. 18, pp. 1222–1232.

Lesser, G. et al., "Hydrophobicity of amino acid subgroups in proteins", *Proteins*, 1990, vol. 8, pp. 6–13.

Levitt, M. et al.,"Protein folding by restrained energy minimization and molecular dynamics", *J. Mol. Biol.*, 1983, vol. 170, pp. 723–764.

Lim, W. et al., "The role of internal packing interactions in determining the structure and stability of a protein", *J. Mol. Biol.*, 1991, vol. 219, pp. 359–376.

Liwo, A. et al., "Protein structure prediction by global optimization of a potential energy function", *PNAS USA*, 1999, vol. 96, pp. 5482–5485.

Maranas, C. et al., in DIMACS Series in Discrete Mathematics and Theoretical Science, vol. 23, pp. 133–150, American Mathematical Society, 1996.

Maranas, C. et al., "A deterministic global optimization approach for molecular structure determination", *J. Chem. Phys.*, 1994, vol. 100, No. 2, pp. 1247–1261.

Maranas, C. et al., "Global optimization for molecular conformation problems", *Annals of Operations Research*, 1993, vol. 42, pp. 85–117.

Maranas, C. et al., "Global minimum potential energy conformations of small molecules", *J. Glob. Opt.*, 1994, vol. 4, pp. 135–170.

Maranas, C. et al., "A global optimization approach for Lennard–Jones microclusters", *J. Chem. Phys.*, 1992, vol. 97, No. 10, pp. 7667–7678.

McGuffin, L. et al., "The PSIPRED protein structure prediction server", *Bioinformatics*, 2000, vol. 16, No. 4, pp. 404–405.

Minor, D. et al., "Context–dependent secondary structure formation of a designed protein sequence", *Nature*, 1996, vol. 380, pp. 730–734.

Monge, A. et al., "An algorithm to generate low–resolution protein tertiary structures from knowledge of secondary structure", *PNAS USA*, 1994, vol. 91, pp. 5027–5029.

Monge, A. et al., "Computer modeling of protein folding: Conformational and energetic analysis of reduced and detailed protein models", *J. Mol. Biol.*, 1995, vol. 247, pp. 995–1012.

Morikis, D. et al., "Solution structure of Compstatin, a potent complement inhibitor", *Protein Science*, 1998, vol. 7, pp. 619–627.

Morikis, D. et al., Compstatin, NRM, 21 Structures, Protein Data Bank Accession No. 1AlP, Dec. 12, 1997, 74 pages.

Muñoz, V. et al., "Elucidating the folding problem of helical peptides using empirical parameters", *Nat. Struct. Biol.*, 1994, vol. 1, No. 6, pp. 399–409.

Muñoz, V. et al., "Folding dynamics and mechanism of β–hairpin formation", *Nature*, 1997, vol. 390, pp. 196–199.

Némethy, G. et al., "Energy parameters in polypeptides. 10. Improved geometrical parameters and nonbonded interactions for use in the ECEPP/3 algorithm, with application to proline–containing peptides", *J. Phys. Chem.*, 1992, vol. 96, pp. 6472–6484.

Niermann, T. et al., "Prediction of tertiary structure of the α subunit of tryptophan synthase", *Biol. Chem*, 1987, vol. 368, pp. 1087–1088.

Nölting, B. et al., "Analysis of the folding pathway of chymotrypsin inhibitor by correlation of Φ–values with inter–residue contacts", *J. Theor. Biol.*, 1999, vol. 197, pp. 113–121.

Orengo, C. et al., "Analysis and assessment of Ab initio three–dimensional prediction, secondary structure, and contacts prediction", *Proteins Suppl.*, 1999, vol. 3, pp. 149–170.

Ortiz, A., et al., "Nativelike topology assembly of small proteins using predicted restraints in Monte Carlo folding simulations", *PNAS USA*, 1998, vol. 95, pp. 1020–1025.

Pande, V. et al., "Molecular dynamics simulations of unfolding and refolding of αβ–hairpin fragment of protein G", *PNAS USA*, 1999, vol. 96, pp. 9062–9067.

Radzicka, A. et al., "Comparing the polarities of the amino acids: Side–chain distribution coefficients between the vapor phase, cyclohexane, 1–octanol, and neutral aqueous solution", *Biochem*, 1988, vol. 27, pp. 1664–1670.

Rice, L. et al., "Torsion angle dynamics: Reduced variable conformational sampling enhances crystallographic structure refinement", *Proteins*, 1994, vol. 19, pp. 277–290.

Ripoll, D. et al., "Coupling between folding and ionization equilibria: Effects of pH on the conformational preferences of polypeptides", *J. Mol. Biol.*, 1996, vol. 264, pp. 770–783.

Rose, G. et al., "Hydrophobicity of amino acid residues in globular proteins", *Science*, 1985, vol. 229, pp. 834–838.

Rost, B. et al., "Secondary structure prediction of all–helical proteins in two states", *Protein Eng.*, 1993, vol. 6, pp. 831–836.

Scheraga, A. et al., "Surmounting the multiple–minima problem in protein folding", *J. Glob. Opt.*, 1999, vol. 15, pp. 235–260.

Shortle, D. et al., "Clustering of low–energy conformations near the native structures of small proteins", *PNAS USA*, Sep. 1998, vol. 95, pp. 11158–11162.

Simons, K. et al., "Improved recognition of native–like protein structures using a combination of sequence–dependent and sequence–independent features of proteins", *Proteins*, 1999, vol. 34, pp. 82–95.

Skolnick, J. et al., "MONSSTER: A method for folding globular proteins with a small number of distance restraints", *J. Mol. Biol.*, 1997, vol. 265, pp. 217–241.

Srinivasan, R. et al., "A physical basis for protein secondary structure", *PNAS*, 1999, vol. 96, No. 25, pp. 14258–14263.

Standley D. et al., "A Branch and bound algorithm for protein structure refinement from sparse NMR data sets", *J. Mol. Biol*, 1999, vol. 285, pp. 1691–1710.

States, D. et al., "Conformations of intermediates in the folding of the pancreatic trypsin inhibitor", *J. Mol. Biol.*, 1987, vol. 195, pp. 731–739.

Stillinger, F. et al., "Nonlinear optimization simplified by hypersurface deformation", *J. Stat. Phys.,* 1988, vol. 52, Nos. 5/6, pp. 1429–1445.

Sun, S. et al., "a simple protein folding algorithm using a binary code and secondary structure constraints", *Protein Engineering,* 1995, vol. 8, No. 8, pp. 769–778.

Vorobjev, Y. et al., "A fast adaptive multigrid boundary element method for macromolecular electrostatic computations in a solvent", *J. Comput. Chem.,* 1997, vol. 18, No. 4, pp. 569–583.

Wales, D. et al., "Global optimization of clusters, crystals, and biomolecules", *Science,* 1999, vol. 285, pp. 1368–1372.

Weissman, J. et al., "Reexamination of the folding BPTI: Predominance of native intermediates", *Science,* 1991, vol. 253, pp. 1386–1393.

Wlodawer, A. et al., "Structure of bovine pancreatic trypsin inhibitor", *J. Mol. Biol.,* 1984, vol. 180, pp. 301–329.

Yang, A. et al., "On the calculation of $Pk_aS$ in Proteins", *Proteins,* 1993, vol. 15, pp. 252–265.

Yue, K. et al., "Folding proteins with a simple energy function and extensive conformational searching", *Protein Science,* 1996, vol. 5, pp. 254–261.

Copy of the Invitation to Pay Additional Fees dated Apr. 15, 2002 (PCT/US02/04644).

Floudas, C.A. et al., "Structure prediction in protein folding," *AAAS Annual Meeting and Science Innovation Exposition,* Feb. 15, 2001, XP001121231, 167, p. A40.

Klepeis, J.L., et al., "Ab initio prediction of helical segments in polypeptides," *J. Computational Chem., USA,* Jan. 2002, XP001121226, 23(2), 245–266.

* cited by examiner $$E_{ECEPP/3} = \sum_{(ij) \in ES} \frac{q_i q_j}{r_{ij}} \quad \text{(Electrostatic)}$$

$$+ \sum_{(ij) \in NB} F_{ij} \frac{A_{ij}}{r_{ij}^{12}} - \frac{C_{ij}}{r_{ij}^{6}} \quad \text{(Nonbonded)}$$

$$+ \sum_{(ij) \in HX} \frac{A'_{ij}}{r_{ij}^{12}} - \frac{B_{ij}}{r_{ij}^{10}} \quad \text{(Hydrogen bonded)}$$

$$+ \sum_{k \in TOR} (\frac{E_{o,k}}{2})(1 + c_k \cos n_k \theta_k) \quad \text{(Torsional)}$$

Figure 4

**Initial Conformer
Free energy based
on vacuum potential**

$F_{cavity} = \gamma(SA) + b$ $F_{solv} = F_{polar}(\varepsilon=80)$
$\quad\quad - F_{polar}(\varepsilon=1)$ $F_{ionize}(pH) = kT \ln(Z)$ symmetric, non-intersecting anti-symmetric, non-intersecting symmetric, intersecting anti-symmetric, intersecting

SEQUENCE LISTING

<160> NUMBER OF SEQ ID NOS: 170

<210> SEQ ID NO 1
<211> LENGTH: 5
<212> TYPE: PRT
<213> ORGANISM: Bos taurus

<400> SEQUENCE: 1

Arg Pro Asp Phe Cys
1               5

<210> SEQ ID NO 2

```
<211> LENGTH: 5
<212> TYPE: PRT
<213> ORGANISM: Bos taurus

<400> SEQUENCE: 2

Pro Asp Phe Cys Leu
1               5

<210> SEQ ID NO 3
<211> LENGTH: 5
<212> TYPE: PRT
<213> ORGANISM: Bos taurus

<400> SEQUENCE: 3

Asp Phe Cys Leu Glu
1               5

<210> SEQ ID NO 4
<211> LENGTH: 5
<212> TYPE: PRT
<213> ORGANISM: Bos taurus

<400> SEQUENCE: 4

Phe Cys Leu Glu Pro
1               5

<210> SEQ ID NO 5
<211> LENGTH: 5
<212> TYPE: PRT
<213> ORGANISM: Bos taurus

<400> SEQUENCE: 5

Cys Leu Glu Pro Pro
1               5

<210> SEQ ID NO 6
<211> LENGTH: 5
<212> TYPE: PRT
<213> ORGANISM: Bos taurus

<400> SEQUENCE: 6

Leu Glu Pro Pro Tyr
1               5

<210> SEQ ID NO 7
<211> LENGTH: 5
<212> TYPE: PRT
<213> ORGANISM: Bos taurus

<400> SEQUENCE: 7

Glu Pro Pro Tyr Thr
1               5

<210> SEQ ID NO 8
<211> LENGTH: 5
<212> TYPE: PRT
<213> ORGANISM: Bos taurus

<400> SEQUENCE: 8

Pro Pro Tyr Thr Gly
1               5

<210> SEQ ID NO 9
<211> LENGTH: 5
<212> TYPE: PRT
```

```
<213> ORGANISM: Bos taurus

<400> SEQUENCE: 9

Pro Tyr Thr Gly Pro
1               5

<210> SEQ ID NO 10
<211> LENGTH: 5
<212> TYPE: PRT
<213> ORGANISM: Bos taurus

<400> SEQUENCE: 10

Tyr Thr Gly Pro Cys
1               5

<210> SEQ ID NO 11
<211> LENGTH: 5
<212> TYPE: PRT
<213> ORGANISM: Bos taurus

<400> SEQUENCE: 11

Thr Gly Pro Cys Lys
1               5

<210> SEQ ID NO 12
<211> LENGTH: 5
<212> TYPE: PRT
<213> ORGANISM: Bos taurus

<400> SEQUENCE: 12

Gly Pro Cys Lys Ala
1               5

<210> SEQ ID NO 13
<211> LENGTH: 5
<212> TYPE: PRT
<213> ORGANISM: Bos taurus

<400> SEQUENCE: 13

Pro Cys Lys Ala Arg
1               5

<210> SEQ ID NO 14
<211> LENGTH: 5
<212> TYPE: PRT
<213> ORGANISM: Bos taurus

<400> SEQUENCE: 14

Cys Lys Ala Arg Ile
1               5

<210> SEQ ID NO 15
<211> LENGTH: 5
<212> TYPE: PRT
<213> ORGANISM: Bos taurus

<400> SEQUENCE: 15

Lys Ala Arg Ile Ile
1               5

<210> SEQ ID NO 16
<211> LENGTH: 5
<212> TYPE: PRT
<213> ORGANISM: Bos taurus
```

```
<400> SEQUENCE: 16

Ala Arg Ile Ile Arg
1               5

<210> SEQ ID NO 17
<211> LENGTH: 5
<212> TYPE: PRT
<213> ORGANISM: Bos taurus

<400> SEQUENCE: 17

Arg Ile Ile Arg Tyr
1               5

<210> SEQ ID NO 18
<211> LENGTH: 5
<212> TYPE: PRT
<213> ORGANISM: Bos taurus

<400> SEQUENCE: 18

Ile Ile Arg Tyr Phe
1               5

<210> SEQ ID NO 19
<211> LENGTH: 5
<212> TYPE: PRT
<213> ORGANISM: Bos taurus

<400> SEQUENCE: 19

Ile Arg Tyr Phe Tyr
1               5

<210> SEQ ID NO 20
<211> LENGTH: 5
<212> TYPE: PRT
<213> ORGANISM: Bos taurus

<400> SEQUENCE: 20

Arg Tyr Phe Tyr Asn
1               5

<210> SEQ ID NO 21
<211> LENGTH: 5
<212> TYPE: PRT
<213> ORGANISM: Bos taurus

<400> SEQUENCE: 21

Tyr Phe Tyr Asn Ala
1               5

<210> SEQ ID NO 22
<211> LENGTH: 5
<212> TYPE: PRT
<213> ORGANISM: Bos taurus

<400> SEQUENCE: 22

Phe Tyr Asn Ala Lys
1               5

<210> SEQ ID NO 23
<211> LENGTH: 5
<212> TYPE: PRT
<213> ORGANISM: Bos taurus

<400> SEQUENCE: 23
```

-continued

```
Tyr Asn Ala Lys Ala
1               5

<210> SEQ ID NO 24
<211> LENGTH: 5
<212> TYPE: PRT
<213> ORGANISM: Bos taurus

<400> SEQUENCE: 24

Asn Ala Lys Ala Gly
1               5

<210> SEQ ID NO 25
<211> LENGTH: 5
<212> TYPE: PRT
<213> ORGANISM: Bos taurus

<400> SEQUENCE: 25

Ala Lys Ala Gly Leu
1               5

<210> SEQ ID NO 26
<211> LENGTH: 5
<212> TYPE: PRT
<213> ORGANISM: Bos taurus

<400> SEQUENCE: 26

Lys Ala Gly Leu Cys
1               5

<210> SEQ ID NO 27
<211> LENGTH: 5
<212> TYPE: PRT
<213> ORGANISM: Bos taurus

<400> SEQUENCE: 27

Ala Gly Leu Cys Gln
1               5

<210> SEQ ID NO 28
<211> LENGTH: 5
<212> TYPE: PRT
<213> ORGANISM: Bos taurus

<400> SEQUENCE: 28

Gly Leu Cys Gln Thr
1               5

<210> SEQ ID NO 29
<211> LENGTH: 5
<212> TYPE: PRT
<213> ORGANISM: Bos taurus

<400> SEQUENCE: 29

Leu Cys Gln Thr Phe
1               5

<210> SEQ ID NO 30
<211> LENGTH: 5
<212> TYPE: PRT
<213> ORGANISM: Bos taurus

<400> SEQUENCE: 30

Cys Gln Thr Phe Val
1               5
```

```
<210> SEQ ID NO 31
<211> LENGTH: 5
<212> TYPE: PRT
<213> ORGANISM: Bos taurus

<400> SEQUENCE: 31

Gln Thr Phe Val Tyr
1               5

<210> SEQ ID NO 32
<211> LENGTH: 5
<212> TYPE: PRT
<213> ORGANISM: Bos taurus

<400> SEQUENCE: 32

Thr Phe Val Tyr Gly
1               5

<210> SEQ ID NO 33
<211> LENGTH: 5
<212> TYPE: PRT
<213> ORGANISM: Bos taurus

<400> SEQUENCE: 33

Phe Val Tyr Gly Gly
1               5

<210> SEQ ID NO 34
<211> LENGTH: 5
<212> TYPE: PRT
<213> ORGANISM: Bos taurus

<400> SEQUENCE: 34

Val Tyr Gly Gly Cys
1               5

<210> SEQ ID NO 35
<211> LENGTH: 5
<212> TYPE: PRT
<213> ORGANISM: Bos taurus

<400> SEQUENCE: 35

Tyr Gly Gly Cys Arg
1               5

<210> SEQ ID NO 36
<211> LENGTH: 5
<212> TYPE: PRT
<213> ORGANISM: Bos taurus

<400> SEQUENCE: 36

Gly Gly Cys Arg Ala
1               5

<210> SEQ ID NO 37
<211> LENGTH: 5
<212> TYPE: PRT
<213> ORGANISM: Bos taurus

<400> SEQUENCE: 37

Gly Cys Arg Ala Lys
1               5
```

```
<210> SEQ ID NO 38
<211> LENGTH: 5
<212> TYPE: PRT
<213> ORGANISM: Bos taurus

<400> SEQUENCE: 38

Cys Arg Ala Lys Arg
1               5

<210> SEQ ID NO 39
<211> LENGTH: 5
<212> TYPE: PRT
<213> ORGANISM: Bos taurus

<400> SEQUENCE: 39

Arg Ala Lys Arg Asn
1               5

<210> SEQ ID NO 40
<211> LENGTH: 5
<212> TYPE: PRT
<213> ORGANISM: Bos taurus

<400> SEQUENCE: 40

Ala Lys Arg Asn Asn
1               5

<210> SEQ ID NO 41
<211> LENGTH: 5
<212> TYPE: PRT
<213> ORGANISM: Bos taurus

<400> SEQUENCE: 41

Lys Arg Asn Asn Phe
1               5

<210> SEQ ID NO 42
<211> LENGTH: 5
<212> TYPE: PRT
<213> ORGANISM: Bos taurus

<400> SEQUENCE: 42

Arg Asn Asn Phe Lys
1               5

<210> SEQ ID NO 43
<211> LENGTH: 5
<212> TYPE: PRT
<213> ORGANISM: Bos taurus

<400> SEQUENCE: 43

Asn Asn Phe Lys Ser
1               5

<210> SEQ ID NO 44
<211> LENGTH: 5
<212> TYPE: PRT
<213> ORGANISM: Bos taurus

<400> SEQUENCE: 44

Asn Phe Lys Ser Ala
1               5

<210> SEQ ID NO 45
<211> LENGTH: 5
```

```
<212> TYPE: PRT
<213> ORGANISM: Bos taurus

<400> SEQUENCE: 45

Phe Lys Ser Ala Glu
1               5

<210> SEQ ID NO 46
<211> LENGTH: 5
<212> TYPE: PRT
<213> ORGANISM: Bos taurus

<400> SEQUENCE: 46

Lys Ser Ala Glu Asp
1               5

<210> SEQ ID NO 47
<211> LENGTH: 5
<212> TYPE: PRT
<213> ORGANISM: Bos taurus

<400> SEQUENCE: 47

Ser Ala Glu Asp Cys
1               5

<210> SEQ ID NO 48
<211> LENGTH: 5
<212> TYPE: PRT
<213> ORGANISM: Bos taurus

<400> SEQUENCE: 48

Ala Glu Asp Cys Met
1               5

<210> SEQ ID NO 49
<211> LENGTH: 5
<212> TYPE: PRT
<213> ORGANISM: Bos taurus

<400> SEQUENCE: 49

Glu Asp Cys Met Arg
1               5

<210> SEQ ID NO 50
<211> LENGTH: 5
<212> TYPE: PRT
<213> ORGANISM: Bos taurus

<400> SEQUENCE: 50

Asp Cys Met Arg Thr
1               5

<210> SEQ ID NO 51
<211> LENGTH: 5
<212> TYPE: PRT
<213> ORGANISM: Bos taurus

<400> SEQUENCE: 51

Cys Met Arg Thr Cys
1               5

<210> SEQ ID NO 52
<211> LENGTH: 5
<212> TYPE: PRT
<213> ORGANISM: Bos taurus
```

```
<400> SEQUENCE: 52

Met Arg Thr Cys Gly
1               5

<210> SEQ ID NO 53
<211> LENGTH: 5
<212> TYPE: PRT
<213> ORGANISM: Bos taurus

<400> SEQUENCE: 53

Arg Thr Cys Gly Gly
1               5

<210> SEQ ID NO 54
<211> LENGTH: 5
<212> TYPE: PRT
<213> ORGANISM: Bos taurus

<400> SEQUENCE: 54

Thr Cys Gly Gly Ala
1               5

<210> SEQ ID NO 55
<211> LENGTH: 58
<212> TYPE: PRT
<213> ORGANISM: Bos taurus

<400> SEQUENCE: 55

Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala
    50                  55

<210> SEQ ID NO 56
<211> LENGTH: 56
<212> TYPE: PRT
<213> ORGANISM: Streptomyces griseus

<400> SEQUENCE: 56

Met Thr Tyr Lys Leu Ile Leu Asn Gly Lys Thr Leu Lys Gly Glu Thr
1               5                   10                  15

Thr Thr Glu Ala Val Asp Ala Ala Thr Ala Glu Lys Val Phe Lys Gln
            20                  25                  30

Tyr Ala Asn Asp Asn Gly Val Asp Gly Glu Trp Thr Tyr Asp Asp Ala
        35                  40                  45

Thr Lys Thr Phe Thr Val Thr Glu
    50                  55

<210> SEQ ID NO 57
<211> LENGTH: 5
<212> TYPE: PRT
<213> ORGANISM: Streptomyces griseus

<400> SEQUENCE: 57

Met Thr Tyr Lys Leu
1               5
```

```
<210> SEQ ID NO 58
<211> LENGTH: 5
<212> TYPE: PRT
<213> ORGANISM: Streptomyces griseus

<400> SEQUENCE: 58

Thr Tyr Lys Leu Ile
1               5

<210> SEQ ID NO 59
<211> LENGTH: 5
<212> TYPE: PRT
<213> ORGANISM: Streptomyces griseus

<400> SEQUENCE: 59

Tyr Lys Leu Ile Leu
1               5

<210> SEQ ID NO 60
<211> LENGTH: 5
<212> TYPE: PRT
<213> ORGANISM: Streptomyces griseus

<400> SEQUENCE: 60

Lys Leu Ile Leu Asn
1               5

<210> SEQ ID NO 61
<211> LENGTH: 5
<212> TYPE: PRT
<213> ORGANISM: Streptomyces griseus

<400> SEQUENCE: 61

Leu Ile Leu Asn Gly
1               5

<210> SEQ ID NO 62
<211> LENGTH: 5
<212> TYPE: PRT
<213> ORGANISM: Streptomyces griseus

<400> SEQUENCE: 62

Ile Leu Asn Gly Lys
1               5

<210> SEQ ID NO 63
<211> LENGTH: 5
<212> TYPE: PRT
<213> ORGANISM: Streptomyces griseus

<400> SEQUENCE: 63

Leu Asn Gly Lys Thr
1               5

<210> SEQ ID NO 64
<211> LENGTH: 5
<212> TYPE: PRT
<213> ORGANISM: Streptomyces griseus

<400> SEQUENCE: 64

Asn Gly Lys Thr Leu
1               5

<210> SEQ ID NO 65
```

```
<211> LENGTH: 5
<212> TYPE: PRT
<213> ORGANISM: Streptomyces griseus

<400> SEQUENCE: 65

Gly Lys Thr Leu Lys
1               5

<210> SEQ ID NO 66
<211> LENGTH: 5
<212> TYPE: PRT
<213> ORGANISM: Streptomyces griseus

<400> SEQUENCE: 66

Lys Thr Leu Lys Gly
1               5

<210> SEQ ID NO 67
<211> LENGTH: 5
<212> TYPE: PRT
<213> ORGANISM: Streptomyces griseus

<400> SEQUENCE: 67

Thr Leu Lys Gly Glu
1               5

<210> SEQ ID NO 68
<211> LENGTH: 5
<212> TYPE: PRT
<213> ORGANISM: Streptomyces griseus

<400> SEQUENCE: 68

Leu Lys Gly Glu Thr
1               5

<210> SEQ ID NO 69
<211> LENGTH: 5
<212> TYPE: PRT
<213> ORGANISM: Streptomyces griseus

<400> SEQUENCE: 69

Lys Gly Glu Thr Thr
1               5

<210> SEQ ID NO 70
<211> LENGTH: 5
<212> TYPE: PRT
<213> ORGANISM: Streptomyces griseus

<400> SEQUENCE: 70

Gly Glu Thr Thr Thr
1               5

<210> SEQ ID NO 71
<211> LENGTH: 5
<212> TYPE: PRT
<213> ORGANISM: Streptomyces griseus

<400> SEQUENCE: 71

Glu Thr Thr Thr Glu
1               5

<210> SEQ ID NO 72
<211> LENGTH: 5
<212> TYPE: PRT
```

<213> ORGANISM: Streptomyces griseus

<400> SEQUENCE: 72

Thr Thr Thr Glu Ala
1               5

<210> SEQ ID NO 73
<211> LENGTH: 5
<212> TYPE: PRT
<213> ORGANISM: Streptomyces griseus

<400> SEQUENCE: 73

Thr Thr Glu Ala Val
1               5

<210> SEQ ID NO 74
<211> LENGTH: 5
<212> TYPE: PRT
<213> ORGANISM: Streptomyces griseus

<400> SEQUENCE: 74

Thr Glu Ala Val Asp
1               5

<210> SEQ ID NO 75
<211> LENGTH: 5
<212> TYPE: PRT
<213> ORGANISM: Streptomyces griseus

<400> SEQUENCE: 75

Glu Ala Val Asp Ala
1               5

<210> SEQ ID NO 76
<211> LENGTH: 5
<212> TYPE: PRT
<213> ORGANISM: Streptomyces griseus

<400> SEQUENCE: 76

Ala Val Asp Ala Ala
1               5

<210> SEQ ID NO 77
<211> LENGTH: 5
<212> TYPE: PRT
<213> ORGANISM: Streptomyces griseus

<400> SEQUENCE: 77

Val Asp Ala Ala Thr
1               5

<210> SEQ ID NO 78
<211> LENGTH: 5
<212> TYPE: PRT
<213> ORGANISM: Streptomyces griseus

<400> SEQUENCE: 78

Asp Ala Ala Thr Ala
1               5

<210> SEQ ID NO 79
<211> LENGTH: 5
<212> TYPE: PRT
<213> ORGANISM: Streptomyces griseus -continued

```
<400> SEQUENCE: 79

Ala Ala Thr Ala Glu
1               5

<210> SEQ ID NO 80
<211> LENGTH: 5
<212> TYPE: PRT
<213> ORGANISM: Streptomyces griseus

<400> SEQUENCE: 80

Ala Thr Ala Glu Lys
1               5

<210> SEQ ID NO 81
<211> LENGTH: 5
<212> TYPE: PRT
<213> ORGANISM: Streptomyces griseus

<400> SEQUENCE: 81

Thr Ala Glu Lys Val
1               5

<210> SEQ ID NO 82
<211> LENGTH: 5
<212> TYPE: PRT
<213> ORGANISM: Streptomyces griseus

<400> SEQUENCE: 82

Ala Glu Lys Val Phe
1               5

<210> SEQ ID NO 83
<211> LENGTH: 5
<212> TYPE: PRT
<213> ORGANISM: Streptomyces griseus

<400> SEQUENCE: 83

Glu Lys Val Phe Lys
1               5

<210> SEQ ID NO 84
<211> LENGTH: 5
<212> TYPE: PRT
<213> ORGANISM: Streptomyces griseus

<400> SEQUENCE: 84

Lys Val Phe Lys Gln
1               5

<210> SEQ ID NO 85
<211> LENGTH: 5
<212> TYPE: PRT
<213> ORGANISM: Streptomyces griseus

<400> SEQUENCE: 85

Val Phe Lys Gln Tyr
1               5

<210> SEQ ID NO 86
<211> LENGTH: 5
<212> TYPE: PRT
<213> ORGANISM: Streptomyces griseus

<400> SEQUENCE: 86
```

```
Phe Lys Gln Tyr Ala
1               5

<210> SEQ ID NO 87
<211> LENGTH: 5
<212> TYPE: PRT
<213> ORGANISM: Streptomyces griseus

<400> SEQUENCE: 87

Lys Gln Tyr Ala Asn
1               5

<210> SEQ ID NO 88
<211> LENGTH: 5
<212> TYPE: PRT
<213> ORGANISM: Streptomyces griseus

<400> SEQUENCE: 88

Gln Tyr Ala Asn Asp
1               5

<210> SEQ ID NO 89
<211> LENGTH: 5
<212> TYPE: PRT
<213> ORGANISM: Streptomyces griseus

<400> SEQUENCE: 89

Tyr Ala Asn Asp Asn
1               5

<210> SEQ ID NO 90
<211> LENGTH: 5
<212> TYPE: PRT
<213> ORGANISM: Streptomyces griseus

<400> SEQUENCE: 90

Ala Asn Asp Asn Gly
1               5

<210> SEQ ID NO 91
<211> LENGTH: 5
<212> TYPE: PRT
<213> ORGANISM: Streptomyces griseus

<400> SEQUENCE: 91

Asn Asp Asn Gly Val
1               5

<210> SEQ ID NO 92
<211> LENGTH: 5
<212> TYPE: PRT
<213> ORGANISM: Streptomyces griseus

<400> SEQUENCE: 92

Asp Asn Gly Val Asp
1               5

<210> SEQ ID NO 93
<211> LENGTH: 5
<212> TYPE: PRT
<213> ORGANISM: Streptomyces griseus

<400> SEQUENCE: 93

Asn Gly Val Asp Gly
1               5
```

```
<210> SEQ ID NO 94
<211> LENGTH: 5
<212> TYPE: PRT
<213> ORGANISM: Streptomyces griseus

<400> SEQUENCE: 94

Gly Val Asp Gly Glu
1               5

<210> SEQ ID NO 95
<211> LENGTH: 5
<212> TYPE: PRT
<213> ORGANISM: Streptomyces griseus

<400> SEQUENCE: 95

Val Asp Gly Glu Trp
1               5

<210> SEQ ID NO 96
<211> LENGTH: 5
<212> TYPE: PRT
<213> ORGANISM: Streptomyces griseus

<400> SEQUENCE: 96

Asp Gly Glu Trp Thr
1               5

<210> SEQ ID NO 97
<211> LENGTH: 5
<212> TYPE: PRT
<213> ORGANISM: Streptomyces griseus

<400> SEQUENCE: 97

Gly Glu Trp Thr Tyr
1               5

<210> SEQ ID NO 98
<211> LENGTH: 5
<212> TYPE: PRT
<213> ORGANISM: Streptomyces griseus

<400> SEQUENCE: 98

Glu Trp Thr Tyr Asp
1               5

<210> SEQ ID NO 99
<211> LENGTH: 5
<212> TYPE: PRT
<213> ORGANISM: Streptomyces griseus

<400> SEQUENCE: 99

Trp Thr Tyr Asp Asp
1               5

<210> SEQ ID NO 100
<211> LENGTH: 5
<212> TYPE: PRT
<213> ORGANISM: Streptomyces griseus

<400> SEQUENCE: 100

Thr Tyr Asp Asp Ala
1               5
```

```
<210> SEQ ID NO 101
<211> LENGTH: 5
<212> TYPE: PRT
<213> ORGANISM: Streptomyces griseus

<400> SEQUENCE: 101

Tyr Asp Asp Ala Thr
1               5

<210> SEQ ID NO 102
<211> LENGTH: 5
<212> TYPE: PRT
<213> ORGANISM: Streptomyces griseus

<400> SEQUENCE: 102

Asp Asp Ala Thr Lys
1               5

<210> SEQ ID NO 103
<211> LENGTH: 5
<212> TYPE: PRT
<213> ORGANISM: Streptomyces griseus

<400> SEQUENCE: 103

Asp Ala Thr Lys Thr
1               5

<210> SEQ ID NO 104
<211> LENGTH: 5
<212> TYPE: PRT
<213> ORGANISM: Streptomyces griseus

<400> SEQUENCE: 104

Ala Thr Lys Thr Phe
1               5

<210> SEQ ID NO 105
<211> LENGTH: 5
<212> TYPE: PRT
<213> ORGANISM: Streptomyces griseus

<400> SEQUENCE: 105

Thr Lys Thr Phe Thr
1               5

<210> SEQ ID NO 106
<211> LENGTH: 5
<212> TYPE: PRT
<213> ORGANISM: Streptomyces griseus

<400> SEQUENCE: 106

Lys Thr Phe Thr Val
1               5

<210> SEQ ID NO 107
<211> LENGTH: 5
<212> TYPE: PRT
<213> ORGANISM: Streptomyces griseus

<400> SEQUENCE: 107

Thr Phe Thr Val Thr
1               5

<210> SEQ ID NO 108
<211> LENGTH: 5
```

```
<212> TYPE: PRT
<213> ORGANISM: Streptomyces griseus

<400> SEQUENCE: 108

Phe Thr Val Thr Glu
1               5

<210> SEQ ID NO 109
<211> LENGTH: 63
<212> TYPE: PRT
<213> ORGANISM: Hordeum vulgare

<400> SEQUENCE: 109

Lys Thr Glu Trp Pro Glu Leu Val Gly Lys Ser Val Glu Glu Ala Lys
1               5                   10                  15

Lys Val Ile Leu Gln Asp Lys Pro Glu Ala Gln Ile Ile Val Leu Pro
                20                  25                  30

Val Gly Thr Ile Val Thr Met Glu Tyr Arg Ile Asp Arg Val Arg Leu
            35                  40                  45

Phe Val Asp Lys Leu Asp Asn Ile Ala Gln Val Pro Arg Val Gly
        50                  55                  60

<210> SEQ ID NO 110
<211> LENGTH: 5
<212> TYPE: PRT
<213> ORGANISM: Hordeum vulgare

<400> SEQUENCE: 110

Lys Thr Glu Trp Pro
1               5

<210> SEQ ID NO 111
<211> LENGTH: 5
<212> TYPE: PRT
<213> ORGANISM: Hordeum vulgare

<400> SEQUENCE: 111

Thr Glu Trp Pro Glu
1               5

<210> SEQ ID NO 112
<211> LENGTH: 5
<212> TYPE: PRT
<213> ORGANISM: Hordeum vulgare

<400> SEQUENCE: 112

Glu Trp Pro Glu Leu
1               5

<210> SEQ ID NO 113
<211> LENGTH: 5
<212> TYPE: PRT
<213> ORGANISM: Hordeum vulgare

<400> SEQUENCE: 113

Trp Pro Glu Leu Val
1               5

<210> SEQ ID NO 114
<211> LENGTH: 5
<212> TYPE: PRT
<213> ORGANISM: Hordeum vulgare

<400> SEQUENCE: 114
```

Pro Glu Leu Val Gly
1               5

<210> SEQ ID NO 115
<211> LENGTH: 5
<212> TYPE: PRT
<213> ORGANISM: Hordeum vulgare

<400> SEQUENCE: 115

Glu Leu Val Gly Lys
1               5

<210> SEQ ID NO 116
<211> LENGTH: 5
<212> TYPE: PRT
<213> ORGANISM: Hordeum vulgare

<400> SEQUENCE: 116

Leu Val Gly Lys Ser
1               5

<210> SEQ ID NO 117
<211> LENGTH: 5
<212> TYPE: PRT
<213> ORGANISM: Hordeum vulgare

<400> SEQUENCE: 117

Val Gly Lys Ser Val
1               5

<210> SEQ ID NO 118
<211> LENGTH: 5
<212> TYPE: PRT
<213> ORGANISM: Hordeum vulgare

<400> SEQUENCE: 118

Gly Lys Ser Val Glu
1               5

<210> SEQ ID NO 119
<211> LENGTH: 5
<212> TYPE: PRT
<213> ORGANISM: Hordeum vulgare

<400> SEQUENCE: 119

Lys Ser Val Glu Glu
1               5

<210> SEQ ID NO 120
<211> LENGTH: 5
<212> TYPE: PRT
<213> ORGANISM: Hordeum vulgare

<400> SEQUENCE: 120

Ser Val Glu Glu Ala
1               5

<210> SEQ ID NO 121
<211> LENGTH: 5
<212> TYPE: PRT
<213> ORGANISM: Hordeum vulgare

<400> SEQUENCE: 121

Val Glu Glu Ala Lys

```
1               5

<210> SEQ ID NO 122
<211> LENGTH: 5
<212> TYPE: PRT
<213> ORGANISM: Hordeum vulgare

<400> SEQUENCE: 122

Glu Glu Ala Lys Lys
1               5

<210> SEQ ID NO 123
<211> LENGTH: 5
<212> TYPE: PRT
<213> ORGANISM: Hordeum vulgare

<400> SEQUENCE: 123

Glu Ala Lys Lys Val
1               5

<210> SEQ ID NO 124
<211> LENGTH: 5
<212> TYPE: PRT
<213> ORGANISM: Hordeum vulgare

<400> SEQUENCE: 124

Ala Lys Lys Val Ile
1               5

<210> SEQ ID NO 125
<211> LENGTH: 5
<212> TYPE: PRT
<213> ORGANISM: Hordeum vulgare

<400> SEQUENCE: 125

Lys Lys Val Ile Leu
1               5

<210> SEQ ID NO 126
<211> LENGTH: 5
<212> TYPE: PRT
<213> ORGANISM: Hordeum vulgare

<400> SEQUENCE: 126

Lys Val Ile Leu Gln
1               5

<210> SEQ ID NO 127
<211> LENGTH: 5
<212> TYPE: PRT
<213> ORGANISM: Hordeum vulgare

<400> SEQUENCE: 127

Val Ile Leu Gln Asp
1               5

<210> SEQ ID NO 128
<211> LENGTH: 5
<212> TYPE: PRT
<213> ORGANISM: Hordeum vulgare

<400> SEQUENCE: 128

Ile Leu Gln Asp Lys
1               5
```

```
<210> SEQ ID NO 129
<211> LENGTH: 5
<212> TYPE: PRT
<213> ORGANISM: Hordeum vulgare

<400> SEQUENCE: 129

Leu Gln Asp Lys Pro
1               5

<210> SEQ ID NO 130
<211> LENGTH: 5
<212> TYPE: PRT
<213> ORGANISM: Hordeum vulgare

<400> SEQUENCE: 130

Gln Asp Lys Pro Glu
1               5

<210> SEQ ID NO 131
<211> LENGTH: 5
<212> TYPE: PRT
<213> ORGANISM: Hordeum vulgare

<400> SEQUENCE: 131

Asp Lys Pro Glu Ala
1               5

<210> SEQ ID NO 132
<211> LENGTH: 5
<212> TYPE: PRT
<213> ORGANISM: Hordeum vulgare

<400> SEQUENCE: 132

Lys Pro Glu Ala Gln
1               5

<210> SEQ ID NO 133
<211> LENGTH: 5
<212> TYPE: PRT
<213> ORGANISM: Hordeum vulgare

<400> SEQUENCE: 133

Pro Glu Ala Gln Ile
1               5

<210> SEQ ID NO 134
<211> LENGTH: 5
<212> TYPE: PRT
<213> ORGANISM: Hordeum vulgare

<400> SEQUENCE: 134

Glu Ala Gln Ile Ile
1               5

<210> SEQ ID NO 135
<211> LENGTH: 5
<212> TYPE: PRT
<213> ORGANISM: Hordeum vulgare

<400> SEQUENCE: 135

Ala Gln Ile Ile Val
1               5

<210> SEQ ID NO 136
```

```
<211> LENGTH: 5
<212> TYPE: PRT
<213> ORGANISM: Hordeum vulgare

<400> SEQUENCE: 136

Gln Ile Ile Val Leu
1               5

<210> SEQ ID NO 137
<211> LENGTH: 5
<212> TYPE: PRT
<213> ORGANISM: Hordeum vulgare

<400> SEQUENCE: 137

Ile Ile Val Leu Pro
1               5

<210> SEQ ID NO 138
<211> LENGTH: 5
<212> TYPE: PRT
<213> ORGANISM: Hordeum vulgare

<400> SEQUENCE: 138

Ile Val Leu Pro Val
1               5

<210> SEQ ID NO 139
<211> LENGTH: 5
<212> TYPE: PRT
<213> ORGANISM: Hordeum vulgare

<400> SEQUENCE: 139

Val Pro Arg Val Gly
1               5

<210> SEQ ID NO 140
<211> LENGTH: 5
<212> TYPE: PRT
<213> ORGANISM: Hordeum vulgare

<400> SEQUENCE: 140

Val Leu Pro Val Gly
1               5

<210> SEQ ID NO 141
<211> LENGTH: 5
<212> TYPE: PRT
<213> ORGANISM: Hordeum vulgare

<400> SEQUENCE: 141

Leu Pro Val Gly Thr
1               5

<210> SEQ ID NO 142
<211> LENGTH: 5
<212> TYPE: PRT
<213> ORGANISM: Hordeum vulgare

<400> SEQUENCE: 142

Pro Val Gly Thr Ile
1               5

<210> SEQ ID NO 143
<211> LENGTH: 5
<212> TYPE: PRT
```

-continued

<213> ORGANISM: Hordeum vulgare

<400> SEQUENCE: 143

Val Gly Thr Ile Val
1               5

<210> SEQ ID NO 144
<211> LENGTH: 5
<212> TYPE: PRT
<213> ORGANISM: Hordeum vulgare

<400> SEQUENCE: 144

Gly Thr Ile Val Thr
1               5

<210> SEQ ID NO 145
<211> LENGTH: 5
<212> TYPE: PRT
<213> ORGANISM: Hordeum vulgare

<400> SEQUENCE: 145

Thr Ile Val Thr Met
1               5

<210> SEQ ID NO 146
<211> LENGTH: 5
<212> TYPE: PRT
<213> ORGANISM: Hordeum vulgare

<400> SEQUENCE: 146

Ile Val Thr Met Glu
1               5

<210> SEQ ID NO 147
<211> LENGTH: 5
<212> TYPE: PRT
<213> ORGANISM: Hordeum vulgare

<400> SEQUENCE: 147

Val Thr Met Glu Tyr
1               5

<210> SEQ ID NO 148
<211> LENGTH: 5
<212> TYPE: PRT
<213> ORGANISM: Hordeum vulgare

<400> SEQUENCE: 148

Thr Met Glu Tyr Arg
1               5

<210> SEQ ID NO 149
<211> LENGTH: 5
<212> TYPE: PRT
<213> ORGANISM: Hordeum vulgare

<400> SEQUENCE: 149

Met Glu Tyr Arg Ile
1               5

<210> SEQ ID NO 150
<211> LENGTH: 5
<212> TYPE: PRT
<213> ORGANISM: Hordeum vulgare

<400> SEQUENCE: 150

Glu Tyr Arg Ile Asp
1               5

<210> SEQ ID NO 151
<211> LENGTH: 5
<212> TYPE: PRT
<213> ORGANISM: Hordeum vulgare

<400> SEQUENCE: 151

Tyr Arg Ile Asp Arg
1               5

<210> SEQ ID NO 152
<211> LENGTH: 5
<212> TYPE: PRT
<213> ORGANISM: Hordeum vulgare

<400> SEQUENCE: 152

Arg Ile Asp Arg Val
1               5

<210> SEQ ID NO 153
<211> LENGTH: 5
<212> TYPE: PRT
<213> ORGANISM: Hordeum vulgare

<400> SEQUENCE: 153

Ile Asp Arg Val Arg
1               5

<210> SEQ ID NO 154
<211> LENGTH: 5
<212> TYPE: PRT
<213> ORGANISM: Hordeum vulgare

<400> SEQUENCE: 154

Asp Arg Val Arg Leu
1               5

<210> SEQ ID NO 155
<211> LENGTH: 5
<212> TYPE: PRT
<213> ORGANISM: Hordeum vulgare

<400> SEQUENCE: 155

Arg Val Arg Leu Phe
1               5

<210> SEQ ID NO 156
<211> LENGTH: 5
<212> TYPE: PRT
<213> ORGANISM: Hordeum vulgare

<400> SEQUENCE: 156

Val Arg Leu Phe Val
1               5

<210> SEQ ID NO 157
<211> LENGTH: 5
<212> TYPE: PRT
<213> ORGANISM: Hordeum vulgare

<400> SEQUENCE: 157

Arg Leu Phe Val Asp
1               5

<210> SEQ ID NO 158
<211> LENGTH: 5
<212> TYPE: PRT
<213> ORGANISM: Hordeum vulgare

<400> SEQUENCE: 158

Leu Phe Val Asp Lys
1               5

<210> SEQ ID NO 159
<211> LENGTH: 5
<212> TYPE: PRT
<213> ORGANISM: Hordeum vulgare

<400> SEQUENCE: 159

Phe Val Asp Lys Leu
1               5

<210> SEQ ID NO 160
<211> LENGTH: 5
<212> TYPE: PRT
<213> ORGANISM: Hordeum vulgare

<400> SEQUENCE: 160

Val Asp Lys Leu Asp
1               5

<210> SEQ ID NO 161
<211> LENGTH: 5
<212> TYPE: PRT
<213> ORGANISM: Hordeum vulgare

<400> SEQUENCE: 161

Asp Lys Leu Asp Asn
1               5

<210> SEQ ID NO 162
<211> LENGTH: 5
<212> TYPE: PRT
<213> ORGANISM: Hordeum vulgare

<400> SEQUENCE: 162

Lys Leu Asp Asn Ile
1               5

<210> SEQ ID NO 163
<211> LENGTH: 5
<212> TYPE: PRT
<213> ORGANISM: Hordeum vulgare

<400> SEQUENCE: 163

Leu Asp Asn Ile Ala
1               5

<210> SEQ ID NO 164
<211> LENGTH: 5
<212> TYPE: PRT
<213> ORGANISM: Hordeum vulgare

<400> SEQUENCE: 164

Asp Asn Ile Ala Gln
1               5

<210> SEQ ID NO 165
<211> LENGTH: 5
<212> TYPE: PRT
<213> ORGANISM: Hordeum vulgare

<400> SEQUENCE: 165

Asn Ile Ala Gln Val
1               5

<210> SEQ ID NO 166
<211> LENGTH: 5
<212> TYPE: PRT
<213> ORGANISM: Hordeum vulgare

<400> SEQUENCE: 166

Ile Ala Gln Val Pro
1               5

<210> SEQ ID NO 167
<211> LENGTH: 5
<212> TYPE: PRT
<213> ORGANISM: Hordeum vulgare

<400> SEQUENCE: 167

Ala Gln Val Pro Arg
1               5

<210> SEQ ID NO 168
<211> LENGTH: 5
<212> TYPE: PRT
<213> ORGANISM: Hordeum vulgare

<400> SEQUENCE: 168

Gln Val Pro Arg Val
1               5

<210> SEQ ID NO 169
<211> LENGTH: 75
<212> TYPE: PRT
<213> ORGANISM: Homo sapiens

<400> SEQUENCE: 169

Met Ser Ile Gly Val Pro Ile Lys Val Leu His Glu Ala Glu Gly His
1               5                   10                  15

Ile Val Thr Cys Glu Thr Asn Thr Gly Glu Val Tyr Arg Gly Lys Leu
            20                  25                  30

Ile Glu Ala Glu Asp Asn Met Asn Cys Gln Met Ser Asn Ile Thr Val
        35                  40                  45

Thr Tyr Arg Asp Gly Arg Val Ala Gln Leu Glu Gln Val Tyr Ile Arg
    50                  55                  60

Gly Cys Lys Ile Arg Phe Leu Ile Leu Pro Asp
65                  70                  75

<210> SEQ ID NO 170
<211> LENGTH: 101
<212> TYPE: PRT
<213> ORGANISM: Nostoc ellipsosporum

<400> SEQUENCE: 170

Leu Gly Lys Phe Ser Gln Thr Cys Tyr Asn Ser Ala Ile Gln Gly Ser
1               5                   10                  15

```
-continued

Val Leu Thr Ser Thr Cys Glu Arg Thr Asn Gly Gly Tyr Asn Thr Ser
            20              25              30

Ser Ile Asp Leu Asn Ser Val Ile Glu Asn Val Asp Gly Ser Leu Lys
        35              40              45

Trp Gln Pro Ser Asn Phe Ile Glu Thr Cys Arg Asn Thr Gln Leu Ala
    50              55              60

Gly Ser Ser Glu Leu Ala Ala Glu Cys Lys Thr Arg Ala Gln Gln Phe
65              70              75              80

Val Ser Thr Lys Ile Asn Leu Asp Asp His Ile Ala Asn Ile Asp Gly
            85              90              95

Thr Leu Lys Tyr Glu
            100
```

METHODS OF AB INITIO PREDICTION OF α HELICES, β SHEETS, AND POLYPEPTIDE TERTIARY STRUCTURES

REFERENCE TO GOVERNMENT GRANT

This invention was made with Government support under No. R01 GM52032, awarded by the National Institutes of Health. The Government has certain rights in this invention.

TECHNICAL FIELD

The present invention relates generally to the field of molecular biology. More particularly, the invention relates to novel methods of predicting alpha helical segments, beta-sheets, and the tertiary structure of a polypeptide ab initio, provided with only the amino acid sequence of the polypeptide.

BACKGROUND

Proteins are essential molecules exhibiting complex structural and functional relationships. Biological functionality is defined by the native three-dimensional structure of the protein, which in turn depends on an intricate balance of molecular interactions. It is well known that many proteins fold spontaneously from random disordered states into compact (native) states of unique shape. However, the ability to explain the mechanisms that govern this transformation has not yet been realized. The goal in solving this protein folding problem is to understand this folding process and to predict the three dimensional structure of proteins from their one dimensional amino acid sequence.

Structure prediction of polypeptides and proteins from their amino acid sequences is regarded as a holy grail in the computational chemistry, molecular and structural biology communities. According to the thermodynamic hypothesis, the native structure of a protein in a given environment corresponds to the global minimum free energy of the system. Anfinsen, *Science* 181, 223 (1973). Recent reviews assess the advances made in this area by researchers across several disciplines. Dill, *Prot Sci* 8, 1166 (1999); Koehl and Levitt, *Nature Structural Biology* 6, 108 (1999); Wales and Scheraga, *Science* 285, 1368 (1999). In spite of pioneering contributions and decades of effort, the ab initio prediction of the folded structure of a protein remains a very challenging problem. The current approaches for the structure prediction of polypeptides can be classified as : (i) homology or comparative modeling methods; (ii) fold recognition or threading methods; (iii) ab initio methods that utilize knowledge-based information from structural databases (e.g., secondary and/or tertiary structure restraints); and (iv) ab initio methods without the aid of knowledge-based information.

Knowledge-based ab initio methods exploit information available from protein databases regarding secondary structure, introduce distance constraints, and extract similar fragments from multiple sequence alignments in an attempt to simplify the prediction of the folded three-dimensional protein structure. Contributions to the art include the work reported in Levitt, *J. Mol. Biol.* 170, 723 (1983); Hinds and Levitt, *J. Mol. Biol.* 243, 668 (1994); Ortizet al., *Proc. Natl. Acad. Sci. USA* 95, 1020 (1998a); Skolnick et al., *J. Mol. Biol.* 265, 217 (1997); Simons et al., *Proteins* 34, 82 (1999a); Shortle et al., *Proc. Natl. Acad. Sci. USA* 95, 11158 (1998); Sun et al., *Protein Engineering* 8, 769 (1995); Monge et al., *Proc. Natl. Acad. Sci. USA* 91, 5027 (1994); Monge et al., *J. Mol. Biology* 247, 995 (1995); M. Standley et al., *J Mol Bio* 285, 1691 (1999).

Ab initio methods that are not guided by knowledge-based information represent the most challenging category. Important advances include, among others, Scheraga et al., *J Global Optimization* 15, 235 (1999); Liwo et al., *Proc. Natl. Acad. Sci. USA* 96, 5482 (1999); Lee et al., *Biopolymers* 46, 103 (1998); Srinivasan and Rose, *PNAS* 96, 14258 (1999); Yue and Dill, *Protein Science* 5, 254 (1996); Dill et al., *J. Computational Biology* 4, 227 (1997). A recent assessment of the current status of both types of ab initio protein structure prediction approaches may be found in Orengo et al., *Proteins* Suppl. 3, 149 (1999).

The above methods fail to predict accurately and reliably the tertiary structure of a polypeptide, as determined by lack of agreement with experimental observations of the tertiary structure. Thus, there is a need for more accurate and reliable methods of determining the tertiary structure of polypeptides ab initio.

SUMMARY OF THE INVENTION

The present invention provides the novel ASTRO-FOLD approach for the ab initio prediction of the three dimensional structures of proteins. The four stages of the approach are exemplified in FIG. 1. The first stage involves the identification of helical segments. This aspect of the invention is accomplished by first partitioning the amino acid sequence into oligopeptides, for example, pentapeptides, such that consecutive pentapeptides possess an overlap of four aminoacids. Then, atomistic level modeling is performed using a selected force field. Many force field parameterizations exist for protein systems. In one aspect of the invention, the ECEPP/3 force field, which includes non-bonded, hydrogen-bonding, electrostatic, torsional and disulfide loop-closing terms is employed. Nemethy et al., *J. Phys. Chem.* 96, 6472 (1992). The next steps involve generating an ensemble of low energy conformations, then calculating free energies that include entropic, cavity formation, polarization and ionization contributions for each pentapeptide, and finally the calculation of helix propensities for each residue using equilibrium occupational probabilities of helical clusters.

The partitioning of the amino acid sequence into overlapping oligopeptides is based on the idea that helix nucleation relies on local interactions and positioning within the overall sequence. The explicit consideration of local interactions through overlapping oligopeptides allows for detection of cases in which identical amino acid sequences adopt different conformations in different proteins. See, e.g., Minor and Kim, *Nature* 380, 730 (1996). This is consistent with the observation that local interactions extending beyond the boundaries of the helical segment retain information regarding conformational preferences. See, e.g., Baldwin and Rose, *TIBS* 24, 77 (1999). The partitioning pattern is generalizable and can be extended to heptapeptide, nonapeptide, and even longer systems, such as those equivalent in length to the longest known helical segments. See, e.g., Anfinsen and Scheraga, *Advances In Protein Chemistry* 29, 205 (1975). Other methods have utilized partitioning schemes, but these only provide for discrete states of the central residue of non-overlapping peptides and have not considered the implications of free energy modeling. The overall methodology for the ab initio prediction of helical segments encompasses the following steps:

1. The overlapping pentapeptides are modeled as neutral peptides surrounded by a vacuum environment using the ECEPP/3 force field. An ensemble of low potential energy pentapeptide conformations, along with the global minimum potential energy conformation, is identified using a modification of the αBB global optimization approach [Klepeis and Floudas, *J Chem Phys* 110, 7491 (1999)] and the conformational space annealing approach [Lee et al., *Biopolymers* 46, 103 (1998)]. For the set of unique conformers, Z, determined by removing all duplicate and symmetric minima, including the clustering of any two minima that do not differ by more than 50 degrees for at least one dihedral angle, free energies ($F^{har}_{vac}$) are calculated using the harmonic approximation for vibrational entropy. See Klepeis and Floudas, *J Chem Phys* 110, 7491 (1999).

2. The energy for cavity formation in an aqueous environment is modeled using a solvent accessible surface area expression, $F_{cavity}=\gamma A+b$, wherein A is the surface area of the protein exposed to the solvent. This macroscopic free energy term is based on a fit to experimental free energies of the transfer of alkane molecules into water. The values for the γ and b parameters are taken to be 0.005 kcal/molAA and 0.860 kcal/mol, respectively.

3. For the set of unique conformers, Z, the total free energy is calculated from the expression $$F_{total}=F^{har}_{vac}+F_{cavity}+F_{solv}+F_{ionize},$$

wherein $F_{sol}$ represents the difference in polarization energies caused by the transition from a vacuum to a solvated environment, and $F_{ionize}$ represents the ionization energy. Solvation and ionization free energies are typically calculated through the solution of the nonlinear Poisson Boltzmann equation, using finite difference or multigrid boundary element solution methods. See, e.g., Gilson et al., *J Comp Chem* 9, 327 (1987). Here the finite difference solution of the Poisson Boltzmann equation, as implemented in the DELPHI package, is adopted. Honig and Nicholls, *Science* 268, 11144 (1995).

4. For each oligopeptide, total free energy values ($F_{total}$) are used to evaluate the equilibrium occupational probability for conformers having three central residues within the helical region of the φ-ψ space. Helix propensities for each residue are determined from the average probability of those systems in which the residue constitutes a core position.

In the second stage of tertiary structure prediction, β sheets and disulfide bridges are identified through a novel superstructure-based mathematical framework originally established for chemical process synthesis problems. Floudas, *Nonlinear and mixed-integer optimization* (Oxford University Press, New York, 1995). In this aspect of the invention, two types of superstructure are introduced, both of which emanate from the principle that hydrophobic interactions drive the formation of β structure. The first type, denoted hydrophobic residue-based superstructure, encompasses all potential contacts between pairs of hydrophobic residues (i.e., a contact between two hydrophobic residues may or may not exist) that are not contained in helices (except cystines which are allowed to have cystine-cystine contacts even though they may be in helices). The second type, denoted β strand-based superstructure, includes all possible β strand arrangements of interest (i.e., a β strand may or may not exist) in addition to the potential contacts between hydrophobic residues. The hydrophobic residue-based and β strand-based superstructures are formulated as mathematical models which feature three types of binary variables: (i) representing the existence or nonexistence of contacts between pairs of hydrophobic residues; (ii) denoting the existence or nonexistence of the postulated β strands; and (iii) representing the potential connectivity of the postulated β strands. Several sets of constraints in the model enforce physically legitimate configurations for antiparallel or parallel β strands and disulfide bridges, while the objective function maximizes the total hydrophobic contact energy. The resulting mathematical models are Integer Linear Programming (ILP) problems which not only can be solved to global optimality, but can also provide a rank ordered list of alternate β sheet configurations.

In the hydrophobic residue-based superstructure and its mathematical model, all residues not belonging to helices (except cystines) are first classified as hydrophobic, bridge, turn or other residues. The residues, H, are considered to be hydrophobic: H=Leu, Ile, Val, Phe, Met, Cys, Tyr, Trp; the residues, B, are considered to be bridge: B=Ala, Thr; the residues, T, are considered to be turn: T=Asn, Asp, Gly, Pro, Ser; and the residues, N, are considered to be other: N=Arg, Lys, Glu, Gln, His. The β strand-based superstructure requires the introduction of a protocol for the placement of the H, B, T, and N residues. Each residue is also assigned a position dependent parameter, P(i), which is equal to the position of the hydrophobic residue in the overall sequence and is used extensively to describe allowable contacts between hydrophobic residues. Hydrophobicity parameters, $H_i$, are taken from hydrophobicity scales derived either from experimental transfer free energies or from statistical data. See, e.g. Karplus, *Protein Science* 6, 1302 (1997); Lesser and Rose, *Proteins* 8, 6 (1990). The interaction energy for a potential hydrophobic contact is assumed to be additive, and for cases involving a cystine-cystine contact an additional energy contribution, $H^{add}_{ij}$, is included. The additional cystine-cystine contribution, $H^{add}_{ij}$, is based on the addition of the interaction energy for all hydrophobic residues between the potential disulfide bonding pair, $[(\Sigma_{k,\ P(i)\leq P(k)\leq P(j)}H_k)/(P(j)-P(i))]$. The objective is to maximize the contact energy:

$$\max \sum_i \sum_{j, P(i)+2<P(j)} (H_i + H_j + H^{add}_{ij})y_{ij}$$

where the binary (0–1) variables, $y_{ij}$, represent potential hydrophobic contacts. The maximization is subject to several sets of constraints which define allowable β sheet configurations. For antiparallel β sheets the constraints $$y_{ij}+y_{kl}\leq 1 \forall P(i)+P(j)\neq P(k)+P(l),\ y_{ij}\ \text{OR}\ y_{kl} \notin \{Cys, Cys\}$$

which require that the sum of the contact position parameters must be equal, enforce the formation of symmetric, non-intersecting loops. The constraint is not enforced when the potential contact represents a disulfide bridge. For parallel β sheets the contacts must involve symmetric intersecting loops, which produces the following set of constraints:

$$y_{ij}+y_{kl}\leq 1\ \forall P(k)-P(i)\neq P(j),\ y_{ij}\ \text{OR}\ y_{kl}\notin \{Cys, Cys\}$$

Additional restrictions include: (i) one constraint requiring the formation of at least one contact in which no less than seven residues fall between the contacting residues; (ii) a set of constraints imposing the total number of possible contacts for each residue (initially set to 1 so that each residue may participate in only one contact); and (iii) one inequality constraint to set an upper bound on the number of disulfide bridges.

The third stage of tertiary structure prediction serves as a preparative phase for atomistic-level tertiary structure prediction, and therefore focuses on the determination of pertinent information from the results of the previous two stages. This next aspect of the invention involves the introduction of lower and upper bounds on dihedral angles of residues belonging to predicted helices or β strands, as well as restraints between the $C^\alpha$ atoms for residues of the selected β sheet and disulfide bridge configuration. Furthermore, for segments which are not classified as helices or β strands, free energy calculations for overlapping oligopeptides are conducted to identify tighter bounds on their dihedral angles.

The fourth and final stage of the approach involves the ultimate prediction of the tertiary structure of the full polypeptide sequence. This next aspect of the invention involves the formulation of the problem relying on dihedral angle and atomic distance restraints acquired from the previous stage, as follows:

$$\min_{\varphi} \quad E_{ECEPP/3}$$

$$\text{subject to} \quad E_l^{distance}(\varphi) \leq E_l^{ref} \quad l = 1, \ldots, N_{CON}$$

$$\varphi_i^L \leq \varphi_i \leq \varphi_i^U \quad i = 1, \ldots, N_\varphi$$

wherein $i=1, \ldots, N_{100}$ refers to the set of dihedral angles, $\phi_i$, with $\phi_i^L$ and $\phi_i^U$ and upper bounds on these dihedral angles. The total violations of the $l=1, \ldots, N_{CON}$ distance constraints are controlled by the parameters $E^{ref}_l$. See Klepeis et al., *J Comp Chem* 20, 1354 (1999). To overcome the multiple minima difficulty, the search is conducted using the αBB global optimization approach, which offers a theoretical guarantee of convergence to an ε global minimum for nonlinear optimization problems with twice-differentiable functions. Androulakis et al., *J. Glob. Opt.* 7, 337 (1995); Floudas, *Deterministic Global Optimization: Theory, Methods and Applications* in Nonconvex Optimization and its Applications (Kluwer Academic Publishers, 2000). This global optimization approach effectively brackets the global minimum by developing converging sequences of lower and upper bounds, which are refined by iteratively partitioning the initial domain. Upper bounds correspond to local minima of the original nonconvex problem, while lower bounds belong to the set of solutions of convex lower bounding problems, which are constructed by augmenting the objective and constraint functions by separable quadratic terms. To ensure non-decreasing lower bounds, the prospective region to be bisected is required to contain the infimum of the minima of lower bounds. A non-increasing sequence for the upper bound is maintained by selecting the minimum over all the previously recorded upper bounds. The generation of low energy starting points for constrained minimization is enhanced by introducing torsion angle dynamics [see Güntert et al., *J. Mol. Biol.* 273, 283 (1997)] within the context of the αBB global optimization framework. The αBB has been successfully applied to computational chemistry problems, including microclusters, small acyclic molecules, and isolated and solvated oligopeptides. Floudas, *Deterministic Global Optimization: Theory, Methods and Applications* Nonconvex Optimization and its Applications (Kluwer Academic Publishers, 2000).

An important question regarding the prediction of the native folded state of a protein is how the formation of secondary and tertiary structure proceeds. Two common viewpoints provide competing explanations to this question. The classical opinion regards folding as hierarchic, implying that the process is initiated by rapid formation of secondary structural elements, followed by the slower arrangement of the tertiary fold. The opposing perspective is based on the idea of a hydrophobic collapse, and suggests that tertiary and secondary features form concurrently. The invention bridges the gap between the two viewpoints by introducing a novel ab initio approach for tertiary structure prediction in which helix nucleation is controlled by local interactions, while non local hydrophobic forces drive the formation of β structure. The agreement between the experimental and predicted structures validates the use of the ASTRO-FOLD method for generic tertiary structure prediction of polypeptides.

The ability to predict ab initio the tertiary structure of a polypeptide is a valuable contribution to the art. The methods described herein allow those of skill in the art to study conformations of polypeptides of interest, including their biological functionality, but also to advance the investigation of potential ligands and binding partners, such as receptors, the design of competing binding partners, and the discovery of compounds, such as drugs, which affect the native conformation of the polypeptide so as to modulate or regulate the polypeptide's function.

BRIEF DESCRIPTION OF THE DRAWINGS

FIG. 4 shows potential energy terms in ECEPP/3 force field. $r_{ij}$ refers to the interatomic distance of the atomic pair (ij). $Q_i$ and $Q_j$ are dipole parameters for the respective atoms, in which the dielectric constant of 2 has been incorporated. $F_{ij}$ is set equal to 0.5 for 1–4 interactions and 1.0 for 1–5 and higher interactions. $A_{ij}$, $C_{ij}$, $A_{ij}$ and $B_{ij}$ are nonbonded and hydrogen bonded parameters specific to the atomic pair. $E_{o,k}$ are parameters corresponding to torsional barrier energies for a given dihedral angle. $\theta_k$ represents any dihedral angle. $c_k$ takes the values $-1,1$, and $n_k$ refers to the symmetry type for the particular dihedral angle.

DETAILED DESCRIPTION OF THE INVENTION

Figure 1:
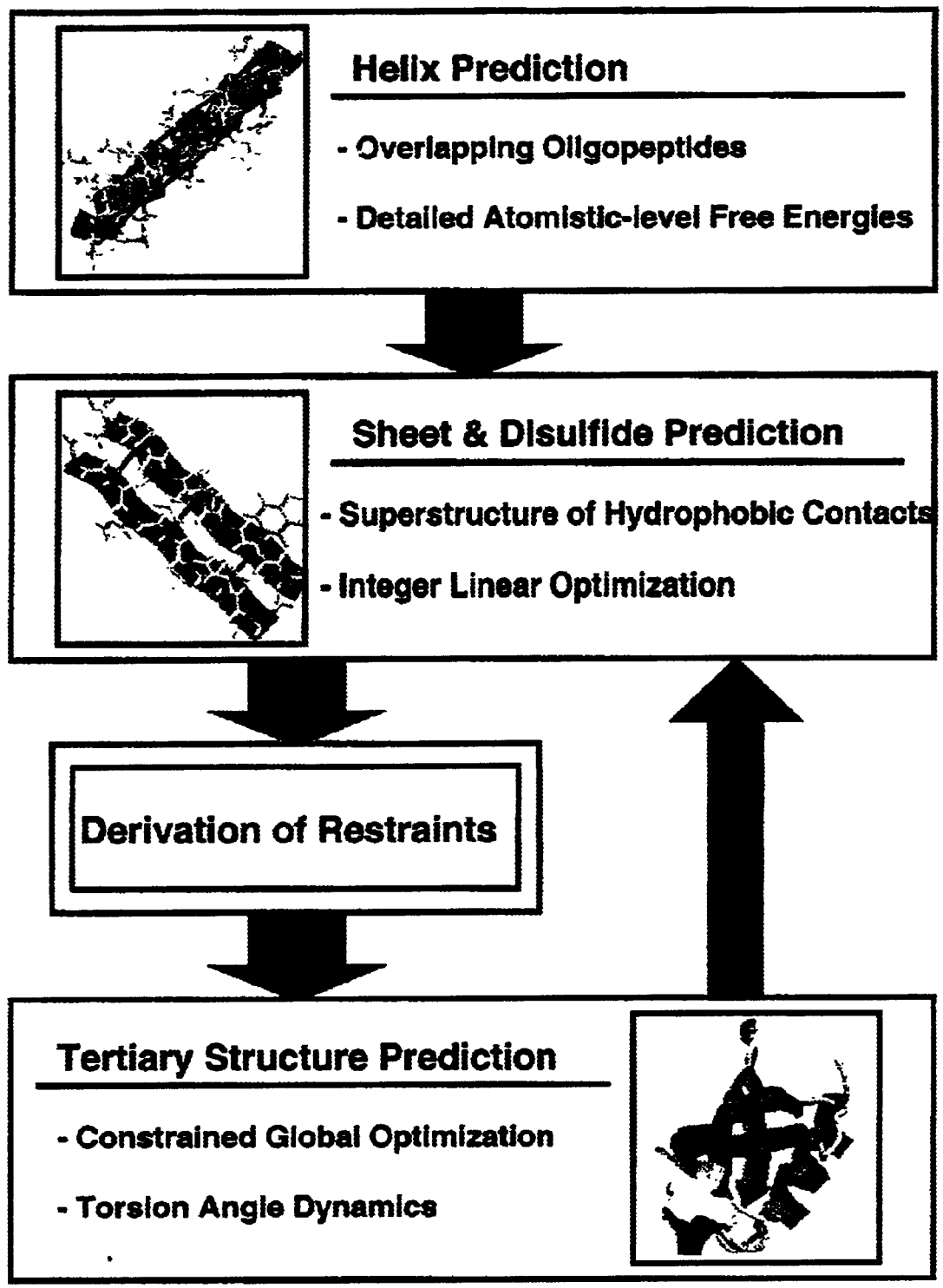
FIG. 1 is an illustrative overall flowchart for the ab initio structure prediction using ASTRO-FOLD. The first stage addresses the prediction of helical segments based on free energy calculations of overlapping oligopeptides. The second stage introduces a superstructure-based framework coupled with integer-linear optimization for the prediction of a rank-ordered list of β sheets and disulfide bridges. The third stage derives lower and upper bounds on the $(\phi,\psi)$ dihedral angles of the secondary structure residues, the distances between pairs of contacts of hydrophobic residues, and the $(\phi,\psi)$ angles of the loop/turn.residues. The fourth stage introduces a constrained formulation for the tertiary structure prediction and its solution via the αBB global optimization approach enhanced by torsion angle dynamics. An iterative loop over the final three stages allows for analysis of multiple β sheet and disulfide bridge configurations.

The practice of the present invention will employ, unless otherwise indicated, conventional methods of chemistry, polymer chemistry, combinatorial chemistry, biochemistry, molecular biology, immunology and pharmacology, within the skill of the art. Such techniques are explained fully in the literature.

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

Inherent to the hierarchical view of protein folding is the dominant role of local forces in determining the formation of secondary structure. These local forces denote those interactions between neighboring residues, rather than nonlocal forces that may arise during tertiary structure formation. In other words, local sequence information should be sufficient to predict native secondary structure if folding is hierarchic. In considering the local prediction of secondary structure elements, such as α-helices, and β-strands and turns, most methods rely on statistical treatments. Munoz and Serrano, *Nat Struct Biol*, 1:399–409, 1994. More recent work has led to the proposal of a physical theory for secondary structure formation based on local interactions and sterics. Srinivasan and Rose, *PNAS*, 96:14258–14263, 1999; Baldwin and Rose, *TIBS*, 24:26–33, 1999; Baldwin and Rose, *TIBS*, 24:77–83, 1999. The basis for this theory hinges on the role of intrinsic propensities for backbone conformations and backbone hydrogen bonding.

The alternative perspective stresses the importance of the hydrophobic collapse rather than local propensities in determining a protein's fold. In this view, hydrophobic forces drive the collapse through the desolvation of side chains. It is believed that these non-local side chain interactions influence the formation of tertiary as well as secondary structural elements. Dill, *Prot Sci*, 8:1166–1180, 1999. In addition, these ideas suggest that simple side chain models of protein folding may be sufficient to predict folding behavior.

For both cases experimental evidence has been produced to support the underlying claims. For example, kinetic studies have shown that elements of secondary structure common to the native fold are able to form before substantial tertiary structure arrangement. The boundaries of helical structure can also be identified through local sequence information, implying that local interactions dominate helix formation. Finally, fragments of longer protein sequences can form native-like folds in the absence of long range interactions. Baldwin, *Biophys Chem*, 55:127–135, 1995. On the other hand, support for non hierarchical folding through a hydrophobic collapse includes experiments showing that protein folds are less affected by mutations on their surfaces than in their hydrophobic cores. Lim and Sauer, *J Mol Biol*, 219:359–376, 1991. In addition, hydrophobic collapse, like secondary structure formation, occurs rapidly in certain cases. Other results, such as the formation of β-sheet folds through α-helical intermediates, imply that secondary units are not preassembled and can be driven by tertiary structure formation.

Simulations of a hydrophobic collapse through side chain models fail to predict the formation of α-helices. Honig and Cohen, *Fold Des*, 1:R17–R20, 1996. This indicates that simplified models for protein folding may not be sufficient because they lack a full structural and energetic description of secondary structure formation. Other methods, such as those based on a statistical mechanical treatment for helix determination, have been somewhat effective, but lack a true physical basis. See, e.g., Munoz and Serrano, *Nat Struct Biol*, 1:399–409, 1994.

The present invention employs the principles of hierarchical folding to develop a method for the prediction of α helices in protein systems. The support for this procedure for α-helix determination is based on observations that native like segments of helical secondary structure form rapidly. The ability for helices to overcome Levinthal's paradox suggests that a helix formation can occur during the earliest stages of protein folding. Such a mechanism for the helix-coil transition is based on local interactions which induce nucleation and propagation of the helix. Honig and Yang, *Adv Prot Chem*, 46:27–58, 1995.

Secondary structure prediction is often an important precursor in tackling the overall protein folding problem, and many methods have been developed in an attempt to accurately predict the location of α helices and β strands. The most successful methods rely on homology modeling or multiple sequence alignments to predict secondary structure using only the amino acid sequence. If the databases of experimental structures contain significantly similar (homologous) sequences to the predicted sequence, then local conformation patterns, such as α helices and β strands, can be predicted with accuracy that in certain cases can exceed 70 percent. However, most protein sequences do not possess known structural homologues, which causes a significant decrease in prediction accuracy. For these cases the natural extension of the comparative modeling approach to fold recognition and threading techniques has shown some success.

For target sequences possessing known folds, the technique of comparative modeling begins with the process of sequence alignment; in other words, the search for homologous proteins. This procedure is practical when sequence identities are greater than 30 percent. Since the goal of sequence alignment is to identify and accurately align segments of related sequences, the use of multiple sequence alignment has been an important development that has led to the ability to better identify sequence variability, insertions and deletions. Niermann et al., *Biol. Chem.*, 368:1087–1088, 1987. The most successful sequence alignment techniques use profiles derived from databases of sequence families. More recently, advanced sequence alignment methods have been based on hidden Markov models and genetic algorithms.

The success of sequence alignment, as measured by the sequence identity score, directly determines the complexity of the homology modeling process. For sequence identities greater than 70–90 percent, the backbone template of the homologous protein provides an accurate model for the target sequence. The only remaining step is to correctly place the side chains of the target sequence onto the backbone of the template sequence. The task becomes more complex as sequence identities decrease to the vicinity of 30 percent. Aligned sequences in this range generally adopt the same fold, however the sequence is dominated by the modeling of loops, which introduces additional challenges.

For target sequences possessing known folds but low sequence identities (less than 30 percent), the applicability of comparative modeling becomes uncertain. In fact, before the sequence can be properly aligned, the question of accurately detecting a remote homologous sequence must be addressed. These complications have led to the development of threading methods, an NP-complete (complexity related to performance of nondeterministic Turing machine in polynomial time) class of problems, in which the target sequence is threaded onto the backbone of the template sequence while evaluating the sequence fitness. Typically, these fitness functions represent environment based, or knowledge based potentials derived from the PDB (Protein Data Bank. Other alternative threading schemes involving one dimensional secondary structure predictions have also been proposed. Although threading methods are much more reliable than traditional alignment techniques, accuracy levels for the correct detection of remote homologues is still below 40 percent. These difficulties are magnified when trying to identify correct alignments and build two and three dimensional models.

When analyzing a target sequence possessing an unknown fold, as is the case for most proteins, homology modeling becomes even more difficult. Since secondary structures can usually be predicted more reliably than other features of protein structure, the major efforts have focused on these one dimensional predictions. Initial attempts in the area of secondary structure prediction were based on examining stereochemical properties and statistics. Many studies have also focused on the development of intrinsic sets of helix propensities to give better α-helix predictions. More recently, the benefits of multiple sequence alignments and increased database information have been instrumental in improving prediction accuracies. Many methods rely on evolutionary information through an analysis of the development of protein families from both sequence and structural databases. Enhancements in secondary structure prediction accuracy using evolutionary concepts have been substantial. For example, an easily implemented and standard statistical method, GOR [Garnier et al., *J. Mol. Biol.*, 120:97–120, 1978.], provides 60 percent accuracy for three state (α, β, coil) secondary structure prediction, with only 10 percent of these residues exhibiting reliability scores comparable to homology modeling for known folds. The PHD method [Rost and Sander, *Protein Eng.*, 6:831–836, 1993], which uses a feed forward neural network trained by back propagation of evolutionary information, provides a sustained prediction accuracy over 70 percent with 45 percent of these residues having acceptable reliability scores. More recent neural network methods such as PSIPRED, have achieved sustained accuracies over 75 percent. Jones, *J. Mol. Biol.*, 292:195–202, 1999; McGuffin et al., *Bioinformatics*, 16:404–405, 2000.

In addition to evolutionary information, other secondary structure prediction methods have exploited database information based on physical property information such as solvent accessibility. For example, reliable predictions of solvent accessibility for conserved and functional regions of the target sequence can be used to identify secondary structure by comparing accessibility patterns derived from database proteins. Methods which attempt to refine the procedure for accessibility based prediction have been developed recently. However, the extension of comparative modeling and fold recognition techniques to two and three dimensions has generally resulted in low accuracy predictions for sequences with unknown folds. Improvements will require the use of enhanced mean force potentials, or the development of more accurate ab initio techniques. The present invention provides an improved ab initio technique for determining helical segments, beta strand regions, and tertiary structures of polypeptides.

I. Prediction of Alpha Helix Segments

Figure 2:
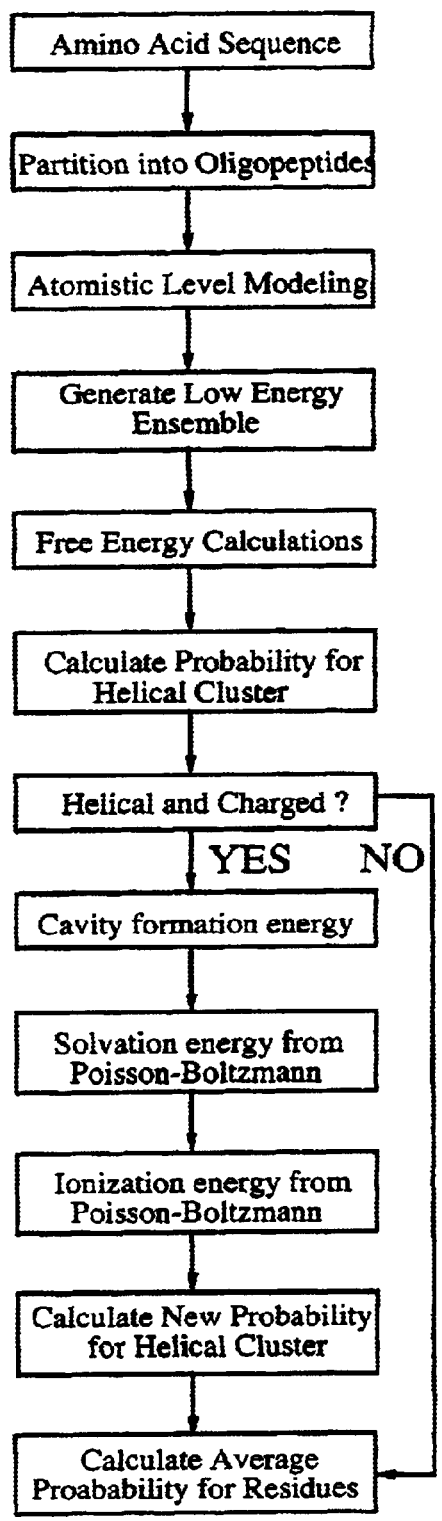
FIG. 2 shows an overall flowchart for the ab initio prediction of helical residues.

In one embodiment of the invention, the approach for the ab initio prediction of helical segments in polypeptides is based on the key ideas of (i) partitioning the sequence of aminoacids into oligopeptides (e.g., pentapeptides, hexapeptides, heptapeptides) such that consecutive oligopeptides have an overlap, for instance, four aminoacids for pentapeptides; (ii) atomistic level modeling of all appropriate interactions for each oligopeptide using the ECEPP/3 force field; (iii) generation of an ensemble of low energy conformations for each oligopeptide; (iv) incorporation of the entropic contributions and free energy calculations for each oligopeptide; (v) calculations of the contributions to free energy due to the formation of cavity for selected oligopeptides; (vi) calculations of the solvation contribution to free energy using the nonlinear Poisson-Boltzmann equation for selected oligopeptides; (vii) calculations of the ionization contribution to free energy using the nonlinear Poisson Boltzmann equation for selected oligopeptides; (viii) calculation of equilibrium occupational probabilities for the helical clusters based on the free energies of the oligopeptides; and (ix) classification of residues as helical according to average propensities for each residue as calculated by the equilibrium occupational probabilities for the helical clusters. A flowchart outlining the main steps of the approach is given in FIG. 2.

A general method has been developed for true ab initio prediction of helix propensity for residues in a given protein sequence. An important component of the approach is that some information regarding helix formation is retained locally, which is evidenced by experimental observations regarding the strong nucleation characteristics of helices. In order to capture local interactions and the unique positioning of each residue in the overall protein, the protein sequence is decomposed into overlapping oligopeptides. The analysis also involves detailed atomistic level modeling, and the refinement of helix propensities according to polarization and ionization energies calculated through the solution of the nonlinear Poisson Boltzmann equation. The end result is the prediction of helical segments according to the average helix propensity assigned to each residue.

A. Partitioning into Oligopeptides

Figure 3:
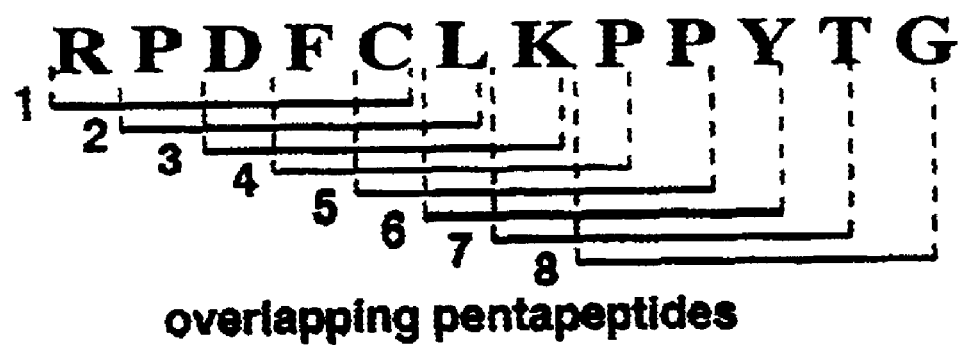
FIG. 3 shows overlapping pentapeptide subsequences for the first 12 residues of BPTI.

The concept of partitioning the aminoacid sequence into overlapping oligopeptides is based on the idea that the formation of helices relies on local interactions and the positioning of each segment within the total protein. The oligopeptide segments may range from segments of about 5 amino acid residues to about 15 amino acid residues. For instance, each consecutive pair of overlapping pentapeptides has four common aminoacids, and for a single chain polypeptide with N residues this translates into an analysis of a total of N-4 pentapeptides. A schematic of these overlapping subsequences for the first 12 residues of BPTI is given in FIG. 3.

Note that the first aminoacid (R) participates only in one pentapeptide (denoted as 1), the second aminoacid (P) participates in two pentapeptides (denoted as 1 and 2), the third aminoacid (D) participates in three pentapeptides (denoted as 1,2,3), the fourth aminoacid (F) participates in four pentapeptides (denoted as 1,2,3,4), while the aminoacids 5–8 (C,L,K,P) each participate in five pentapeptides.

By considering such overlapping oligopeptides and performing free energy calculations based on full atomistic models for each system (Klepeis and Floudas, *J Chem Phys*, 110:7491–7512, 1999), the effect of the local interactions of the neighboring aminoacids is considered explicitly. As a result, situations in which the same segment of identical aminoacid sequence can adopt different conformations in different proteins, as reported by Minor and Kim, *Nature*, 380:730, 1996, can be identified. This is because the local interactions extend beyond the boundaries of the helical segment, and therefore are sufficient to account for such conformational preferences, as suggested by Baldwin and Rose, *TIBS*, 24:77–83, 1999. It should also be noted that a similar partitioning can also result in overlapping heptapeptides or nonapeptides. It is also worth noting that the idea of partitioning the polypeptide into overlapping nonapeptides was first pointed out by Anfinsen and Scheraga, *Advances In Protein Chemistry*, 29:205, 1975, who suggested the minimization with respect to the dihedral angles of the central residue and the consideration of a five state model.

The partitioning of the aminoacid sequence into oligopeptides offers the distinct advantages that (i) the novel free energy calculation method based on deterministic global optimization can be directly applied to a linear sequence of N-4 pentapeptides or N-6 heptapeptides or N-8 nonapeptides, and so forth, and (ii) all oligopeptide free energy calculations can be performed in parallel, where N is the number of aminoacids in the single chain polypeptide under study.

B. Atomistic Modeling

The prediction of α-helices relies on detailed atomistic level modeling of the protein system. In one embodiment of the invention, this modeling is based on the ECEPP/3 semi-empirical force field model, although other general all atom force field models could be employed. For this force field, it is assumed that the covalent bond lengths and bond angles are fixed at their equilibrium values, so that the conformation is only a function of the independent torsional angles of the system. The total force field energy, $E_{forcefield}$, is calculated as the sum of electrostatic, nonbonded, hydrogen bonded, and torsional contributions. The main energy contributions (electrostatic, nonbonded, hydrogen bonded) are computed as the sum of terms for each atom pair (i,j) whose interatomic distance is a function of at least one dihedral angle. The general potential energy terms of ECEPP/3 are shown in FIG. 4, while the development of the appropriate parameters is discussed and reported elsewhere. Némethy et al., 10. *J. Phys. Chem.*, 96:6472, 1992.

C. Ensembles of Low Energy Conformers

Locating the global minimum potential energy conformation is not sufficient because Anfinsen's thermodynamic hypothesis requires the minimization of the conformational free energy. Specifically, potential energy minimization neglects the entropic contributions to the stability of the molecule. An approximation to these entropic contributions can be developed by using information about low energy conformations. That is, once a sufficient ensemble of low energy minima has been identified, a statistical analysis can be used to estimate the relative entropic contributions, and thus the relative free energy, for each conformation in the ensemble. A variety of methods have been used to find such stationary points on potential energy surfaces. For example, periodic quenching during a Monte Carlo or molecular dynamics trajectory can be used to identify local minima. Stillinger and Weber, *J. Stat. Phys.*, 52:1429–1445, 1988. In this work two algorithms are advocated for generating low energy ensembles for pentapeptide sequences. The first is based on modifications of a deterministic branch and bound algorithm, αBB. The second, conformation space annealing (CSA), which does not provide the deterministic guarantees of the αBB, is based on the combination of genetic algorithms and simulated annealing. Lee et al., *J Comp Chem*, 18:1222–1232, 1997.

Our previous work has shown that the generation of ensembles of low energy conformers is possible through algorithmic modifications of the general αBB procedure. Klepeis and Floudas, *J Chem Phys*, 110:7491–7512, 1999. The original implementation of the deterministic αBB global optimization algorithm requires the minimization of a convex lower bounding function in each domain. The unique solution for each lower bounding minimum can then used as a starting point for the minimization (or function evaluation) of the original energy function in the current domain. In the case of local minimization, each partitioned region provides a single minimum energy conformation as the algorithm proceeds. Using this information, along with the global minimum energy conformation, a list of low energy conformers can be constructed.

Figure 5:
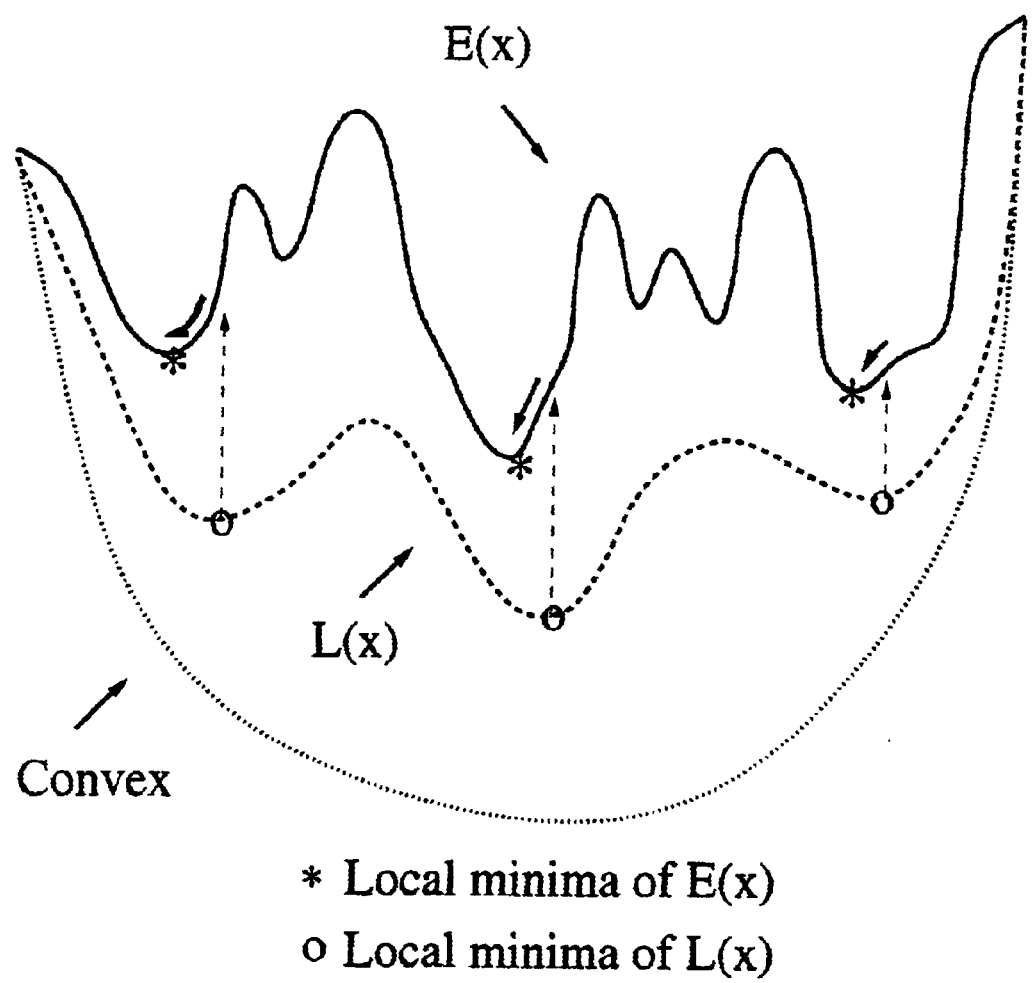
FIG. 5 shows the use of multiple lower bound minima to find low energy conformers of the upper bounding function, as derived from the concepts of the αBB deterministic global optimization algorithm.

However, this approach does not take advantage of all the information provided by the lower bounding functions. Rigorously, these functions posses a single minimum in each subdomain. Since the choice of α (convexity parameter) affects the convexity of the lower bounding functions, the α values can be modified to ensure a certain nonconvexity in these functions. In this case, the lower bounding functions possess multiple minima, and these functions can be minimized several times in each domain. In addition, since the lower bounding functions smooth the original energy hypersurface, the location of these multiple minima provide information on the location of low energy minima for the upper bounding function. Therefore, by using the location of the minima of the lower bounding function as starting points for local minimization of the upper bounding function, an improved set of low energy conformations can be identified. As before, these conformations are also localized in those domains with low energy as the subdomains decrease in size. This energy directed approach (EDA) is represented schematically in FIG. 5.

The conformational space annealing method (CSA) relies on stochastic measures to converge to a cluster that should include the global minimum energy conformation. Lee et al., *J Comp Chem*, 18:1222–1232, 1997. Through the use of genetic algorithm updates, an ensemble of low energy minima is also produced. The first step involves the generation of a set of bank conformations, which should initially be distributed randomly throughout the conformation space. Each conformation in the bank is regarded as a representative of a group of local minima within a certain distance in conformational space. The distance measure between conformations i and j is the root mean square deviation with respect to the dihedral angles:

$$D_{ij} = \sqrt{\frac{1}{N_\theta} \sum_{i=1}^{N_\theta} (\theta_i - \theta_j)^2} \tag{1}$$

As the algorithm proceeds the parameter $D_{cut}$, which defines the size of a cluster in conformation space, is slowly annealed from the original bank distribution value to an arbitrarily small value.

The group representatives in the bank are updated by generating additional conformations. The generation of these conformations is based on the concepts of a genetic algorithm, so that fragments of conformation i are replaced by randomly chosen conformations from the rest of the bank. The updating rules include replacing individual dihedral angles, randomly chosen groups of correlated (small number) dihedral angles, and connected groups (large number) of dihedral angles. The newly generated conformations are minimized and compared to the set of bank conformations. If the bank conformation closest in conformational space to the new conformation exhibits a value of $D_{ij} < D_{cut}$, the bank conformation is replaced by the new conformation if the new conformation provides a lower energy value. However, if $D_{ij} > D_{cut}$ for all conformations in the bank, the new conformation defines a new cluster which will enter the bank if it provides an energy lower than the highest energy representative in the bank. In this way the number of bank conformations remains constant. The termination criteria is heuristic and is related to the total number of minimizations.

D. Free Energy and Entropic Calculations

In another embodiment of the invention, the analysis of the pentapeptides is based on a procedure to identify the free energy probability of having the three central residues of the pentapeptide within the helical region of the φ-ψ space. This requires the incorporation of entropic effects to calculate free energy probabilities of individual metastable states of the system. In particular, a strict interpretation of Anfinsen's thermodynamic hypothesis requires the global minimization of the conformational free energy to predict the native structure of a protein. In practice, however, most protein models include only potential and solvation effects. One reason for this neglect of including entropic effects is that a rigorous free energy model requires infinite sampling to associate accurate statistical weights with each microstate.

Other approximate calculations exist for estimating these statistical weights (and thus entropic effects). The most simplistic model would rely on only the Boltzmann weight associated with each microstate. A more sophisticated approximation, known as the harmonic approximation, utilizes second derivative information to characterize the basin of attraction. More complex schemes try to mimic the anharmonic trajectory along the energy surface. These quasi-harmonic approximations generally require the use of MC/MD simulations.

In one embodiment, entropic effects are included via the harmonic approximation. Flory, *Macromolecules*, 7(3):381–392, 1974; Go and Scheraga, *J. Chem. Phys.*, 51(11):4751–4767, 1969; Go and Scheraga, *Macromolecules*, 9(4):535–542, 1976. The development of this model can be understood physically by first considering the partition function for the system:

$$Z = \exp^{-[(E-TS)/k_B T]} = \exp^{-[E/(k_B T)]} \exp[S/(k_B)] \tag{2}$$

In Equation 2 the partition function is the product of the Boltzmann ($\exp[-E/k_B T]$) factor and the number of states available to the system ($\exp[S/k_B]$). At a given stationary point, the harmonic approximation is equivalent to:

$$E(\theta) = E(\theta_\gamma) + \tfrac{1}{2}(\theta - \theta_\gamma) H(\theta_\gamma)(\theta - \theta_\gamma) \quad (3)$$

Here $\gamma$ identifies the stationary point, and the stationarity condition ($\nabla E(\theta_\gamma) = 0$) is used to eliminate the gradient term. In this way, each basin of attraction is characterized by properties of its corresponding minima, which include the local minimum energy value, $E(\theta_\gamma)$, and the convexity (Hessian) information around the local minimum, $H(\theta_\gamma)$. An analogous representation of this system is $N_{74}$ independent harmonic oscillators, each with its own characteristic vibrational frequency. The minimum can then be characterized by the occupation of each normal mode.

To develop an expression for the entropic effect, Equation 3 can be substituted into Equation 2. By summing over all energy states, the partition function becomes:

$$Z_\gamma^{har} = \exp^{-[E(\theta_\gamma)/(k_B T)]} f(T) \prod_i^{N_\theta} \frac{1}{\lambda_i} \quad (4)$$

In Equation 4, $f(T)$ is a function dependent only on temperature, while $\lambda_i$ represent the eigenvalues of $H(\theta_\gamma)$. Comparison of Equations 4 and 2 implies that:

$$\exp^{[S/k_B]} \propto \prod_i^{N_\theta} \frac{1}{\lambda_i} \quad (5)$$

Equation 5 can be rewritten in terms of the harmonic entropic contribution, $S_\gamma^{har}$:

$$S_\gamma^{har} \propto -k_B \ln[\text{Det}(H(\theta_\gamma))] \quad (6)$$

A more rigorous derivation of the harmonic approximation leads to the following expression for the harmonic entropy:

$$S_\gamma^{har} \propto -\frac{k_B}{2} \ln[\text{Det}(H(\theta_\gamma))] \quad (7)$$

This can be used to calculate relative free energies via the following equation:

$$F_\gamma^{har} = E(\theta_\gamma) + \frac{k_B T}{2} \ln[\text{Det}(H(\theta_\gamma))] \quad (8)$$

Finally, each microstate can be assigned a statistical weight ($p^{har}_\gamma$) by considering the ratio of the partition function for that microstate ($Z^{har}_\gamma$) to the total partition function:

$$p_\gamma^{har} = \frac{[\text{Det}(H(\theta_\gamma))]^{-1/2} \exp[-E(\theta_\gamma)/k_B T]}{\sum_{i=1}^{N_\gamma} [\text{Det}(H(\theta_\gamma))]^{-1/2} \exp[-E(\theta_\gamma)/k_B T]} \quad (9)$$

To develop a meaningful comparison of relative free energies, the total partition function (denominator of Equation 9) must include an adequate ensemble of low-energy local minima, as well as the global minimum energy conformation. Therefore, efficient methods for identifying low energy ensembles, as outlined in the previous section, must be employed. It should also be noted that the harmonic approximation does not require the explicit inclusion of a contribution based on the density of states because each local minimizer is accounted for only once (in contrast to counting methods).

Relative free energies can also be calculated for clusters of low energy conformers. This analysis is useful because it is difficult to capture the true accessibility of individual structures based on a point-wise approximation of entropic effects. That is, the harmonic free energy approximation does not provide a continuous free energy landscape. Typically, structures are clustered by calculating and comparing root mean squared deviations. In the case of determining a helical structure, a conformer is said to belong to the α-helical cluster if the torsional angles of three central residues belong to the α-helical region of the φ-ψ space (denoted as AAA). The relative free energy of the α-helical cluster can be calculated by the following equation:

$$F_{AAA} = -k_B T \ln \sum_{i \in AAA} p_i^{har} \quad (10)$$

In Equation 10 the individual $p_i^{har}$, which refers to the statistical weight based on the harmonic approximation, are summed for the set of conformations belonging to the AAA cluster. These individual probabilities are calculated by normalizing each probability with respect to the overall probability at a given temperature:

$$p_i^{har} = \frac{\exp[-\beta(F_o^{har} - F_i^{har})]}{\sum_j \exp[-\beta(F_o^{har} - F_j^{har})]} \quad (11)$$

A reference free energy, $F_o^{har}$, is used to normalize the probabilities at each temperature point. All free energies, $F_o^{har}$, $F_i^{har}$ and $F_j^{har}$, refer to the harmonic approximation of the free energy as calculated using Equation 8. The denominator, which represents the total probability at a given temperature, is calculated by summing over the set of all conformers.

E. Electrostatic Contributions to Free Energy

Initially, in an embodiment of the invention, the overlapping pentapeptides are modeled as neutral peptides surrounded by a vacuum environment using the ECEPP/3 force field. The incorporation of solvation effects requires additional energetic modeling, as well as considering the role of ionizable side chains. These contributions can be included through explicit or continuum based hydration models.

Explicit methods include solvation effects by actually surrounding the peptide with solvent molecules. Energetic evaluations require the calculation of both solvent-peptide and solvent-solvent interactions. Although these methods are conceptually simple, explicit inclusion of solvent molecules greatly increases the computational time needed to simulate the peptide system. Therefore, most simulations of this type are limited to local conformational searches.

Continuum models use a simplified representation of the solvent environment by neglecting the molecular nature of the water molecules. Many models estimate free energies of solvation as a function of geometric quantities, such as surface areas and volumes. More rigorous calculations of solvation free energies include electrostatic continuum models, which rely on numerical solutions to the Poisson-Boltzmann equation, and from which dielectric and ionic strength effects are obtained. Honig et al., *J. Phys. Chem.*, 97:1101–1109, 1993.

In this work, solvation and ionization free energies are calculated through the solution of the nonlinear Poisson Boltzmann equation, for which both finite difference and multigrid boundary element solution methods are available. Gilson et al., *J Comp Chem*, 18:569–583, 1997. In particular, the finite difference solution of the Poisson Boltzmann equation as implemented in the DELPHI package is adopted. Honig and Nicholls, *Science*, 268:11144–1149, 1995; Gilson and Honig, *Proteins*, 4:7, 1988. In addition, the approach includes a procedure for effectively evaluating both the solvation and ionization free equilibria of the peptide conformations. Ripoll et al., *J Mol Bio*, 264:770–783, 1996; Yang et al., *Proteins*, 15:252–265, 1993. The resulting total free energies can then be used to identify equilibrium occupational probabilities for the α-helical clusters.

In one embodiment, the overall methodology encompasses the following steps:

1. Using the ECEPP/3 forcefield, an ensemble of low potential energy oligopeptide (e.g., pentapeptide) conformations, along with the global minimum potential energy conformation, are identified using deterministic global optimization based techniques.
2. Determine a set of unique conformers (Z) by removing all duplicate and symmetric minima, as well as those that do not differ by more than 50 degrees for at least one dihedral angle (disregarding the first and last backbone dihedral angles and the last dihedral angle in each side chain).
3. For the set Z calculate the vibrational entropic component using the harmonic approximation.
4. Model cavity formation in an aqueous environment using a solvent accessible surface area correlation:

$$F_{cavity} = \gamma A_{sa} + b \tag{12}$$

This macroscopic free energy term is based on a fit to the experimental free energy of transfer of alkane molecules into water. The values for the γ and b parameters are taken to be 0.005 kcal/mol Å and 0.860 kcal/mol, respectively.

5. Rank the set (Z) according to the energies given by $(F^{har}_{vac} + F_{cavity})$.
6. For a subset of conformations belonging to (Z) calculate the total energy according to:

$$F_{total} = F^{har}_{vac} + F_{cavity} + F_{solv} + F_{ionize} \tag{13}$$

Here $F_{solv}$ represents the difference in the polarization energies when moving from a vacuum to an aqueous environments, and $F_{ionization}$ represents the ionization energy (see below). The thermodynamic process that captures this transition is given in FIG. 6.

7. $F_{total}$ is subsequently used to calculate equilibrium occupational probabilities of the α-helical cluster.

F. Solvation Free Energy

Calculating the polarization of the environment as an aqueous phase is based on the difference between electrostatic polarization free energies of the peptide in the vacuum and water environments. The change in going from a vacuum to aqueous environment is given by:

$$F_{solv} = F_{polar}(\epsilon=80) - F_{polar}(\epsilon=1) \tag{14}$$

This involves finding the induced surface charge (solving the Poisson-Boltzmann equation) for two systems in which the only difference is the dielectric constant (ε) of the surrounding medium; that is 80 and 1 for the aqueous and vacuum phases, respectively.

Finding $F_{polar}$, which corresponds to the reaction field energy, requires solving the Poisson-Boltzmann equation when the neutral protein (zero ionization) is in the aqueous and vacuum phases. The reaction field energy is determined by calculating the induced surface charge at the surface of the molecule (due to point charges) and then summing the potential at every charge:

$$F_{polar} = \frac{1}{2} \sum_i \sum_s \frac{q_i \sigma_s}{|r_i - r_s|} \tag{15}$$

Reaction field energies can be obtained as a special application of the solution of the Poisson-Boltzmann equation. In particular, the distribution of charges and dielectric boundaries is first used to solve the Poisson-Boltzmann equation through finite difference for all points of a three-dimensional grid. This provides a potential at each grid point. In order to calculate the surface charge density, the proximal grid point potentials are combined for a patch of the constructed Conolly surface. The reaction field energy is calculated by determining the effect of the charge density at each surface patch for each charge point.

G. Ionization Free Energy

For ionizable residues additional calculations must be made for the ionization of these groups in the aqueous phase at a given pH. The determination of this quantity depends on the calculation of the partition function for single or multiple titration sites:

$$F_{ionize}(\text{pH}) = kT \ln Z \tag{16}$$

The partition function includes contributions from all $2^N$ ionization states of the system, where N is the number of ionizable groups:

$$Z = \sum_{i=1}^{2^N} \exp[-\Delta G_i / kT] \tag{17}$$

The free energy of the ith state is given by:

$$\Delta G_i = \sum_{j=1}^{N} \left( x_j \, 2.303 \, kT(\text{pH} - pK_j) + \delta_j \sum_{1 \leq k < j} \delta_k \Delta G_{jk} \right) \tag{18}$$

Here $x_j$ is the charge on the group in the ith state, and δ parameters are binary indicators (i.e., 0 when the group is neutral and 1 when the group is charged). $pK_j$ is the intrinsic $pK_a$ for the jth group, and pH is the current pH value. $\Delta G_{jk}$ represent coupled (multiple site) terms.

Intrinsic $pK_a$ values are obtained by looking at the difference of ionizing the protein in the protein environment and in an isolated aqueous phase:

$$pK_j = pK_j^o - \delta_j \Delta \Delta G_j / 2.303 kT \tag{19}$$

Here $\gamma_j$ is equal to −1 or +1 for acidic or basic ionizable groups, respectively. The $\Delta\Delta G_j$ term is easily related to the pK shift ($\Delta pK_j$) by the following:

$$\Delta pK_j = \frac{\Delta \Delta G_j}{\gamma_j 2.303 \, kT} \tag{20}$$

The thermodynamic cycle for $\Delta\Delta G_j$ involves the introduction of the ionizable group into the protein system and the difference in free energy when going between the neutral and protonated form of that group.

Examination of the thermodynamic cycle provides the following decomposition for $\Delta\Delta G_j$:

$$\frac{\Delta\Delta G_j}{\gamma_j} = (\Delta G_j(PS_i^+/S_i^+) - \Delta G_j(PS_i^o/S_1^o)) \qquad (21)$$

$\Delta G_j$ ($PS_i^+/S_i^+$) represents the change in free energy when moving the (ionized) ionizable group from an isolated aqueous environment into the protein environment. $\Delta G_j$ ($PS_i^o/S_i^o$) represents the same transition but for the neutral form of the ionizable group.

The individual $\Delta G_j$ terms can be further decomposed:

$$\Delta G_j = \Delta G_j^{rxn\ field} + \Delta G_j^{perm\ dipole} \qquad (22)$$

The first term, $\Delta G_j^{rxn\ field}$ refers to the reaction field effects, that is, those effects that arise due to the dielectric continuum nature of the system. For example, $\Delta G_j^{rxn\ field}$ ($PS_i^+/S_i^+$) is the difference in reaction field energy for group j in state i when changing the dielectric continuum from the isolated aqueous state ($\epsilon=80$ only) to that of the protein environment ($\epsilon=2$ in some regions). More specifically, $\Delta G_j^{rxn\ field}$ captures the change in free energy due to the reduced exposure to water. Since we are concerned with the effect on the ionizable group j, the rest of the protein carries zero partial atomic charges. See FIG. 7.

Figure 7:
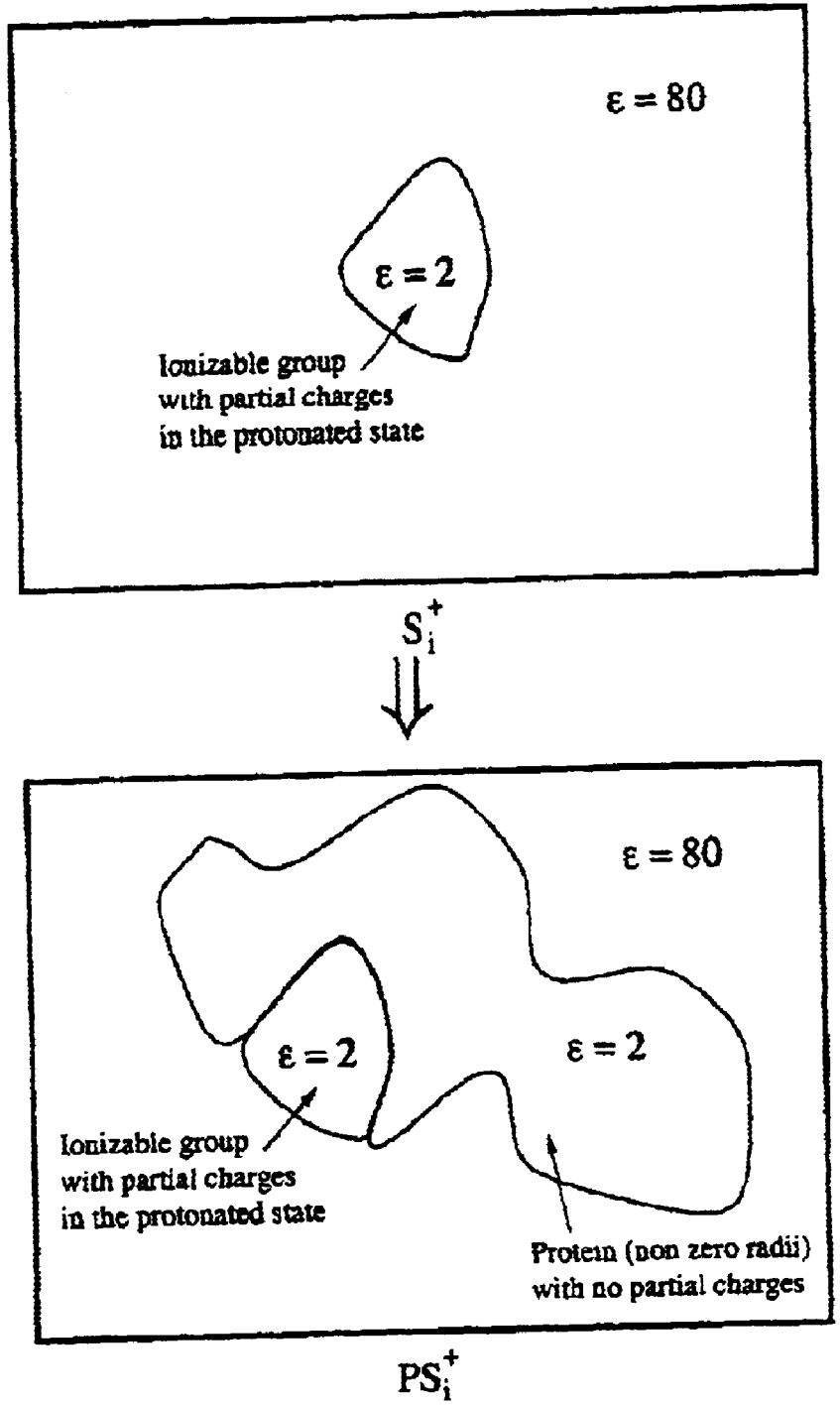
FIG. 7 shows $\Delta G_j^{rxn\ field}$ ($PS_i^+/S_1^+$), the difference in reaction field energy for the ionized form of group j in state i when changing the dielectric continuum.

In order to calculate the change in reaction field energy, $\Delta G_j^{rxn\ field}$ ($PS_i^+/S_i^+$), the Poisson-Bo equation is solved for both systems shown in FIG. 7 to get the reaction field potential map $\phi^{rxn\ field}$ ($PS_i^+$) and $\phi^{rxn\ field}$ ($S_i^+$). This data can be used to map the surface charge distribution on the boundary between the different dielectric environments, that is, $\sigma(PS_i^+)$ and $\sigma(S_i^+)$, respectively. By replacing the surface integral with the appropriate summation, the change in reaction field energy becomes:

$$\Delta G_j^{rxn\ field}(PS_i^+/S_i^+) = \frac{1}{2}\left[\sum_{s(PS_i^+)}\sum_{j+}\frac{q_{j+}\sigma_s(PS_i^+)}{|r_{j+}-r_s|} - \sum_{s(S_i^+)}\sum_{j+}\frac{q_{j+}\sigma_s(S_i^+)}{|r_{j+}-r_s|}\right]$$

In this equation the set j+ refers to the set of partial atomic charge points (with charges $q_{j+}$) of the protonated ionizable group. The set of surface points are denoted as $s(PS_i^+)$ and $s(S_i^+)$ for the isolated and protein environments, respectively. The quantity $|r_{j+}-r_s|$ is the magnitude of the distance between the points defined by sets j+ and s.

Figure 8:
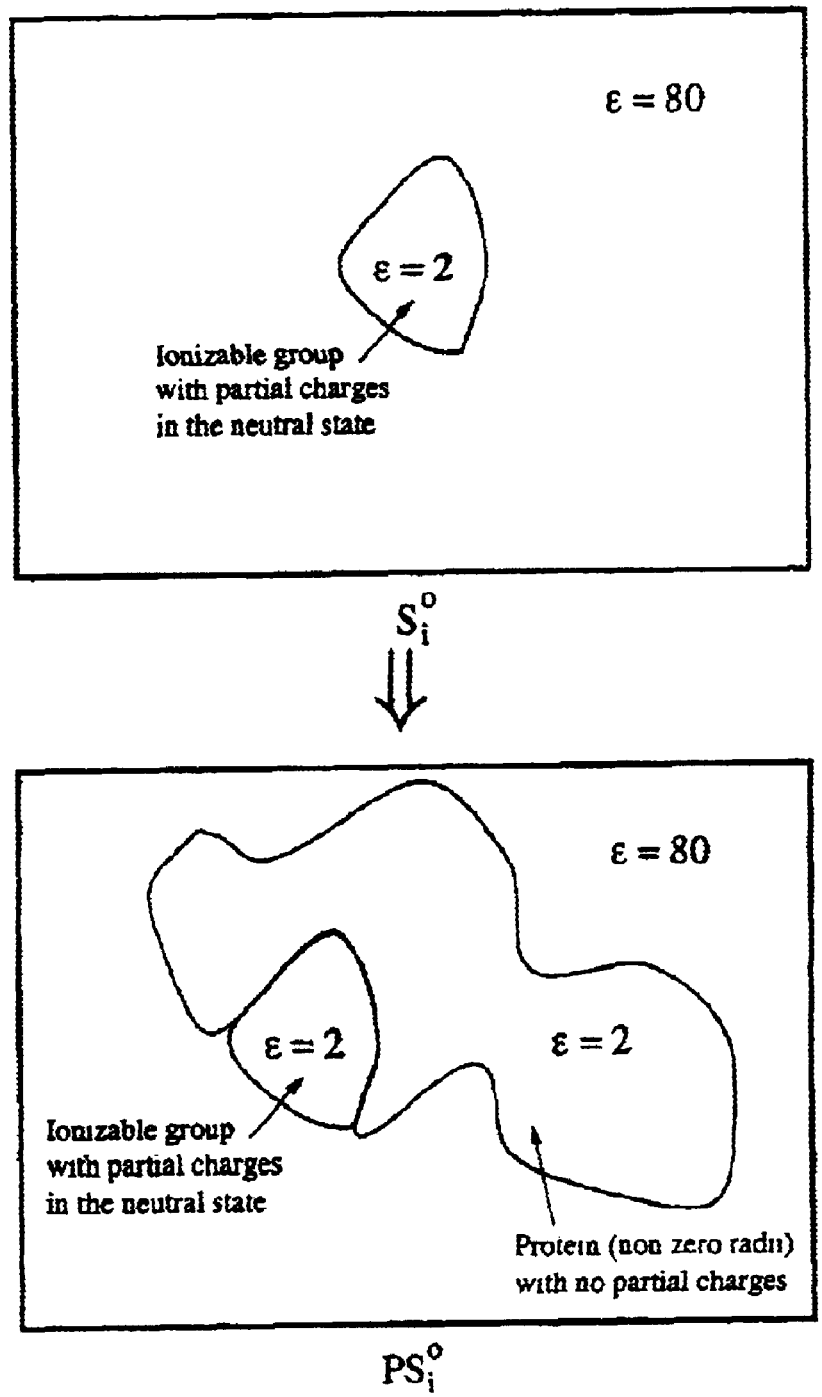
FIG. 8 shows $\Delta G_j^{rxfn\ field}$ ($PS_i^\circ/S_1^\circ$), the difference in reaction field energy for the neutral form of group j in state i when changing the dielectric continuum.

A similar set of equations can be derived for the neutral form of the ionizable group. The systems are shown schematically in FIG. 8. $\Delta G_j^{rxn\ field}$ ($PS_i^o/S_i^+$) can be calculated from the following equation:

$$\Delta G_j^{rxn\ field}(PS_i^o/S_i^o) = \frac{1}{2}\left[\sum_{s(PS_i^o)}\sum_{jo}\frac{q_{jo}\sigma_s(PS_i^o)}{|r_{jo}-r_s|} - \sum_{s(S_i^o)}\sum_{jo}\frac{q_{jo}\sigma_s(S_i^o)}{|r_{jo}-r_s|}\right]$$

The final contribution to $\Delta\Delta G_j$ is based on the difference in potential forces on the ionizable group which arise from permanent dipoles of the entire system. Rather than consider these term separately, the overall dipole change can be written as:

$$\Delta\Delta G_j^{perm\ dipole} = \Delta G_j^{perm\ dipole}(PS_i/S_i^+) - \Delta G_j^{perm\ dipole}(PS_o^+S^{o+}) \qquad (23)$$

In the isolated systems, ($S_i^+$ and $S_i^o$), permanent dipole effects are not present. That is, the ionizable group is only surrounded by a uniform dielectric continuum with $\epsilon=80$ and no permanent dipoles or ions are present. Therefore, $\Delta\Delta G_j^{perm\ dipole}$ collapses to:

$$\Delta\Delta G_j^{perm\ dipole} = \Delta G_j^{perm\ dipole}(PS_i^+/PS_i^o) \qquad (24)$$

Figure 9:
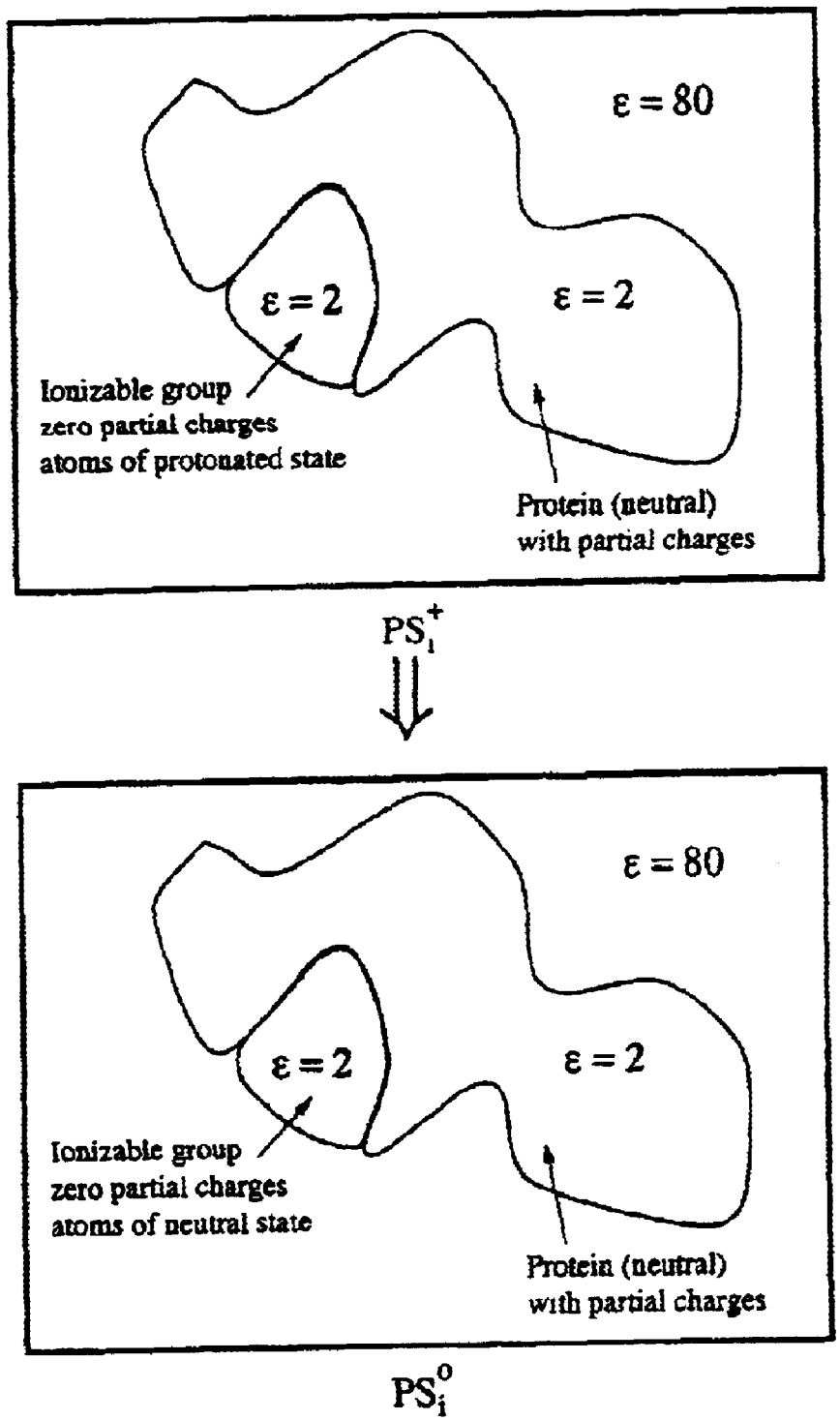
FIG. 9 shows $\Delta G_j^{perm\ dipole}$ ($PS_i^+/PS_i^\circ$), the difference in permanent dipole energy for group j when changing from the neutral to the ionized state i.

The calculation of this quantity requires the solution of Poisson-Boltzmann equation for two systems. For the $PS_i^+$ system, the potential force ($\phi^{perm\ dipole}_{j+}(PS_i^+)$) due to the protein dipole is calculated at the atomic centers of the protonated ionizable group (set j+). For the $PS_i^o$ system, these forces ($\phi^{perm\ dipole}_{jo}(PS_i^o)$) are determined at the atomic centers (set jo) of the neutral form of the ionizable group. A schematic of these systems is shown in FIG. 9.

The final expression for $\Delta G_j^{perm\ dipole}$ ($PS_i^+/PS_i^o$) is based on the sum of the effective potential at the atomic charge centers:

$$\Delta G_j^{perm\ dipole}(PS_i^+/PS_i^o) = \qquad (25)$$
$$\sum_{j+} q_{j+}\varphi_{j+}^{perm\ dipole}(PS_i^+) - \sum_{jo} q_{jo}\varphi_{jo}^{perm\ dipole}(PS_i^o)$$

The final step in treating multiple titration sites is the calculation of $\Delta G_{jk}$ terms. This term represents an energetic adjustment due to the permanent dipole contributions between each pair of titratable groups. In order to isolate the contributions to only those between the ionizable groups, the remaining protein is treated as uncharged. The expression for $\Delta G_{jk}$ can decomposed as:

$$\Delta G_{jk} = \Delta G_{jk}(PS_i^{j+,k+}) + \Delta G_{jk}(PS_i^{jo,ko}) - \Delta G_{jk}(PS_i^{j+,ko}) - \Delta G_{jk}(PS_1^{jo,k+}) \qquad (26)$$

In total, four separate systems must be considered. The first term represents the dipole effects between the charged forms of both groups j and k. The remaining quantities, which correspond to combinations of the neutral and charged forms of groups j and k, are necessary to correct the approximations made when calculating the energies of single titration groups.

Permanent dipole calculations require the solution of the Poisson-Boltzmann equation for a distribution of permanent point charges. The solution provides the induced potential at all grid points, which can be used to calculate the effects at a subset of grid points (point charges).

H. Probabilities of α Helix Formation

The goal and final step of the approach is to classify the individual residues in the overall sequence as helical or non-helical. In the case of considering overlapping pentapeptides, for each residue, excluding the first and last three residues, this classification is based on information obtained from the three pentapeptides for which the residue in question maintains one of the three central positions. As a result, the combined effects of seven residues are accounted for when determining the helical propensity of each individual residue. For each residue, the average probability of being in an helical conformation is defined by the average of the AAA probability for the aforementioned three pentapeptides. The individual AAA probability ($p_{AAA}$) for each pentapeptide is equivalent to the summation term shown in the following equation.

$$p_{AAA} = \sum_{i \in AAA} p_i^{har} \qquad (27)$$

The individual probabilities are calculated according to Equation 11, which depends on the total free energy of the system. For the case of pentapeptides without any ionizable side groups or low helical probabilities ($p_{AAA}$), the free energy is based on the in vacuo calculations. However, the free energy includes detailed solvation and ionization energies for those pentapeptides possessing ionizable side groups and high initial helical probabilities. A residue is defined as helical if the combined helical probabilities ($p_{AAA}$) of the three pentapeptides exceed an average of about 90 percent.

II. Prediction of β-strands, β-sheets, and Disulfide Bridges

In one embodiment of the present invention, a simplified model is developed according to residue properties, including hydrophobic propensities, which can be derived from experimental, statistical or purely computational information. Residue classifications are used to formulate a problem to predict the formation of ordered structural features, such as parallel and antiparallel β sheets. This formulation results in a set of integer linear programming (ILP) problems, which can be solved to global optimality to identify the optimal set of hydrophobic contacts. Solutions to these (ILP) problems represent potential β sheet configurations for the overall protein. The formation of disulfide bonding pairs can be identified within the context of the (ILP) model.

Figure 10:
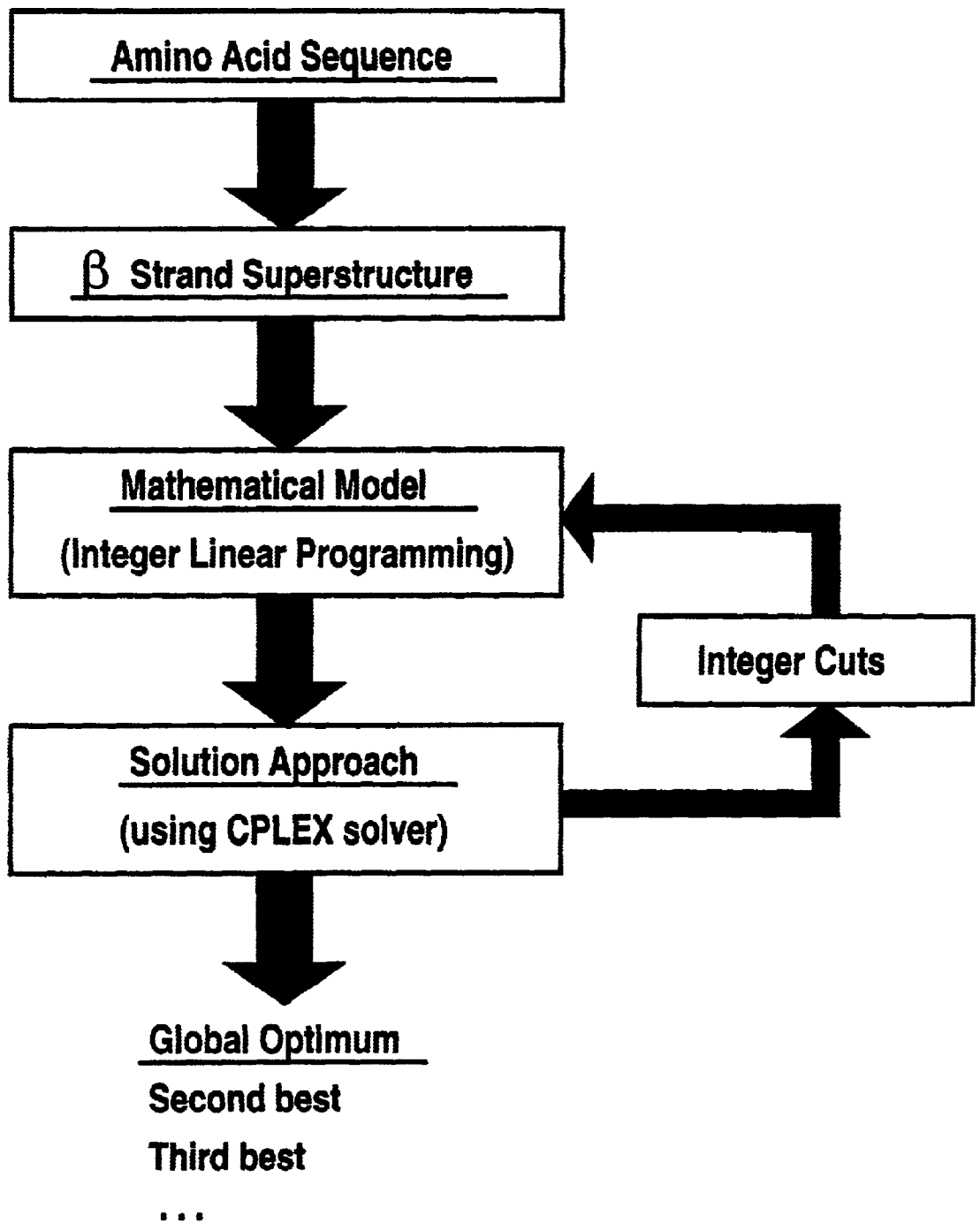
FIG. 10 shows a framework for prediction of β-sheets conformations.

The approach for the prediction of antiparallel β-sheets, parallel β-sheets and disulfide bridges borrows key concepts from a mathematical framework developed in the area of process synthesis of chemical systems (see, e.g., Floudas, *Nonlinear and mixed-integer optimization*. Oxford University Press, New York, 1995.), and it is illustrated in FIG. 10.

The first component is the postulation of a β-strand superstructure that encompasses all alternative β-strand arrangements of interest. It is important to emphasize that the superstructure may include more β-strands than needed. That is, it may postulate the existence of a β-strand which may eventually not be selected to be a β strand.

The second component involves the development of a single mathematical model that will describe the postulated superstructure. This model will have binary variables representing the existence or not of the β-strands and binary variables denoting the connectivity of the postulated β-strands. In addition, several constraint sets are included in the model so as to represent the antiparallel and parallel arrangements, the physically consistent structures and the disulfide bridges. The main concept in the model derivation relies upon the potential contacts between pairs of hydrophobic amino acids, and the objective function aims at maximizing the hydrophobic-hydrophobic contact energy. The proposed model is an Integer-Linear Programming (ILP) model.

The third component of the proposed framework is the solution of the resulting mathematical model that extracts from the postulated β-strand superstructure the globally optimal solutions of (a) the contacts of hydrophobic residues, (b) the existence of β-strands and their arrangements to form β-sheets, and (c) the disulfide bridge configuration. It is important to emphasize that given the nature of the (ILP) model, a rank ordered list of the second best, third best, etc. solutions can be generated along with the globally optimal solution.

Once predictions of α helical segments have been made, the remaining residues (including those cystine residues in helices) can be further analyzed for possible β-sheet formation. This analysis deviates from the method of Rose and coworkers in that local interactions are not alone used to define β strand propensities. See Baldwin and Rose, *TIBS*, 24:26–33, 1999; Baldwin and Rose, *TIBS*, 24:77–83, 1999. Instead, the procedure utilizes both secondary and tertiary information to predict parallel and antiparallel β sheet formation. In addition, the approach can identify a rank ordered list of possible β sheet arrangements.

The invention's β sheet prediction approach relies on the importance of desolvation forces during the hydrophobic collapse. Justification for predicting β sheet formation through hydrophobic rather than hydrogen bonding forces is receiving growing theoretical support. The controversy extends from the debate over hierarchical folding. In the case of hierarchical folding, it is believed that the β sheet nucleates at the hairpin turn and proceeds to form through a zippering model that is stabilized by hydrogen bond formation. See Munoz et al., *Nature*, 390:196–199, 1997. The alternative view promotes a model in which hairpin formation is driven by the hydrophobic collapse and independent of hydrogen bond formation. Recent simulations have demonstrated and supported the dominant role of hydrophobic forces in driving β sheet formation. Bryant et al., *Biophys J*, 78:584–589, 2000; Pande and Rokhsar, *PNAS*, 96:9062–9067, 1999; Dinne et al., *PNAS*, 96:9068–9073, 1999.

Hydrophobic interactions between β strand residues are used to develop several optimization models that can be globally optimized to provide a rank ordered list of potential β sheet arrangements with decreasing hydrophobic interaction energies. These formulations are classified as (i) a residue-based model and (ii) a strand-based model. Each formulation results in an integer linear programming (ILP) problem in which some form of the hydrophobic contact energy must be maximized.

The first step for generating each formulation is to postulate a superset of the possible β strands segments in the target sequence. A superstructure approach is used to enclose the full spectrum of possible β strands. For the residue based formulation, the β strand definition reduces to each hydrophobic residue. In contrast, the strand-based formulation relies on the identification of contiguous sets of residues to define potential β strands. These individual strands represent one component in the formation of a β sheet configuration.

The following protocol is used to identify potential β strands for the postulated superstructure.

Step 1: Classify all residues not belonging to α-helices as hydrophobic, bridge, turn or other residues. The set of residues, H, are considered to be hydrophobic:

$$H=\{Leu, Ile, Val, Phe, Met, Cys, Tyr, Trp\} \quad (28)$$

The set of residues, B, are considered to be bridge:

$$B=\{Ala, Thr\} \quad (29)$$

The set of residues, T, are considered to be turn:

$$T=\{Asn, Asp, Gly, Pro, Ser\} \quad (30)$$

The set of residues, N, are considered to be other:

$$N=\{Arg, Lys, Glu, Gln, His\} \quad (31)$$

For the case of a Ser residue juxtaposed to a residue belonging to the set of bridge residues, B, the classification of the individual Ser residue is changed from T to B. Step 2: Scan the sequence for H residues, and build β strands by connecting H residues satisfying the following conditions. The following conditions are applied iteratively until the strand can not be further extended. If only one H residue defines the strand proceed directly to step 3.

(a) Two adjoining H residues.
(b) Two H residues separated by 1 residue.
(c) Two H residues separated by 2 residues with the following possible configurations: BT,BN,BB,TB,NB.
(d) Two H residues separated by 3 residues with the following possible configurations: BBN,NBB,BNB, BBT,TBB,BTB,BBB.

(e) Three residue segments comprised of only B residues also define a β strand.

Step 3: Extend the strand to include residues to the left and right of terminal H residues under the following conditions:

(a) Extend to the left by two residues to include NB.

(b) Extend to the left by one residue to include either B or N.

(c) Extend to the right by two residues to include BN.

(d) Extend to the right by one residue to include either B or N.

Step 4: Scan the sequence for segments connecting two T residues, and modify β strands which enclose, intersect or are enclosed within segments satisfying the following conditions (a) Two T residues separated by one H residue.

(b) Two T residues separated by 2 residues with at least one residue belonging to H.

(c) Two T residues separated by 3 residues with at least one residue belonging to H, but not including the following configurations: HBH,HHB,BHH,HHH.

(d) Two T residues separated by 4 residues with only one H residue and no more than one B residue.

The β strands are modified according to the following rules:

(a) If the segment encloses a β strand, the strand is deleted.

(b) If the segment intersects a β strand and the intersecting T residue is not enclosed by an H residue, the strand segment within the T residues is deleted.

(c) If the segment is enclosed by a β strand and the T residues at either end are not enclosed by H residues, the strand is decomposed into two separate strands by deleting the strand segment within the T residues.

Step 5: If the left end of the β strand is defined by the sequence THNN (or the right end is defined by the mirror image) the strand is terminated between the two N residues.

To test the robustness of the approach, the protocol for postulating β strand formation was applied to a substantial subset of the available sequences from the PDB. Specifically, this subset included approximately 2000 individual sequences with sequence lengths between 50 and 150 residues. The predicted β strands were then compared to the observed strand locations, as defined by experiment. Secondary structure assignment of the experimental structures was based on an implementation of the method described in Kabsch and Sander, *Biopolymers*, 22:2577, 1983.

The classification of strand regions from experimental structures provides a total of approximately 11000 strands, or an average of 5 to 6 strands per sequence. The protocol identifies identical or overlapping strands, and the procedure predicts potential strand configurations for the actual strands with 93 percent accuracy (excluding two residue segments classified as strands). According to the classification of residues outlined above, the majority of strands not included only have one or no H residues. Examples of such strands include the following segments: NNN, NNNT, NNHNT, BNTNNT.

A. Residue-based Formulation

In one embodiment, the first formulation is based on residue-to-residue hydrophobic contacts. In this case the β strand superstructure is reduced to the consideration of each hydrophobic residue as an individual unit. Hence, the solution of the mathematical model predicts the contacts between pairs of hydrophobic residues. The identification of β strand is not necessary to develop the formulation, as given by the following protocol for individual contacts.

1. Identify the set of hydrophobic residues. This set excludes those hydrophobic residues contained in α helices. When disulfide bonds may form, all cystine residues, including those in α helical segments, belong to this set. The following set of residues, H, are considered to be hydrophobic:

$$H=\{Leu, Ile, Val, Phe, Met, Cys, Tyr, Trp\} \quad (32)$$

2. Each residue is assigned a position dependent parameter, P(i). The parameter is equal to the position of the hydrophobic residue in the overall sequence and will be used extensively to determine allowable contacts between hydrophobic residues.

3. Associate appropriate hydrophobicity parameters ($H_i$) with these residues. There have been many attempts to develop hydrophobicity scales based on experimentally derived free energy of transfer of amino acids from organic solvents to water. See, e.g., Karplus, *Protein Science*, 6:1302, 1997; Lesser and Rose, *Proteins*, 8:6–13, 1990; Radzicka and Wolfenden, *Biochem*, 27:1664–1670, 1988. In particular, it should be noted that these parameterizations are only valid when considering non-polar (i.e., hydrophobic) groups. Therefore, the development of these scales should include residue burial for hydrophobic groups only. The interaction energy for a potential hydrophobic contact is assumed to be additive.

4. In the case of cystine-cystine contacts an additional energy contribution is added. The contribution is based on the addition of the interaction energy for all hydrophobic residues between the potential disulfide bonding pair. The contribution is normalized based on the length of the intervening segment.

$$H_{ij}^{add} = \begin{cases} \dfrac{\sum\limits_{k,P(i)\leq P(k)\leq P(j)} H_k}{P(j)-P(i)} & \text{if } \{i,j\} \in \{Cys\} \\ 0 & \text{otherwise} \end{cases} \quad (33)$$

5. Set an iteration sequence for the progression of antiparallel/parallel β sheet formation. The (ILP) formulation can be solved iteratively and multiple times, which, through the introduction of integer cuts, can be used to determine competitive interaction energies for several β sheet arrangements.

The objective function for the (ILP) formulation becomes:

$$\max \sum_i \sum_{j,P(i)+2<P(j)} (H_i + H_j + H_{ij}^{add})y_{ij} \quad (34)$$

$$\text{where } y_{ij} = \begin{cases} 1 & \text{if } i,j \text{ form contact} \\ 0 & \text{if } i,j \text{ do not form contact} \end{cases} \forall i<j \quad (35)$$

Figure 11A:
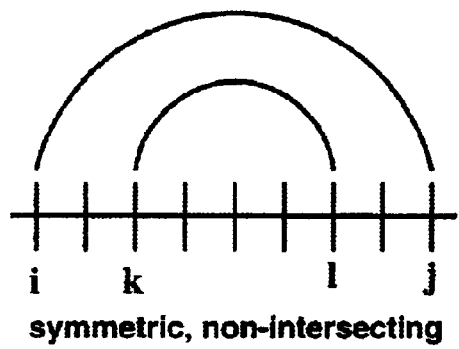
FIG. 11 shows allowed non-intersecting loops (FIG. 11A); disallowed non-intersecting loops (FIG. 1B) for anti-parallel β sheet formation; and allowed intersecting loops (FIG. 11C) and disallowed intersecting loops (FIG. 11D) for parallel β sheet formation.

The first set of constraints define the allowable β sheet configurations. For the case of antiparallel β sheet formation, symmetric non-intersecting loops must be enforced, as shown in FIGS. 11A and B. The following constraints provide the necessary conditions for antiparallel β sheet formation:

$$y_{ij}+y_{kl}\leq 1 \forall P(i)+P(j)\neq P(k)+P(l), y_{ij} \text{ OR } y_{kl} \notin \{Cys, Cys\} \quad (36)$$

Figure 11B:
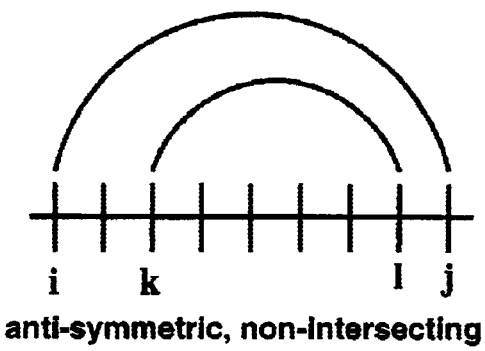
Figure 11C:
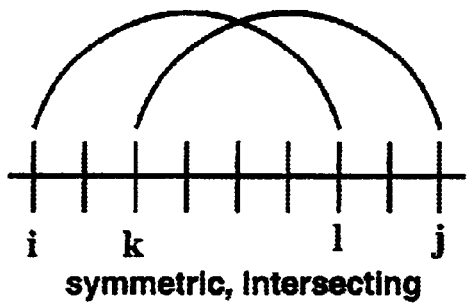
Figure 11D:
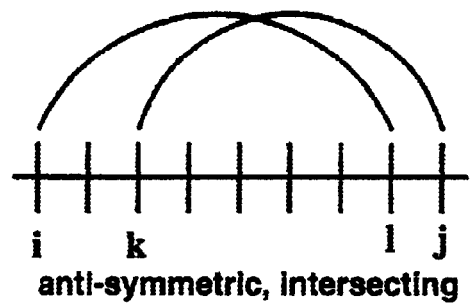

The set of conditions imply that the sum of the contact position parameters must be equal and cannot be intersecting for any combination of contacts defined by ij and kl. In addition, the constraint is not included if a potential contact, either ij or kl, represents the formation of a disulfide bridge. In this way, disulfide bridge contacts are allowed to form non-symmetric, intersecting loops. For the case of parallel β sheet formation, the contacts must involve symmetric intersecting loops, as shown in FIGS. 11C and D. This results in the following set of constraints:

$$y_{ij}+y_{kl}\leq 1 \ \forall P(k)-P(i)\neq P(1)-P(j), y_{ij} \text{ OR } y_{kl} \notin \{Cys, Cys\} \quad (37)$$

Here, the difference between the two sets of contact parameters must be equal, which implies the formation of symmetric intersecting loops for any combination of ij and kl.

A number of constraints are included in the formulation to provide physically consistent arrangements.

$$\sum_{i}\sum_{j,P(i)+7<P(j)} y_{ij} \geq 1 \quad (38)$$

The above constraint requires that at least one contact must form in which at least seven residues fall between residues i and j. This prevents the formation of unrealistically short β-sheet configurations. The following set of constraints, which apply to all hydrophobic residues positions, limits the total number of contacts, $N_i$, allowed at a given position.

$$\sum_{j,P(i)+2<P(j)} y_{ij} + \sum_{j,P(j)+2<P(i)} y_{ij} \leq N_i \ \forall \ i \quad (39)$$

Here $N_i$ represents the total number of possible contacts for hydrophobic residue i. Initially this value is set equal to 1 for all residues so that each residue may participate in only one contact.

When disulfide bridge formation is allowed, an inequality constraint is used to set an upper bound on the number of cystine-cystine contacts. This implies the following constraint:

$$\sum_{i\in\{Cys\}}\sum_{j\in\{Cys\},P(i)+7<P(j)} y_{ij} \leq N_{SS} \quad (40)$$

In this case, $N_{SS}$ is the upper bound value on the number of disulfide bridges.

The resulting (ILP) can be solved to global optimality to identify the set of contacts which maximize the hydrophobic interaction energy defined by the objective function. In general, (ILP) formulations belong to the class of NP complete problems. Floudas, Oxford University Press, New York, 1995; Nemhausser and Wolsey. *Integer and combinatorial optimization*. John Wiley and Sons, New York, 1988. Most available (ILP) codes use a branch-and-bound procedure to search for an optimal integer solution by solving a sequence of related LP relaxations. In this work CPLEX is used to identify globally optimal (ILP) solutions. CPLEX. *Using the CPLEX Callable Library*, ILOG, Inc., 1997.

The procedure for generating the optimal set of hydrophobic contacts involves solving the (ILP) formulation iteratively. For the case of multiple cystine containing sequences, the identification of disulfide bonding pairs is included during the first iteration. For each iteration, the global optimal solution can be identified along with a rank ordered list of possible antiparallel or parallel β sheet configurations.

B. Strand-based Formulations

In another embodiment, three alternative formulations which rely on the superstructure of potential β strands are presented. These formulations can be used to solve residue-to-residue contact or strand-to-strand contact (ILP) problems, or a combination of the two. The advantage of these models is their ability to identify the full β sheet configuration simultaneously.

The strands are identified according to the superstructure approach outlined in the preceding section. For the set of postulated strands in the superstructure the following steps are taken.

1. Each strand is assigned a position dependent parameter, Q(si). The parameter is equal to the strand number by counting sequentially from the N-terminus to the C-terminus of the sequence. Each strand is also described by a start and end residue whose positions are denoted as $P^{beg}(si)$ and $P^{end}(si)$, respectively. The number of hydrophobic residues within the strand is defined by $N_H(si)$.

2. Assign a weight, $(S_{si})$, to each strand. The weight is equal to the average hydrophobicity of the hydrophobic residues in the strand:

$$S_{si} = \frac{\sum_{i,P^{beg}(si)\leq P(i)\leq P^{end}(si)} H_i}{N_H(si)} \quad (41)$$

Formulation 1

The objective function for the strand-to-strand (ILP) formulation becomes:

$$\max\sum_{si}\sum_{sj,Q(si)<Q(sj)} (S_{si}+S_{sj})w_{si,sj} \quad (42)$$

$$\text{where } w_{si,sj} = \begin{cases} 1 \text{ if } si, sj \text{ form contact} \\ 0 \text{ if } si, sj \text{ do not form contact} \end{cases} \forall \ si < sj \quad (43)$$

A number of constraints are included in the formulation to provide physically realistic strand arrangements.

$$\sum_{sj,Q(si)<Q(sj)} w_{si,sj} + \sum_{sj,Q(sj)<Q(si)} w_{sj,si} \leq NS_{si} \ \forall \ si \quad (44)$$

Here $NS_{si}$ represents the total number of possible contacts for strand si. In general, this value is set equal to 2 for all strands, although the proximity of helices may require a reduction of this value to 1. The following set of constraints can be used to enforce special conditions regarding the formation of β-strands.

$$w_{si,sj} \leq DS_{si,sj} \quad (45)$$

Here $DS_{si,sj}$ are parameters which can be used to turn off a particular strand-to-strand contact. In such cases, $DS_{si,sj}$ would be set to zero. For each strand si two constraints are provided to dissallow more than one strand-to-strand match from one side of strand si.

$$\sum_{sj,Q(si)<Q(sj)} w_{si,sj} \leq 1 \ \forall \ si \quad (46)$$

$$\sum_{sj,Q(sj)<Q(si)} w_{sj,si} \leq 1 \forall\, si \quad (47)$$

A final set of constraints impose a maximum value on the number of consecutive strand-to-strand matches.

$$\sum_{sj,Q(si)\leq Q(sj)\leq Q(si)+2} \sum_{sk,Q(sk)=Q(sj)+1} w_{sj,sk} \leq 2 \forall\, si \quad (48)$$

This constraint is used to avoid physically inconsistent arrangements in which a single or a series of β sheet ladders would form.

Formulation 2

The second alternative formulation uses strand definitions to solve the full β-sheet configuration problem. The objective function is based on the residue-to-residue contact energies, as given by Equation 34. The set of constraints defined by Equations 38 and 39 are included in the formulation, although for the general case the parameters $N_i$ of Equation 39 are increased to 2 to allow for multiple residue-to-residue contacts. In addition, the constraints (Equations 36 and 37) enforcing the formation of antisymmetric and symmetric loops are relaxed to include only individual strand pairings. The constraints provided for the strand configuration problem (i.e., Equations 44 to 48) are also included. Finally, the connections between strands and residue contacts are provided by the following set of constraints.

$$y_{ij} \leq w_{si,sj} \forall\, P^{beg}(si) \leq P(i) \leq P^{end}(si),\, P^{beg}(sj) \leq P(j) \leq P^{end}(sj) \quad (49)$$

Here the $y_{ij}$ and $w_{si,sj}$ variables are linked so that the potential $y_{ij}$ contacts between the strands si and sj can become active if the strand-to-strand contact forms (i.e., $w_{si,sj}=1$).

Formulation 3

The third formulation combines the objective functions from both the residue-to-residue and strand-to-strand formulations. This allows both contact energies to influence the prediction of the β sheet configuration through the following objective function:

$$\max \sum_i \sum_{j,P(i)+2<P(j)} (H_i + H_j + H_{ij}^{add}) y_{ij} + \sum_{si} \sum_{sj,Q(si)<Q(sj)} (S_{si} + S_{sj}) w_{si,sj} \quad (50)$$

As this formulation combines both strand and residue contact terms, the constraint set is identical to that of Formulation 2.

III. Derivation of Restraints

Theoretical prediction of the three dimensional structure of a protein has been the focus of intense study. Direct simulation using molecular dynamics has been used to fold several protein systems, although general application of such methods will require much faster computational resources. See, e.g., Duan and Kollman, *Science*, 282:740–744, 1998; Daggett et al., *J. Am. Chem. Soc.*, 120:12740–12754, 1998; Caves et al., *Protein Sci.*, 7:649–666, 1998.

Other theoretical techniques attempt to avoid the need for costly and time consuming experiments by relating the global minimum of a proposed energy hypersurface to the true native structure of the protein. In practice, this approach faces two major challenges: 1) the accuracy of the energy models, and 2) the ability to effectively locate the global minimum among the astronomically large number of minima which exist on the energy surface. Nevertheless, the potential impact of a successful theoretical framework for ab initio protein structure prediction provides an overwhelming impetus for continued investigation.

Another embodiment of the invention focuses on the development of a novel approach for protein structure prediction via experimental NMR-type restraints. Traditionally, the protein folding global optimization problem involves a progression of unconstrained minimizations. However, the introduction of experimentally derived or artificial restraints can be used to recast the fundamental protein folding problem as a constrained global optimization problem. The constraints, through reduction of the feasible search space, serve two important purposes: 1) attempt to correct any deficiencies of the energy model, and 2) focus the efforts of the global optimization algorithm.

The proposed constrained formulation differs from traditional NMR approaches in several fundamental ways. First, the energy model is represented by a detailed full atom force field, rather than simplified nonbonded potential terms. This should make the approach especially effective when the number of NMR-type restraints per residue decreases; that is, the accuracy of the energy model becomes more significant. In addition, traditional solution approaches apply target function distance geometry or simulated annealing to unconstrained problem formulations in which restraints are represented by penalty function approximations. The solution of the constrained formulation requires the use of constrained local optimization solvers and an overall global optimization framework for nonlinearly constrained problems. This is accomplished through the application of the ideas of the αBB deterministic global optimization approach. Adjiman et al., *Comput. Chem. Eng.*, 20:S419–S424, 1996; Adjiman et al., *Comput. Chem. Eng.*, 21:S445–S450, 1997; Adjiman et al., *Comput. Chem. Eng.*, 22:1159–1179, 1998; Adjiman et al., *Comput. Chem. Eng.*, 22:1137–1158, 1998; Androulakis et al., *J. Glob. Opt.*, 7:337–363, 1995.

Because the location of the global minimum relies on effectively solving constrained local optimization problems, convergence to the global minimum can be enhanced by consistently identifying low energy solutions. These observations illustrate the need for reliably locating low energy feasible points for initializing the constrained local optimization routine. Along these lines, a combined torsion angle dynamics (TAD) and simulated annealing scheme has been implemented within the context of the global optimization framework. Torsion angle dynamics (TAD) has recently been shown to be more effective than Cartesian coordinate dynamics. Güntert et al., *J. Mol. Biol.*, 273:283–298, 1997; Rice and Brünger, *Proteins*, 19:277–290, 1994. In this case, the degrees of freedom are rotations around single bonds, which reduces the number of variables by approximately tenfold because bond lengths, bond angles, chirality and planarities are kept fixed at optimal values during the calculation.

A. Energy Modeling

Basic data obtained from restraints from secondary structure prediction and NMR studies consist of distance and torsion angle restraints. Once resonances have been assigned, nuclear Overhauser effect (NOE) contacts are selected and their intensities are used to calculate interproton distances. Information on torsion angles is based on the measurement of coupling constants and analysis of proton chemical shifts. Together, this information is used to formulate a nonlinear optimization problem, the solution of which should provide the correct protein structure. Typically, a hybrid energy function of the following form is employed:

$$E = E_{forcefield} + W_{nmr} E_{nmr} \quad (51)$$

The energy, E, specified by this target function includes a chemical description of the protein conformation through the use of a force field, $E_{forcefield}$. The force field potentials are generally much simpler representations of all atom force fields. The distance and dihedral angle restraints appear as weighted penalty, $E_{nmr}$, terms that should be driven to zero. The second term of Equation (51) can be rewritten as:

$$E_{nmr} = E_{distance} + E_{dihedral} \quad (52)$$

Here $E_{distance}$ and $E_{dihedral}$ represent the violation energies based on the distance and dihedral angle restraints, respectively. These functions can take several forms, although a simple square well potential is commonly used. The expressions also include a summation over both upper and lower distance violations; for example, $E_{distance} = E_{distance}^{upper} + E_{distance}^{lower}$. When considering upper distance restraints this becomes:

$$E_{distance}^{upper} = \sum_j \begin{cases} A_j(d_j - d_j^{upper})^2 & \text{if } d_j > d_j^{upper} \\ 0 & \text{otherwise} \end{cases} \quad (53)$$

The squared violation energy is considered only when the calculated distance $d_j$ exceeds the upper reference distance $d_j^{upper}$. This squared violation can then multiplied by a weighting factor $A_j$. A similar contribution is calculated for those distances that violate a lower reference distance, $d_j^{lower}$:

$$E_{distance}^{lower} = \sum_j \begin{cases} A_j(d_j - d_j^{lower})^2 & \text{if } d_j > d_j^{lower} \\ 0 & \text{otherwise} \end{cases} \quad (54)$$

For dihedral angle restraints the functional form is similar to that of Equations 53 and 54. As before, the total violation, $E_{dihedral}$, is a sum over upper and lower violations (i.e., $E_{dihedral} = E_{dihedral}^{upper} + E_{dihedral}^{lower}$). A dihedral angle $\omega_j$ can be restrained by employing a quadratic square well potential using upper ($\omega_j^{upper}$) and lower ($\omega_j^{lower}$) bounds on the variable values. However, due to the periodic nature of these variables, a scaling parameter must be incorporated to capture the symmetry of the system. Furthermore, by centering the full periodic region on the region defined by the allowable bounds, all transformed values will lie in the domain defined by $[\omega_j^{lower} - \Delta HW_{\omega j}, \omega_j^{upper} + \Delta HW_{\omega j}]$, where $\Delta HW_{\omega j}$ is equal to half the excluded range of dihedral angle values (i.e., $\Delta HW_{\omega j} = \pi - (\omega_j^{upper} - \omega_j^{lower})/2$). This results in the following set of equations:

The force field energy term, $E_{forcefield}$ of Equation 51, models the nonbonded interactions of the protein, which can consist of simple or more detailed energy functions. In practice, when considering NMR restraints, force field terms are often simplified to include only geometric energy terms such as quartic Van der Waals repulsions. Such functions neglect rigorous modeling of energetic terms in order to ensure that experimental distance violations are minimized. In fact, a basic representation for this target function would be:

$$E_S = E_{distance} + E_{dihedral} \quad (57)$$

Here the $E_{distance}$ function includes additional distance restraints to avoid van der Waals contacts. Notice that when all restraints are satisfied, the objective function is driven to zero.

In this work, a detailed modeling approach is proposed by using the ECEPP/3 force field. See Némethy et al., 10. *J. Phys. Chem.*, 96:6472, 1992. For this force field, it is assumed that the covalent bond lengths and bond angles are fixed at their equilibrium values, so that the conformation is only a function of the independent torsional angles of the system. The total force field energy, $E_{forcefield}$, is calculated as the sum of electrostatic, nonbonded, hydrogen bonded, and torsional contributions. The main energy contributions (electrostatic, nonbonded, hydrogen bonded) are computed as the sum of terms for each atom pair (i,j) whose interatomic distance is a function of at least one dihedral angle. The general potential energy terms of ECEPP/3 are shown in FIG. 4, while the development of the appropriate parameters is discussed and reported elsewhere. See Némethy et al., supra.

When considering an unconstrained minimization, this approach provides the following objective function:

$$E_D = E_{distance} + E_{dihedral} + E_{ECEPP/3} \quad (58)$$

In contrast to Equation 57, the detailed energy modeling greatly increases the complexity of the objective function. It should also be noted that the transformation from Cartesian to internal coordinate space results in highly nonlinear functions. That is there is not a one-to-one correspondence between distances and internal coordinates. The advantage for working in dihedral angle space is that the variable set decreases, with the disadvantage being the increased nonconvexity of the energy hypersurface.

B. Restraints for Tertiary Structure Prediction

The final stage of the approach involves the prediction of the tertiary structure of the full protein sequence. The problem formulation is based on the development of atomic distance and dihedral angle restraints, similar in form to NMR-type restraints, which are derived from the helix and beta strand prediction results. In its final form, the problem requires the use of constrained nonlinear global optimization techniques.

For those residues predicted to assume alpha helical and beta strand conformations, dihedral angle bounds are $$E_{dihedral}^{upper} = \sum_j \begin{cases} A_j\left(1 - 2\left[\frac{\omega_j - \omega_j^{upper}}{2\pi - (\omega_j^{upper} - \omega_j^{lower})}\right]^2\right)(\omega_j - \omega_j^{upper})^2 & \text{if } \omega_j > \omega_j^{upper} \\ 0 & \text{otherwise} \end{cases} \quad (55)$$

$$E_{dihedral}^{lower} = \sum_j \begin{cases} A_j\left(1 - 2\left[\frac{\omega_j - \omega_j^{lower}}{2\pi - (\omega_j^{upper} - \omega_j^{lower})}\right]^2\right)(\omega_j - \omega_j^{lower})^2 & \text{if } \omega_j < \omega_j^{lower} \\ 0 & \text{otherwise} \end{cases} \quad (56)$$

assigned according to the values given in the following table:

| Conformer | $\Phi^L$ | $\Phi^U$ | $\Psi^L$ | $\Psi^U$ |
|---|---|---|---|---|
| Alpha | −85 | −55 | −50 | −10 |
| Beta | −155 | −75 | 110 | 180 |

For alpha helices, $C^\alpha$–$C^\alpha$ distances can be restrained between each pair of I and I+3 residues, which anticipates the formation of the alpha-helix hydrogen bond network. In a similar fashion, $C^\alpha$–$C^\alpha$ restraints can be developed for residues in opposing strands of a beta sheet fold, so that hydrogen bond formation between strands is enforced. The beta strand restraints include both hydrophobic residues and intervening residues between the turn and the full extent of the beta sheet. The corresponding upper and lower distance limits are given in the following table:

| Conformer | $D^L$ | $D^U$ |
|---|---|---|
| Alpha | 5.50 | 6.50 |
| Beta | 4.50 | 6.50 |

Additional dihedral angle restraints can be generated through analysis of the unassigned residues in the protein sequence. Specifically, fragments between two consecutive sets of secondary structure comprise a set of candidate loop segments. In a similar fashion to the prediction of helical segments, a series of free energy calculations for overlapping oligopeptides is performed. Contours enclosing the most probable bounds for the backbone dihedral variables are used to further constrain the loop segments during the tertiary structure prediction phase.

IV. Tertiary Structure Prediction

A. Global Optimization

The determination of a three dimensional protein structure defines an optimization problem in which the objective function may correspond to one of the target functions outlined in the previous section. For the simple case, the formulation becomes:

$$\min_\varphi \; E_S(\varphi) = E_{distance} + E_{dihedral} \qquad (59)$$

A standard procedure for addressing this global optimization problem consists of a combination of simulated annealing and molecular or torsional angle dynamics. Generally, multiple initial conformers are generated and optimized to provide a set of acceptable structures. Typically, a set containing on the order of 100 acceptable conformers may be identified, from which a subset of similar structures (approximately 20) are used to characterize the system. The simulated annealing protocol is incorporated in an attempt to reduce trapping in local minimum energy wells.

However, the minimization of complex target functions necessitates the use of rigorous global optimization techniques. For the detailed target function, given by Equation 58, the unconstrained formulation is similar to formulation 59. Through the use of the constrained optimization approach, the dihedral angle bounds are implicitly included as box constraints. Furthermore, distance restraints are treated explicitly. This reformulation removes both $E_{dihedral}$ and $E_{distance}$ from the target function, leaving only $E_{forcefield}$:

$$\min_\varphi \; E_{ECEPP/3}$$

$$\text{subject to} \quad E_l^{distance}(\varphi) \leq E_l^{ref} \quad l = 1, \ldots, N_{CON} \qquad (60)$$
$$\varphi_i^L \leq \varphi_i \leq \varphi_i^U \quad i = 1, \ldots, N_\varphi$$

Here $i=1, \ldots, N_\phi$ corresponds to the set of dihedral angles, $\phi_i$, with $\phi_i^L$ and $\phi_i^U$ representing lower and upper bounds on these dihedral angles. In general, the lower and upper bounds for these variables are set to $-\pi$ and $\pi$, although appropriate bounds derived from NMR or other data are also suitable. The detailed atomistic-level energy function produces a multidimensional surface with an astronomically large number of local minima, for which a variety of techniques have been developed. The major limitation is that these methods depend strongly on the supplied initial conformations. As a result, there is no guarantee for global convergence because large sections of the domain space may be bypassed. To overcome these difficulties, the αBB global optimization approach has been extended to identifying global minimum energy conformations of peptides. The development of this branch and bound method was motivated by the need for an algorithm that could guarantee convergence to the global minimum of nonlinear optimization problems with twice-differentiable functions. Floudas, *Large Scale Optimization with Applications, Part II: Optimal Design and Control*, volume 93, page 129, in IMA Volumes in Mathematics and its Applications, Springer-Verlag, (Biegler et al., eds.) 1997. The application of the αBB to the minimization of potential energy functions was first introduced for microclusters (Maranas and Floudas, *J. Chem. Phys.*, 97(10):7667–7678, 1992; Maranas and Floudas, *Annals of Operations Research*, 42:85–117, 1993), and small acyclic molecules (Maranas and Floudas, *J. Chem. Phys.*, 100(2):1247–1261, 1994; Maranas and Floudas, *J. Glob. Opt.*, 4:135–170, 1994). The αBB approach has also been applied to general constrained optimization problems. Adjiman et al., *Comput. Chem. Eng.*, 21:S445–S450,1997; Adjiman et al., *Comput. Chem. Eng.*, 22:1159–1179, 1998; Adjiman et al., *Comput. Chem. Eng.*, 22:1137–1158, 1998; Androulakis et al., *J. Glob. Opt.*, 7:337–363, 1995. In more recent work, the algorithm has been shown to be successful for isolated peptide systems using the ECEPP/3 potential energy model (Androulakis et al., *J. Glob. Opt.*, 11(1):1–34, 1997; Maranas et al., in *DIMACS Series in Discrete Mathematics and Theoretical Computer Science*, volume 23, page 133, American Mathematical Society, 1996), and including several solvation models (Klepeis et al., *Comput. Chem. Eng.*, 22:765–788, 1998; Klepeis and Floudas, *J. Comp. Chem.*, 20:636–654, 1999.

In one embodiment of the invention, the αBB global optimization approach effectively brackets the global minimum by developing converging sequences of lower and upper bounds. These bounds are refined by iteratively partitioning the initial domain. Upper bounds on the global minimum are obtained by local minimizations of the original nonconvex problem. Lower bounds belong to the set of solutions of the convex lower bounding problems, which are constructed by augmenting the objective and constraint functions through the addition of separable quadratic terms. The lower bounding formulation can be expressed in the following manner:

$$\min_{\varphi} \quad L_{forcefield}(\varphi)$$

$$\text{subject to} \quad L_l^{distance}(\varphi) \le E_l^{ref} \quad l = 1, \ldots, N_{CON} \quad (61)$$

$$\varphi_i^L \le \varphi_i \le \varphi_i^U \quad i = 1, \ldots, N_{\varphi}$$

In this formulation, variable bounds are specific to the subdomain for which the lower bounding functions are constructed. $L_{forcefield}$ refers to the convex representation of the objective function, as given by:

$$L_{forcefield} = E_{forcefield} + \sum_{i=1}^{N_{\varphi}} \alpha_{\varphi_i}(\varphi_i^L - \varphi_i)(\varphi_i^U - \varphi_i) \quad (62)$$

The α parameters represent nonnegative parameters which must be greater or equal to the negative one-half of the minimum eigenvalue of the Hessian of $E_{forcefield}$ over the defined domain. Rigorous bounds on the α parameters can be obtained through a variety of approaches. See, e.g., Adjiman and Floudas, *J. Glob. Opt.*, 9:23–40, 1996; Adjiman et al., *Comput. Chem. Eng.*, 22:1159–1179, 1998; Adjiman et al., *Comput. Chem. Eng.*, 22:1137–1158, 1998; Maranas and Floudas, *J. Chem. Phys.*, 100(2):1247–1261, 1994; Hertz et al., *Comput. Chem. Eng*, 23:1333–1339, 1999. The overall effect of these terms is to overpower the nonconvexities of the original terms by adding the value of 2 α to the eigenvalues of the Hessian of $E_{forcefield}$. Similarly, $L_1^{distance}$ denotes the convex relaxation of the inequality constraints as given by:

$$L_l^{distance} = E_l^{distance} + \sum_{i=1}^{N_{\varphi}} \alpha_{\varphi_i, l}^{distance}(\varphi_i^L - \varphi_i)(\varphi_i^U - \varphi_i) \quad (63)$$

Figure 12:
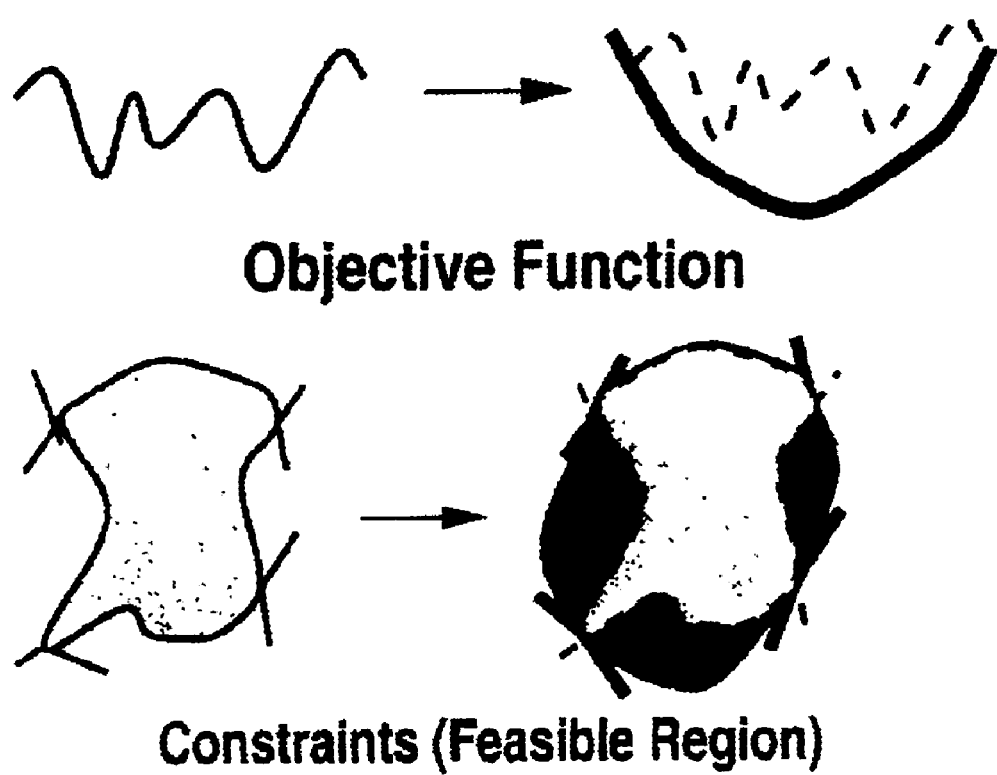
FIG. 12 shows convex underestimator constructed for one dimensional nonconvex objective function. A two dimensional convexification of a nonlinear constraint set is also shown. This convexification, or relaxation of the original functions, forms the foundation of the αBB algorithm.

An illustration of the convexification of a nonconvex objective function and constraint set is given in FIG. 12.

Once solutions for the upper and lower bounding problems have been established, the next step is to modify these problems for the next iteration. This is accomplished by successively partitioning the initial domain into smaller subdomains. For the protein conformation problems, it has been found that one effective partitioning strategy involves bisecting the same variable dimension across all nodes at a given level. In order to ensure non-decreasing lower bounds, the hyper-rectangle to be bisected is chosen by selecting the region which contains the infimum of the minima of lower bounds. A non-increasing sequence for the upper bound is found by solving the nonconvex problem locally and selecting it to be the minimum over all the previously recorded upper bounds. If the single minimum of $L_{forcefield}$ for any hyper-rectangle is greater than the current upper bound, this hyper-rectangle can be discarded because the global minimum cannot lie within this subdomain (fathoming step). The computational requirement of the αBB algorithm depends on the number of variables (global) on which branching occurs. Therefore, these global variables need to be chosen carefully.

B. Torsion Angle Dynamics

Standard unconstrained molecular dynamics simulations have been used extensively to model the folding and unfolding of protein systems. Duan and Kollman, *Science*, 282:740–744, 1998; Daggett et al., *J. Am. Chem. Soc.*, 120:12740–12754, 1998; Caves et al., *Protein Sci.*, 7:649–666, 1998. In addition, several methods for NMR structure calculation have been based on molecular dynamics in Cartesian space. See, e.g., Brünger, X-PLOR, version 3.1 a system for x-ray crystallography and nmr, Yale University Press, New Haven, USA, 1992. Torsion angle dynamics differs from traditional molecular dynamics in that bond lengths and bond angles are fixed at equilibrium values, thereby allowing for a transformation from the Cartesian to the internal coordinate system. The constraints on the systems also dampen high frequency motions, which permits the use of longer time steps during the numerical integration of the equations of motion. The use of TAD in place of conventional MD has been found to improve the efficiency of NMR structure prediction. Güntert et al., *J. Mol. Biol.*, 273:283–298, 1997; Rice and Brünger, *Proteins*, 19:277–290, 1994.

A major disadvantage for employing TAD in place of Cartesian MD is that the equations of motion become much more complex for the constrained system. For unconstrained Cartesian MD the accelerations of the atoms can be calculated independently due to the decoupled nature of the equations of motion. The addition of constraints to the Cartesian system transforms the equations from a system of ODEs to a system of differential algebraic equations (D)AEs). The alternative to solving this system of DAEs is to transform the equations of motion to the internal coordinate reference frame. In this case, the solution of a linear matrix equation in each time step is required, which, due to the highly coupled structure of the equations, scales as a cubic function of the number of degrees of freedom (torsion angles). To avoid the potentially prohibitive computational cost required for the solution of the equations of motion, in one embodiment of the invention, a fast recursive algorithm, which scales linearly with the number of torsion angles, was implemented. The algorithm is based on spatial operator algebra which has been used to simulate the dynamics of astronautical and robotic equipment. Jain et al., *J. Comp. Phys.*, 106:258–268, 1993.

The algorithm solves for the torsional accelerations, $\ddot{\theta}$:

$$M(\theta)\ddot{\theta} + C(\theta, \dot{\theta}) = 0 \quad (64)$$

In this equation M is an N×N nonlinear mass matrix and C is the N dimensional vector of velocity dependent (Coriolis and other) forces. $\theta$, $\dot{\theta}$ and $\ddot{\theta}$ represent the torsional position, velocities and accelerations, respectively. The ability to calculate the accelerations recursively relies on the chainlike structure of the protein, in which each node of the chain represents a rigid body. These rigid bodies consist of one atom or a cluster of atoms whose relative positions are fixed. To simplify the explanation of the algorithm, an unbranched chain will be considered, although the approach can be easily extended to branched systems. For this simple case, the first rigid body, at one end of the chain, defines the base (k=0), while the last rigid body, at the other end of the chain, defines the tip (k=N). The rotatable torsion angle between bodies k and k−1 is defined as $\theta_k$.

The framework of the algorithm to calculate $\ddot{\theta}$ can be broken down into three steps:

Step 1: A recursion from the base to the tip is required to calculate the positions, spatial velocities, Coriolis and gyroscopic terms for each of the rigid bodies. To proceed the 6×6 spatial transformation matrix, $\phi_k$, between rigid bodies k and k−1 must first be defined:

$$\varphi_k = \begin{bmatrix} I_3 & \tilde{l}(r_k - r_{k-1}) \\ 0_3 & I_3 \end{bmatrix} \quad (65)$$

Here $I_3$ and $O_3$ denote the 3×3 dimensional identity and zero matrices, while the [1\tilde] operator refers to the cross product tensor associated with $r_k$-$r_{k-1}$, where $r_k$ is the position vector that defines the reference frame for rigid body k. The spatial velocity, $V_k$, can be computed from the following relation:

$$V_k = \phi_k^T V_{k-1} + H_k^T \dot{\theta}_k \quad (66)$$

The spatial velocity is a six dimensional vector that combines both the three dimensional angular, ω, and linear, v, velocities:

$$V_k \equiv \begin{pmatrix} \omega_k \\ v_k \end{pmatrix} \quad (67)$$

$H_k$ is also a six dimensional vector with the first three elements corresponding to the unit vector, $e_k$, in the direction of the bond forming the connection between rigid bodies k and k−1:

$$H_k \equiv \begin{pmatrix} e_k \\ 0 \end{pmatrix} \quad (68)$$

The Coriolis and gyroscopic terms, $a_k$ and $b_k$, respectively, can then be calculated using the following relationships:

$$a_k = \begin{pmatrix} 0 \\ \tilde{\omega}_{k-1}[v_k - v_{k-1}] \end{pmatrix} + \begin{pmatrix} \tilde{\omega}_k & 0 \\ 0 & \tilde{\omega}_k \end{pmatrix} H_k^T \dot{\theta}_k \quad (69)$$

$$b_k = \begin{pmatrix} \tilde{\omega}_k J_k \tilde{\omega}_k \\ m_k \tilde{\omega}_k \tilde{\omega}_k Y_k \end{pmatrix} \quad (70)$$

Both $a_k$ and $b_k$ are six dimensional vectors. $m_k$, $Y_k$ and $J_k$ represent the mass, the center of mass vector, and the 3×3 inertia matrix for the rigid body, respectively. Finally, the spatial inertia, $L_k$, of the rigid body about the reference frame is given by the following 6×6 matrix:

$$L_k = \begin{pmatrix} J_k & m_k \tilde{Y}_k \\ -m_k \tilde{Y}_k & m_k I_3 \end{pmatrix} \quad (71)$$

Step 2: The next step requires a backward recursion from the tip, k=N, to the base, k=1. The recursion is used to store a number of auxiliary quantities needed for the final forward recursion to calculate the accelerations. In addition, the gyroscopic terms, $b_k$, and the spatial inertia terms, $L_k$, calculated in step 1 can be used to initialize two auxiliary quantities, $z_k$ and $P_k$, respectively. Both $P_k$ and $Z_k$ are updated recursively using the following intermediate terms:

$$D_k = H_k P_k H_k^T \quad (72)$$

$$G_k = P_k H_k^T D_k^{-1} \quad (73)$$

$$\epsilon_k = -H_k(z_k + P_k a_k) - \nabla E_k \quad (74)$$

Here $D_k$ and $\epsilon_k$ denote scalar quantities, while $G_k$ is a six dimensional vector. The final equation requires the gradient of the potential function, $\nabla E_k$.

The recurrence relationships for $P_{k-1}$ and $z_{k-1}$ are given by:

$$P_{k-1} \leftarrow P_{k-1} + \phi_k(P_k - G_k H_k^T P_k)\phi_k^T \quad (75)$$

$$z_{k-1} \leftarrow z_{k-1} + \phi_k(z_k + P_k a_k + G_k \epsilon_k) \quad (76)$$

Step 3: A final forward recursion from the base to the tip is used to obtain the θ values. The six dimensional vector $\alpha_k$ is used to store intermediate quantities, with $\alpha_k$ equal to a vector of zeroes for k=0.

$$\alpha_k = \phi_k^T \alpha_{k-1} \quad (77)$$

$$\ddot{\theta}_k = \epsilon_k D_k^{-1} - G_k \alpha_k \quad (78)$$

The following recursion relation is used to update the values of $\alpha_k$ $$\alpha_k \leftarrow \alpha_k + H_k \ddot{\theta}_k + a_k \quad (79)$$

For branched molecular structures, each node can potentially spawn more than one child so that both the inward and outward recursions must be modified. In the case of an inward recursion, the results from each of the child nodes must be summed up before moving up one level. In the case of the outward recursion, each of the node branches requires a separate recursion.

The TAD is carried out using simulated annealing, with temperature control provided by coupling to an external bath. This coupling provides a means for forcing or damping the torsional velocities using the following scaling factor at time t:

$$f_T = \sqrt{1 - \frac{1}{\beta} + \frac{T_o}{\beta T(t)}} \quad (80)$$

In this equation, β is a force constant, while $T_o$ is the bath temperature and T(t) is the actual temperature. The actual temperature is calculated from the kinetic energy, $E_{kinetic}$, with the following relationship:

$$T(t) = \frac{2 E_{kinetic}(t)}{N_\varphi k_B} \quad (81)$$

where $k_B$ is the Boltzmann constant. The value for $f_T$ is used to scale the torsional velocities:

$$\dot{\theta}(t) \leftarrow f_T \dot{\theta}(t) \quad (82)$$

Once torsional velocities have been determined, the accelerations, $\ddot{\theta}$, can be calculated using the recursive algorithm outlined above. A basic leap-frog technique is then employed to calculate velocities at the half time-step, which can be used to calculate torsional positions, θ, and new estimated velocities at the full time step.

C. Algorithmic Steps

The algorithmic steps for the constrained αBB approach can be generalized to any force field model or routine for solving constrained optimization problems. In this work, the αBB approach is interfaced with PACK (Scheraga. PACK: *Programs for Packing Polypeptide Chains*, 1996. online documentation) and NPSOL (Gill et al., *NPSOL 4.0 User's Guide*. Systems Optimization Laboratory, Dept. of Operations Research, Stanford University, Calif., 1986). PACK is used to transform to and from Cartesian and internal coordinate systems, and to obtain function and gradient contributions for the ECEPP/3 force field and the distance constraint equations. NPSOL is a local nonlinear optimization solver that is used to locally solve the constrained upper and lower bounding problems in each subdomain.

The implementation can be broken down into two main phases: initialization and computation. The basic steps of the initialization phase in one embodiment are as follows:

1. Choose the set of global variables. Since the bounds on these variables will be refined during the course of global optimization, they should be selected based on their overall effect on the structure of the molecule. In this work (and in general) the $\phi$ and $\psi$ dihedral angles provide the largest structural variability, and are chosen to constitute the global variable set.

2. Set upper and lower bounds on all dihedral angles (variables). If information is not available for a given dihedral angle, the variable bounds are set to $[-\pi,\pi]$. Since a constrained local optimization solver is used these box constraints are strictly enforced.

3. Identify the set of NOE derived distance restraints to be used in the constraints. In general, this set can include all intra- and inter-residue restraints. In this work, only backbone sequential and medium/long range information was used in developing the constraints, because intra-residue restraints are less likely to affect the overall fold. Although the formulation can handle multiple constraints, distance restraints were included as one constraint ($N_{CON}=1$) for the computational studies.

4. Choose the value of $E^{ref}_1$ to be used in the constraint equations. This can be determined by simply performing several local constrained optimizations or possibly a short global optimization run with simplified energy models. In this work, information based on X-PLOR results was used to define the $E^{ref}$ parameter (see below).

5. Identify initial $\alpha$ values for both the objective and constraint functions.

6. Set initial best upper bound to an arbitrarily large value.

The computation phase of the algorithm involves an iterative approach, which depends on the refinement of the original domain by partitioning along the global variables. In each subdomain, upper and lower bounding problems are solved locally and used to develop the sequence of converging upper and lower bounds. The basic steps in one embodiment are as follows:

1. The original domain is partitioned along one of the global variables.

2. Lower bounding functions for both the objective and constraints are constructed in both subdomains. A constrained local minimization is performed using the following procedure:

A. 100 random points are generated and used for evaluation of the lower bounding objective function and constraints. The point with the minimum objective function value is used as a starting point for local minimization using NPSOL.

B. If the minimum value found is greater than the current best upper bound the subdomain can be fathomed (global minimum is outside region), otherwise the solution is stored.

3. The upper bounding problems (original constrained formulation) are then solved in both subdomains according to the following procedure:

A. 100 random points are generated and used for evaluation of the objective function and constraints. The point with the minimum objective function value and feasible constraints is used as a starting point for local minimization using NPSOL. If a feasible starting point is not found, local minimization is not performed.

B. All feasible solutions are stored.

4. The current best upper bound is updated to be the minimum of those thus far stored.

5. The subdomain with the current minimum value of $L_{forcefield}$ is selected and partitioned along one of the global variables.

6. If the best upper and lower bounds are within a defined tolerance the program will terminate, otherwise it will return to Step 2.

To enhance the search for low energy feasible points, the basic procedure described in Step 3. A is modified to include TAD. The following protocol is used:

1. Set counter, c=1. Perform TAD (1000 high temperature steps followed by 3000 annealing steps) using $E_S$ as the target function. The torsion angle bounds of the current subdomain determine the dihedral angle restraint functions. In addition to the NOE derived distance restraints, sterically based distance restraints are added to prevent van der Waals overlaps.

A. If the $E^{distance}_1 < E^{ref}_1$ $\forall 1=1, \ldots, N_{CON}$, go to step 2. Else go to step 1.B.

B. Increment counter, c=c+1. If c<5, reduce weight of sterically based distance restraints, perform new TAD and go to step 1.A. Else go to step 2.

2. Set counter, c=1. Perform local minimization using NPSOL with dihedral angle box constraints to implicitly enforce bounds. The objective function is a weighted combination of forcefield energy and distance restraint terms:

$$E = E_{ECEPP/3} + \sum_l W_l E_l^{distance} \tag{83}$$

where the weights, $W_1$, are based on the violation of the distance constraints:

$$W_l = \sqrt{1 + \frac{E_l^{distance}}{E_l^{ref}}} \tag{84}$$

A. If $E^{distance}_1 < E^{ref}_1$ $\forall 1=1, \ldots, N_{CON}$, go to step 3. Else go to step 2.B.

B. Increment counter, c=c+1. If c<5, increase weight of distance restraint terms, perform TAD (100 high temperature steps followed by 300 annealing steps) and go to step 2.A. Else go to step 3.

3. Solve the constrained minimization problem using NPSOL.

EXAMPLES

Below are examples of specific embodiments for carrying out the present invention. The Examples are offered for illustrative purposes only, and are not intended to limit the scope of the present invention in any way. Those skilled in the art will recognize modifications that are within the spirit and scope of the invention.

Efforts have been made to ensure accuracy with respect to numbers used, but some experimental error and deviation should, of course, be allowed for.

Example 1

Determination of Helical Regions

1. Bovine Pancreatic Trypsin Inhibitor, BPTI

The approach for $\alpha$-helix prediction was applied to bovine pancreatic trypsin inhibitor (BPTI), a small globular protein found in many tissues throughout the body. BPTI inhibits several of the serine protease proteins such as trypsin, kallikrein, chymotrypsin, and plasmin, and is a member of the pancreatic trypsin inhibitor (kunitz) family, which is a family of serine protease inhibitors. These proteins usually have conserved cysteine residues that participate in the formation of disulfide bonds. In particular, BPTI possesses three disulfide bonds, which are denoted as Cys5–Cys55, Cys14–Cys38, and Cys30–Cys51. The structure of the 58 amino acid residues chain of BPTI has been resolved through several methods, including X-ray crystallography (4PTI) (Deisenhofer and Steigemann, *Acta Crystallogr. Sect B*, 31:238–250, 1975) and a combination of X-ray and neutron diffraction experiments (5PTI) (Wlodawer et al., *J. Mol. Biol.*, 180:301–329, 1984). Basic secondary structural features include a N-terminal $3_{10}$ helix, a C-terminal $\alpha$ helix and several antiparallel $\beta$ strand configurations.

Extensive experimental studies of the structural features and folding of BPTI have been conducted. Creighton et al., *J. Mol. Biol.*, 123:129–147, 1978; Creighton and Goldenberg, *J. Mol. Biol.*, 179:497–526, 1984; States et al., *J. Mol. Biol.*, 195:731–739, 1984; Creighton, *Biochem.*, 270:1–16, 1990; Weissman and Kim, *Science*, 253:1386–1393, 1991. Many of these studies have attempted to elucidate the folding pathway of BPTI through the formation of stable intermediates, which necessarily have one or more broken disulfide bridges. Theoretical investigations of the stability and folding of BPTI have also been performed. Burgess and Scheraga, *Proc. Natl. Acad. Sci.*, 72:1221–1225, 1975; Levitt, *J. Mol. Biol.*, 170:723–764, 1983; Hao et al., *Biochem.*, 32:9614–9631, 1993. These simulations typically require information on secondary structural content and native contacts to examine the formation of the native folded state. One novel aspect of the invention's approach is the identification of secondary structural features, including a helix prediction, through ab initio modeling.

For BPTI, the partitioning of the overall 58 residue chain into overlapping pentapeptides results in 54 pentapeptides. The amino acid sequence for BPTI is as follows:

RPDFCLEPPYTGPCKARIIRYFYNAKAGLCQTFVYG-GCRAKRNNFKSAEDCMRTCGGA<SEQ ID NO: 55>.

The individual uncharged pentapeptides are indicated in Table 1. In general, the end groups for each pentapeptide are simply neutral amino groups at N termini and hydroxyl groups at C termini. For the case of N terminal proline residues the amino group is replaced by an acetyl-amino group, while C terminal proline residues require an amide-methyl group. The structural classification of each pentapeptide is based on the conformational characteristics of the three central residues. Based on the crystallographic structure, Table 1 indicates which pentapeptides possess core residues with full $\alpha$ helical structure.

Table 1: Pentapeptide sequences used for a helix prediction of BPTI. The second column provides the sequence id no. for each pentapeptide, while an (X) in the third column indicates the location, determined by experiment, of a helical core for the given sequence.

TABLE 1

| Pentapeptide | SEQ ID NO: | PDB |
|---|---|---|
| Arg Pro Asp Phe Cys | SEQ ID NO:1 | X |
| Pro Asp Phe Cys Leu | SEQ ID NO:2 | X |

TABLE 1-continued

| Pentapeptide | SEQ ID NO: | PDB |
|---|---|---|
| Asp Phe Cys Leu Glu | SEQ ID NO:3 | |
| Phe Cys Leu Glu Pro | SEQ ID NO:4 | |
| Cys Leu Glu Pro Pro | SEQ ID NO:5 | |
| Leu Glu Pro Pro Tyr | SEQ ID NO:6 | |
| Glu Pro Pro Tyr Thr | SEQ ID NO:7 | |
| Pro Pro Tyr Thr Gly | SEQ ID NO:8 | |
| Pro Tyr Thr Gly Pro | SEQ ID NO:9 | |
| Tyr Thr Gly Pro Cys | SEQ ID NO:10 | |
| Thr Gly Pro Cys Lys | SEQ ID NO:11 | |
| Gly Pro Cys Lys Ala | SEQ ID NO:12 | |
| Pro Cys Lys Ala Arg | SEQ ID NO:13 | |
| Cys Lys Ala Arg Ile | SEQ ID NO:14 | |
| Lys Ala Arg Ile Ile | SEQ ID NO:15 | |
| Ala Arg Ile Ile Arg | SEQ ID NO:16 | |
| Arg Ile Ile Arg Tyr | SEQ ID NO:17 | |
| Ile Ile Arg Tyr Phe | SEQ ID NO:18 | |
| Ile Arg Tyr Phe Tyr | SEQ ID NO:19 | |
| Arg Tyr Phe Tyr Asn | SEQ ID NO:20 | |
| Tyr Phe Tyr Asn Ala | SEQ ID NO:21 | |
| Phe Tyr Asn Ala Lys | SEQ ID NO:22 | |
| Tyr Asn Ala Lys Ala | SEQ ID NO:23 | |
| Asn Ala Lys Ala Gly | SEQ ID NO:24 | |
| Ala Lys Ala Gly Leu | SEQ ID NO:25 | |
| Lys Ala Gly Leu Cys | SEQ ID NO:26 | |
| Ala Gly Leu Cys Gln | SEQ ID NO:27 | |
| Gly Leu Cys Gln Thr | SEQ ID NO:28 | |
| Leu Cys Gln Thr Phe | SEQ ID NO:29 | |
| Cys Gln Thr Phe Val | SEQ ID NO:30 | |
| Gln Thr Phe Val Tyr | SEQ ID NO:31 | |
| Thr Phe Val Tyr Gly | SEQ ID NO:32 | |
| Phe Val Tyr Gly Gly | SEQ ID NO:33 | |
| Val Tyr Gly Gly Cys | SEQ ID NO:34 | |
| Tyr Gly Gly Cys Arg | SEQ ID NO:35 | |
| Gly Gly Cys Arg Ala | SEQ ID NO:36 | |
| Gly Cys Arg Ala Lys | SEQ ID NO:37 | |
| Cys Arg Ala Lys Arg | SEQ ID NO:38 | |
| Arg Ala Lys Arg Asn | SEQ ID NO:39 | |
| Ala Lys Arg Asn Asn | SEQ ID NO:40 | |
| Lys Arg Asn Asn Phe | SEQ ID NO:41 | |

TABLE 1-continued

| Pentapeptide | SEQ ID NO: | PDB |
|---|---|---|
| Arg Asn Asn Phe Lys | SEQ ID NO:42 | |
| Asn Asn Phe Lys Ser | SEQ ID NO:43 | |
| Asn Phe Lys Ser Ala | SEQ ID NO:44 | |
| Phe Lys Ser Ala Glu | SEQ ID NO:45 | |
| Lys Ser Ala Glu Asp | SEQ ID NO:46 | |
| Ser Ala Glu Asp Cys | SEQ ID NO:47 | X |
| Ala Glu Asp Cys Met | SEQ ID NO:48 | X |
| Glu Asp Cys Met Arg | SEQ ID NO:49 | X |
| Asp Cys Met Arg Thr | SEQ ID NO:50 | X |
| Cys Met Arg Thr Cys | SEQ ID NO:51 | X |
| Met Arg Thr Cys Gly | SEQ ID NO:52 | X |
| Arg Thr Cys Gly Gly | SEQ ID NO:53 | |
| Thr Cys Gly Gly Ala | SEQ ID NO:54 | |

For each pentapeptide, a series of free energy calculations was performed to identify low energy conformational ensembles. Energy modeling included standard potential energy components based on the ECEPP/3 forcefield, as well as configurational entropic contributions according to the harmonic approximation. The description of each conformer requires the specification of a set of independent torsion angles, and uniqueness of individual conformers was assessed based on criteria involving these variables. The total number of torsion angles and unique conformers for each pentapeptide is presented in Table 2.

Table 2: Summary of pentapeptide information. The second column provides the number of dihedral angles for the peptide, while the third column indicates the total number of unique conformers identified during the ensemble generation of the uncharged pentapeptides.

TABLE 2

| SEQ ID NO: | DA | Unique |
|---|---|---|
| 1 | 33 | 16047 |
| 2 | 32 | 15176 |
| 3 | 35 | 15537 |
| 4 | 32 | 13700 |
| 5 | 29 | 9503 |
| 6 | 30 | 12065 |
| 7 | 29 | 13228 |
| 8 | 27 | 8945 |
| 9 | 28 | 11222 |
| 10 | 27 | 11004 |
| 11 | 29 | 9783 |
| 12 | 27 | 8202 |
| 13 | 36 | 15528 |
| 14 | 39 | 13817 |
| 15 | 42 | 14838 |
| 16 | 44 | 17851 |
| 17 | 46 | 20289 |
| 18 | 41 | 17768 |
| 19 | 40 | 14571 |
| 20 | 39 | 14240 |
| 21 | 33 | 14692 |
| 22 | 35 | 15915 |
| 23 | 34 | 13479 |
| 24 | 31 | 11169 |
| 25 | 32 | 10419 |
| 26 | 32 | 12468 |
| 27 | 31 | 12116 |
| 28 | 33 | 13306 |
| 29 | 35 | 15591 |
| 30 | 34 | 14253 |
| 31 | 36 | 17216 |
| 32 | 32 | 13296 |
| 33 | 29 | 11578 |
| 34 | 28 | 9785 |
| 35 | 32 | 14398 |
| 36 | 30 | 9998 |
| 37 | 35 | 11704 |
| 38 | 42 | 16344 |
| 39 | 44 | 17904 |
| 40 | 40 | 13700 |
| 41 | 41 | 15364 |
| 42 | 41 | 17997 |
| 43 | 36 | 18261 |
| 44 | 34 | 15945 |
| 45 | 35 | 14153 |
| 46 | 36 | 14136 |
| 47 | 32 | 14248 |
| 48 | 34 | 12565 |
| 49 | 40 | 12630 |
| 50 | 39 | 16798 |
| 51 | 37 | 9503 |
| 52 | 36 | 16426 |
| 53 | 32 | 13802 |
| 54 | 26 | 13127 |

Figure 13:
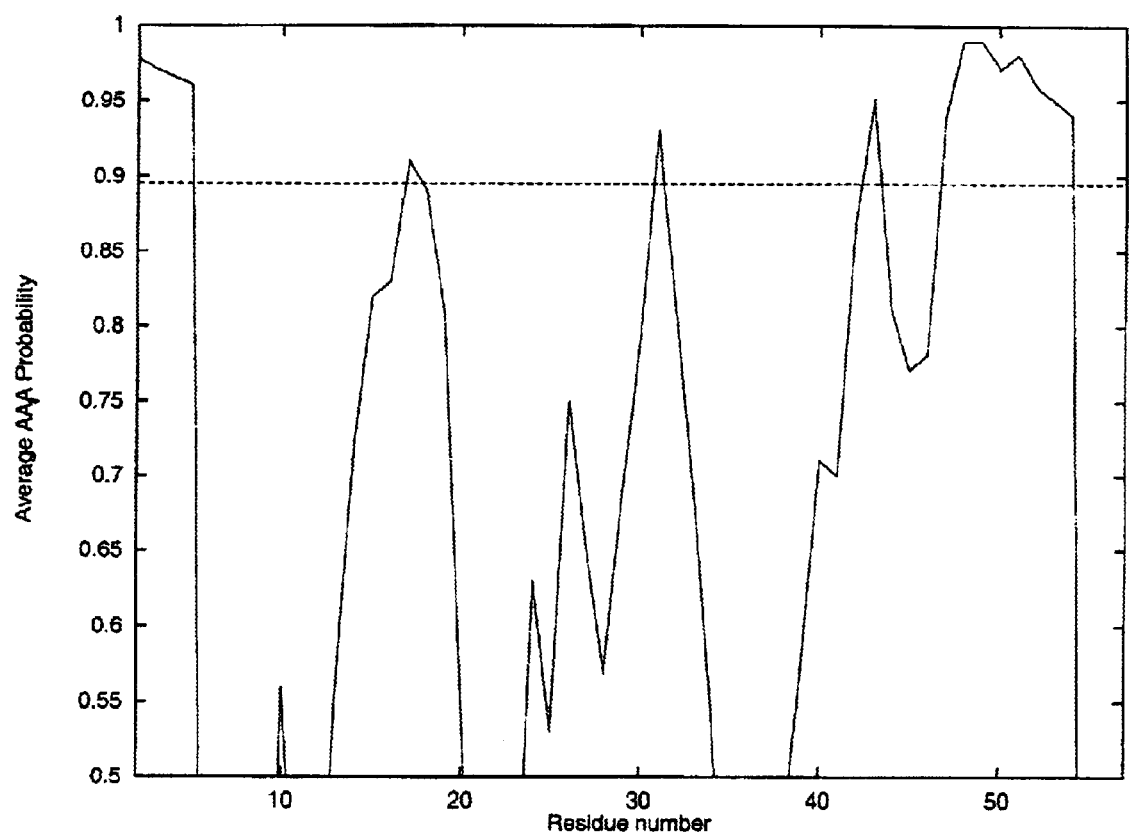
FIG. 13 shows a probability of α-helix formation of central three residues for BPTI, plotted versus central residue of each pentapeptide. The identification of a helical segment corresponds to average helical propensities exceeding 90% for more than three consecutive residues. For BPTI, helical segments are predicted between residues 2 and 5 and between residues 47 and 54.

The free energy of each unique conformer evaluated at 298 K was used to calculate individual occupational probabilities for these metastable states. Clustering of these states was based on the classification of the backbone torsion angles of the central residues. Specifically, the probabilities of conformers exhibiting identical Zimmermann codes for the core residues were summed and used to generate a rank ordered list of conformational propensity. The first stage of the approach involves the identification of strong α helical clusters for the uncharged pentapeptides. Specifically, if the probability of the α helical cluster (AAA) is greater than 90 for more than three consecutive sets of core residues, the marked pentapeptides are considered for further analysis. The second stage involves refinement of α helix probabilities based on detailed electrostatic and ionization energy calculations obtained through the solution of the Poisson Boltzmann equation. For the set of possible α helical pentapeptides containing ionizable residues, probabilities were recalculated for a subset of conformers using a combination of the free energy at 298 K and the polarization and ionization free energy at pH 7. Finally, α helical propensity for each residue was assigned according to the average AAA probability. The results are presented in FIG. 13. The prediction of an α helix corresponds to average AAA probabilities greater than 90 for more than three consecutive residues. For BPTI, α helices are predicted between residues 2 and 5 and between residues 47 and 54. These results are in excellent agreement with the experimental structure.

2. Protein G, 1GB1

Protein G is a small globular protein produced by several Streptococcal species. The proteins are composed of two or three nearly identical domains of about 55 amino acids each. The system considered here is the immunoglobulin-binding domain from streptococcal protein G, a 56 amino acid polypeptide. The amino acid sequence is as follows:
MTYKLILNGKTLKGETTTEAVDAATAEKVFKQYAN-
DNGVDGEWTYDDATKTFTVTE<SEQ ID NO: 56>.

The structure contains an efficiently packed hydrophobic core between a four-stranded β-sheet and a four-turn α-helix with an overall secondary structure of ββαββ. The formation of the β-sheet consists of two β hairpin turns, each connecting antiparallel strands. The first and last strands combine to form the final parallel β sheet to give the four-stranded configuration. Experimental structures have been determined using both crystallographic (Gallagher et al., *Biochem.*, 33:4721–4729, 1994) and NMR-derived data (Gronenborn et al., *Science*, 253:657–660, 1991).

Analysis of the immunoglobulin binding domain of Protein G has also been the focus of theoretical studies on protein folding. In particular, the third and fourth β strands have been used to model the formation of β sheet structure through hairpin folding. Initial observations included the proposal of a simple statistical mechanical model in which the formation of hydrogen bonds, through a zipper mechanism, drives hairpin folding. Munoz et al., *Nature*, 390:196–199, 1997. More recently, simulations have shown that an early step in hairpin folding is the formation of a hydrophobic cluster. Pande and Rokhsa, *PNAS*, 96:9062–9067, 1999; Dinner et al., *PNAS*, 96:9068–9073, 1999; Bryant et al., *Biophys J*, 78:584–589, 2000.

For Protein G, a total of 52 overlapping pentapeptides, as presented in Table 3, were constructed. For all pentapeptides end groups corresponded to neutral amino groups at N termini and hydroxyl groups at C termini. The structural classification of each pentapeptide is based on the conformational characteristics of the three central (core) residues. Based on the experimentally derived structure, Table 3 indicates that pentapeptides 22 through 32 possess core residues with full α helical structure.

Table 3: Pentapeptide sequences used for α helix prediction of Protein G. The second column assigns the identifier for each pentapeptide, while and (X) in the third column indicates the location, determined by experiment, of a helical core for the given sequence.

TABLE 3

| Pentapeptide | SEQ ID NO: | PDB |
|---|---|---|
| Met Thr Tyr Lys Leu | SEQ ID NO:57 | |
| Thr Tyr Lys Leu Ile | SEQ ID NO:58 | |
| Tyr Lys Leu Ile Leu | SEQ ID NO:59 | |
| Lys Leu Ile Leu Asn | SEQ ID NO:60 | |
| Leu Ile Leu Asn Gly | SEQ ID NO:61 | |
| Ile Leu Asn Gly Lys | SEQ ID NO:62 | |
| Leu Asn Gly Lys Thr | SEQ ID NO:63 | |
| Asn Gly Lys Thr Leu | SEQ ID NO:64 | |
| Gly Lys Thr Leu Lys | SEQ ID NO:65 | |
| Lys Thr Leu Lys Gly | SEQ ID NO:66 | |
| Thr Leu Lys Gly Glu | SEQ ID NO:67 | |
| Leu Lys Gly Glu Thr | SEQ ID NO:68 | |
| Lys Gly Glu Thr Thr | SEQ ID NO:69 | |
| Gly Glu Thr Thr Thr | SEQ ID NO:70 | |
| Glu Thr Thr Thr Glu | SEQ ID NO:71 | |

TABLE 3-continued

| Pentapeptide | SEQ ID NO: | PDB |
|---|---|---|
| Thr Thr Thr Glu Ala | SEQ ID NO:72 | |
| Thr Thr Glu Ala Val | SEQ ID NO:73 | |
| Thr Glu Ala Val Asp | SEQ ID NO:74 | |
| Glu Ala Val Asp Ala | SEQ ID NO:75 | |
| Ala Val Asp Ala Ala | SEQ ID NO:76 | |
| Val Asp Ala Ala Thr | SEQ ID NO:77 | |
| Asp Ala Ala Thr Ala | SEQ ID NO:78 | X |
| Ala Ala Thr Ala Glu | SEQ ID NO:79 | X |
| Ala Thr Ala Glu Lys | SEQ ID NO:80 | X |
| Thr Ala Glu Lys Val | SEQ ID NO:81 | X |
| Ala Glu Lys Val Phe | SEQ ID NO:82 | X |
| Glu Lys Val Phe Lys | SEQ ID NO:83 | X |
| Lys Val Phe Lys Gln | SEQ ID NO:84 | X |
| Val Phe Lys Gln Tyr | SEQ ID NO:85 | X |
| Phe Lys Gln Tyr Ala | SEQ ID NO:86 | X |
| Lys Gln Tyr Ala Asn | SEQ ID NO:87 | X |
| Gln Tyr Ala Asn Asp | SEQ ID NO:88 | X |
| Tyr Ala Asn Asp Asn | SEQ ID NO:89 | |
| Ala Asn Asp Asn Gly | SEQ ID NO:90 | |
| Asn Asp Asn Gly Val | SEQ ID NO:91 | |
| Asp Asn Gly Val Asp | SEQ ID NO:92 | |
| Asn Gly Val Asp Gly | SEQ ID NO:93 | |
| Gly Val Asp Gly Glu | SEQ ID NO:94 | |
| Val Asp Gly Glu Trp | SEQ ID NO:95 | |
| Asp Gly Glu Trp Thr | SEQ ID NO:96 | |
| Gly Glu Trp Thr Tyr | SEQ ID NO:97 | |
| Glu Trp Thr Tyr Asp | SEQ ID NO:98 | |
| Trp Thr Tyr Asp Asp | SEQ ID NO:99 | |
| Thr Tyr Asp Asp Ala | SEQ ID NO:100 | |
| Tyr Asp Asp Ala Thr | SEQ ID NO:101 | |
| Asp Asp Ala Thr Lys | SEQ ID NO:102 | |
| Asp Ala Thr Lys Thr | SEQ ID NO:103 | |
| Ala Thr Lys Thr Phe | SEQ ID NO:104 | |
| Thr Lys Thr Phe Thr | SEQ ID NO:105 | |
| Lys Thr Phe Thr Val | SEQ ID NO:106 | |
| Thr Phe Thr Val Thr | SEQ ID NO:107 | |
| Phe Thr Val Thr Glu | SEQ ID NO:108 | |

The total number of torsion angles and unique conformers for each pentapeptide is presented in Table 4. Strong α helical clusters were identified using the in vacuo free energy for the uncharged pentapeptides. Based on these results, the probabilities for charged pentapeptides 2–8, 14–35 and 44–52 were recalculated using free energies which included polarization and ionization energies. The refined probabilities were used to calculate α helical propensities for each residue according to the average AAA probability. The inclusion of rigorous solvation and ionization energies reduced the N-terminal helix to a short fragment of 4 residues, between residues 5–8, exhibiting average helix propensity above 90 percent. Furthermore, a depression in the helix propensity below 90 percent for both residues 49 and 50 effectively disrupts the formation of a potential C-terminal helix. One remaining extended helix survives between residues 23 and 31. To investigate the two remaining helices, additional free energy calculations were conducted for heptapeptides including residues 5–8 and 32–34 at core positions. The results indicate that the N-terminal helix does not form for the longer heptapeptides, and that the second helix extends to residue 34. These observations suggest that different oligopeptide systems may be useful for affirming the pentapeptide results. Experimentally, the immunoglobulin binding domain of Protein G exhibits one α helix between residues 22 and 35, which agrees well with the prediction of a helix between residues 23 and 34. The final results are presented in FIG. 14.

Table 4: Summary of pentapeptide information. The second column provides the number of dihedral angles for the peptide, while the third column indicates the total number of unique conformers identified during the ensemble generation of the uncharged pentapeptides.

TABLE 4

| SEQ ID NO: | DA | Unique |
|---|---|---|
| 57 | 40 | 11506 |
| 58 | 40 | 13998 |
| 59 | 41 | 17160 |
| 60 | 41 | 6373 |
| 61 | 36 | 13446 |
| 62 | 37 | 14089 |
| 63 | 36 | 10365 |
| 64 | 36 | 15659 |
| 65 | 38 | 15058 |
| 66 | 38 | 14563 |
| 67 | 37 | 13340 |
| 68 | 37 | 14899 |
| 69 | 36 | 14534 |
| 70 | 34 | 13604 |
| 71 | 38 | 16686 |
| 72 | 35 | 13942 |
| 73 | 35 | 13027 |
| 74 | 35 | 13508 |
| 75 | 33 | 11803 |
| 76 | 30 | 7966 |
| 77 | 32 | 9743 |
| 78 | 30 | 9296 |
| 79 | 31 | 9297 |
| 80 | 35 | 13341 |
| 81 | 37 | 13055 |
| 82 | 36 | 14895 |
| 83 | 40 | 16465 |
| 84 | 40 | 17392 |
| 85 | 38 | 14052 |
| 86 | 36 | 15207 |
| 87 | 37 | 15127 |
| 88 | 35 | 14520 |
| 89 | 34 | 13436 |
| 90 | 31 | 11423 |
| 91 | 33 | 14832 |
| 92 | 33 | 14796 |
| 93 | 30 | 13140 |

TABLE 4-continued

| SEQ ID NO: | DA | Unique |
|---|---|---|
| 94 | 31 | 11266 |
| 95 | 33 | 14842 |
| 96 | 33 | 15295 |
| 97 | 33 | 16180 |
| 98 | 36 | 16356 |
| 99 | 35 | 17710 |
| 100 | 34 | 13052 |
| 101 | 34 | 14942 |
| 102 | 36 | 15524 |
| 103 | 36 | 15206 |
| 104 | 35 | 14521 |
| 105 | 37 | 13870 |
| 106 | 37 | 14857 |
| 107 | 35 | 10579 |
| 108 | 36 | 14015 |

3. Chymotrysin Inhibitor, 3CI2

Like BPTI, chymotrypsin inhibitors are serine protease inhibitors. Chymotrypsin inhibitor 2 commonly refers to the potato I family of trypsin inhibitors, which has been resolved experimentally using both crystallographic and NMR methods. Neglecting the unstructured set of 1999. Like the immunoglobulin binding domain of protein G, the strongest consolidation of secondary structure is found in the α helix.

The decomposition of the truncated 63 residue chain of chymotrypsin inhibitor 2 results in a total of 59 overlapping pentapeptides, as presented in Table 5. The amino acid sequence for the 63 residue chain is:
KTEWPELVGKSVEEAKKVILQDKPEAQIIVLPVGTI-VTMEYRIDRVRLFVDKLDNIAQVPRVG<SEQ ID NO: 109>.

End groups corresponded to neutral amino groups at N termini and hydroxyl groups at C termini for all pentapeptides, excluding those with terminal Pro residues. Each pentapeptide is classified according to the conformational characteristics of the three central (core) residues. Based on the experimentally derived structure, Table 5 indicates that pentapeptides 10 through 18 possess core residues with full α helical structure.

Table 5: Pentapeptide sequences used for α helix prediction of Chymotrypsin Inhibitor. The second column assigns the identifier for each pentapeptide, while and (X) in the third column indicates the location, determined by experiment, of a helical core for the given sequence.

TABLE 5

| Pentapeptide | SEQ ID NO: | PDB |
|---|---|---|
| Lys Thr Glu Trp Pro | 110 | |
| Thr Glu Trp Pro Glu | 111 | |
| Glu Trp Pro Glu Leu | 112 | |
| Trp Pro Glu Leu Val | 113 | |
| Pro Glu Leu Val Gly | 114 | |
| Glu Leu Val Gly Lys | 115 | |
| Leu Val Gly Lys Ser | 116 | |
| Val Gly Lys Ser Val | 117 | |

TABLE 5-continued

| Pentapeptide | SEQ ID NO: | PDB |
|---|---|---|
| Gly Lys Ser Val Glu | 118 | |
| Lys Ser Val Glu Glu | 119 | X |
| Ser Val Glu Glu Ala | 120 | X |
| Val Glu Glu Ala Lys | 121 | X |
| Glu Glu Ala Lys Lys | 122 | X |
| Glu Ala Lys Lys Val | 123 | X |
| Ala Lys Lys Val Ile | 124 | X |
| Lys Lys Val Ile Leu | 125 | X |
| Lys Val Ile Leu Gln | 126 | X |
| Val Ile Leu Gln Asp | 127 | X |
| Ile Leu Gln Asp Lys | 128 | |
| Leu Gln Asp Lys Pro | 129 | |
| Gln Asp Lys Pro Glu | 130 | |
| Asp Lys Pro Glu Ala | 131 | |
| Lys Pro Glu Ala Gln | 132 | |
| Pro Glu Ala Gln Ile | 133 | |
| Glu Ala Gln Ile Ile | 134 | |
| Ala Gln Ile Ile Val | 135 | |
| Gln Ile Ile Val Leu | 136 | |
| Ile Ile Val Leu Pro | 137 | |
| Ile Val Leu Pro Val | 138 | |
| Val Pro Arg Val Gly | 139 | |
| Val Leu Pro Val Gly | 140 | |
| Leu Pro Val Gly Thr | 141 | |
| Pro Val Gly Thr Ile | 142 | |
| Val Gly Thr Ile Val | 143 | |
| Gly Thr Ile Val Thr | 144 | |
| Thr Ile Val Thr Met | 145 | |
| Ile Val Thr Met Glu | 146 | |
| Val Thr Met Glu Tyr | 147 | |
| Thr Met Glu Tyr Arg | 148 | |
| Met Glu Tyr Arg Ile | 149 | |
| Glu Tyr Arg Ile Asp | 150 | |
| Tyr Arg Ile Asp Arg | 151 | |
| Arg Ile Asp Arg Val | 152 | |
| Ile Asp Arg Val Arg | 153 | |
| Asp Arg Val Arg Leu | 154 | |
| Arg Val Arg Leu Phe | 155 | |
| Val Arg Leu Phe Val | 156 | |
| Arg Leu Phe Val Asp | 157 | |
| Leu Phe Val Asp Lys | 158 | |
| Phe Val Asp Lys Leu | 159 | |
| Val Asp Lys Leu Asp | 160 | |
| Asp Lys Leu Asp Asn | 161 | |
| Lys Leu Asp Asn Ile | 162 | |
| Leu Asp Asn Ile Ala | 163 | |
| Asp Asn Ile Ala Gln | 164 | |
| Asn Ile Ala Gln Val | 165 | |
| Ile Ala Gln Val Pro | 166 | |
| Ala Gln Val Pro Arg | 167 | |
| Gln Val Pro Arg Val | 168 | |

Figure 15:
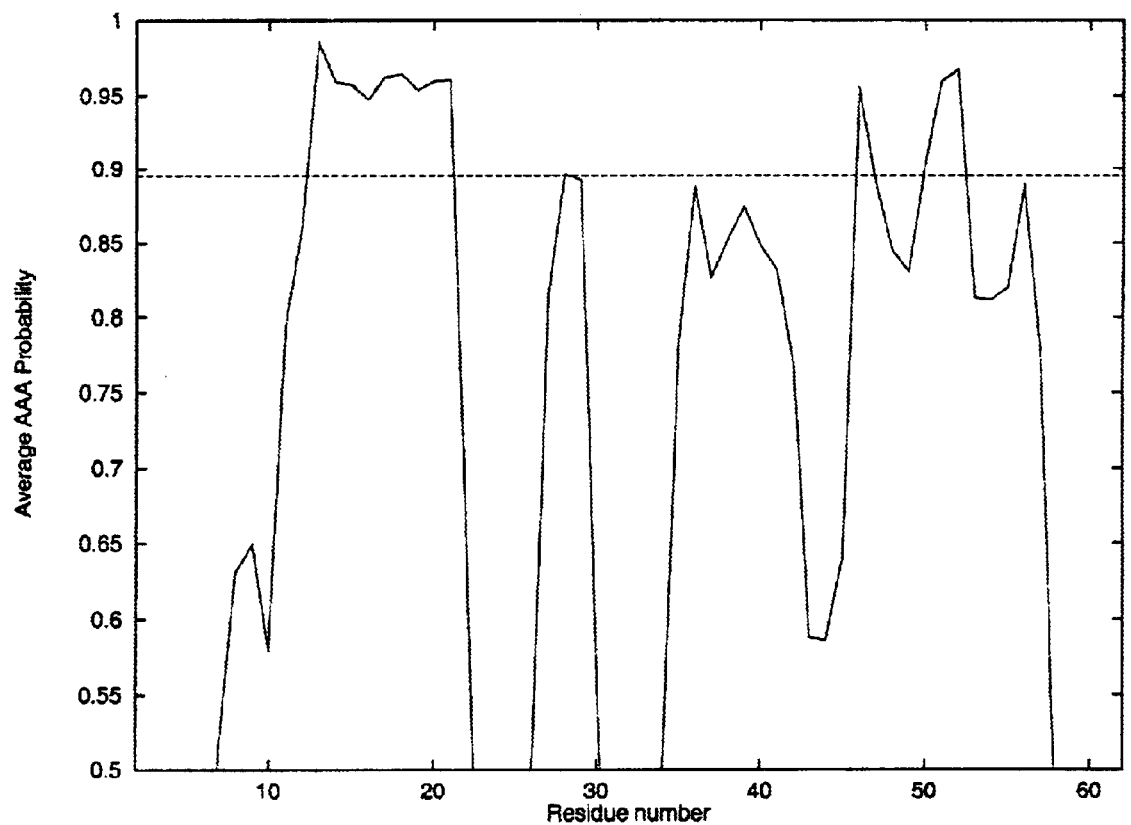
FIG. 15 shows a probability of α-helix formation of central three residues for chymotrypsin inhibitor, plotted versus central residue of each pentapeptide.

Table 6 presents the total number of torsion angles and unique conformers for each pentapeptide. Using the in vacuo free energy, the strongest α helical clusters were identified for uncharged pentapeptides 9 through 20. The C-terminal region, specifically between residues 45 and 55, also displayed relatively high AAA probabilities, although two small depressions below 75 percent disrupt the possibility for helix formation in this region. In addition, the region between residues 35 and 45, which corresponds to the reactive loop structure, does not produce helical conformers. Refined probabilities for pentapeptides 9 through 20 were used to calculate a helical propensities for each residue according to the average AAA probability. These results, as presented in FIG. 15, support the prediction of a single helix between residues 12 and 21. These results agree extremely well with those found experimentally.

Table 6: Summary of pentapeptide information. The second column provides the number of dihedral angles for the peptide, while the third column indicates the total number of unique conformers identified during the ensemble generation of the uncharged pentapeptides.

TABLE 6

| SEQ ID NO: | DA | Unique |
|---|---|---|
| 110 | 35 | 10298 |
| 111 | 33 | 11321 |
| 112 | 34 | 12697 |
| 113 | 33 | 14703 |
| 114 | 33 | 12990 |
| 115 | 37 | 13776 |
| 116 | 35 | 13654 |
| 117 | 34 | 10664 |
| 118 | 35 | 10727 |
| 119 | 39 | 15274 |
| 120 | 35 | 13712 |
| 121 | 38 | 13365 |
| 122 | 40 | 14972 |
| 123 | 39 | 13970 |
| 124 | 39 | 13485 |
| 125 | 42 | 16415 |

TABLE 6-continued

| SEQ ID NO: | DA | Unique |
|---|---|---|
| 126 | 41 | 17093 |
| 127 | 39 | 14896 |
| 128 | 41 | 15837 |
| 129 | 37 | 13871 |
| 130 | 36 | 12371 |
| 131 | 33 | 10227 |
| 132 | 34 | 13767 |
| 133 | 35 | 13498 |
| 134 | 38 | 12992 |
| 135 | 37 | 12585 |
| 136 | 40 | 15102 |
| 137 | 36 | 11470 |
| 138 | 34 | 9755 |
| 139 | 30 | 8804 |
| 140 | 30 | 11437 |
| 141 | 32 | 11628 |
| 142 | 34 | 11175 |
| 143 | 34 | 10990 |
| 144 | 38 | 13885 |
| 145 | 39 | 15161 |
| 146 | 38 | 15321 |
| 147 | 42 | 17316 |
| 148 | 43 | 16508 |
| 149 | 42 | 16825 |
| 150 | 45 | 20074 |
| 151 | 45 | 17963 |
| 152 | 45 | 17897 |
| 153 | 45 | 17573 |
| 154 | 44 | 18113 |
| 155 | 40 | 14218 |
| 156 | 40 | 16916 |
| 157 | 38 | 14668 |
| 158 | 38 | 16246 |
| 159 | 39 | 14241 |
| 160 | 39 | 15462 |
| 161 | 40 | 16039 |
| 162 | 36 | 12919 |
| 163 | 36 | 14734 |
| 164 | 36 | 13957 |
| 165 | 33 | 9773 |
| 166 | 35 | 11123 |
| 167 | 37 | 12567 |
| 168 | 33 | 11325 |

4. Comparison with Existing Methods

The results for the postulated superstructures were then compared to the PSIPRED method for secondary structure prediction. McGuffin et al., *Bioinformatics*, 16:404–405, 2000. PSIPRED utilizes two feed-forward neural networks to perform an analysis on output obtained from PSI—BLAST (Position Specific Iterated=13 BLAST). Altschul et al., *Nucleic Acids Res.*, 25:3389–3402, 1997. Cross validation of the method indicates that PSIPRED is capable of achieving an average Q3 score of nearly 77 percent, which is the highest result for any published secondary structure prediction methods. The predictions are based on a standard three state model to indicate the location of helix, strand and coil fragments for a given sequence.

Figure 14:
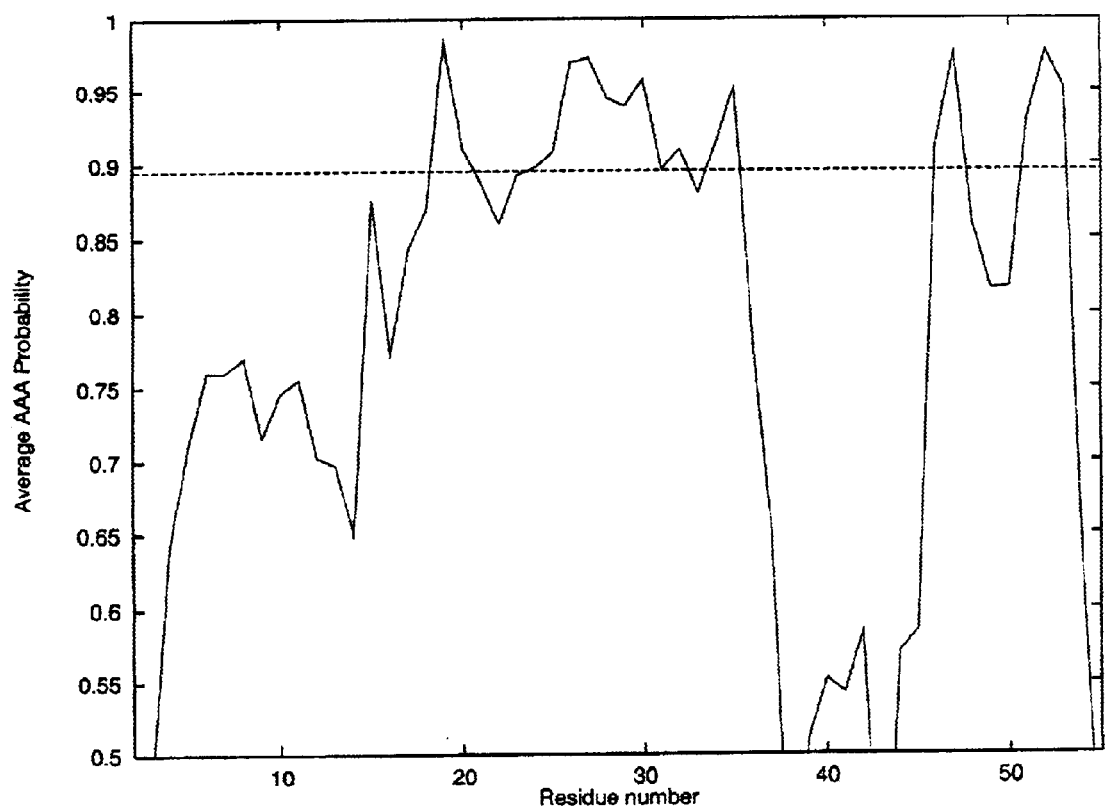
FIG. 14 shows a probability of α-helix formation of central three residues for immunoglobulin binding region of protein G, plotted versus central residue of each pentapeptide.

Qualitatively, the results of the PSIPRED method and the ab initio approach agree quite well in the prediction of helical segments for the three proteins studied here. In particular, the extended helix in each of the systems is accurately predicted with a high confidence level (an average of 8 out of 9 on a 0 to 9 scale) using PSIPRED. Two disagreements are evident between the two predictions, and both represent inaccuracies in the PSIPRED results. The first is a lack of the prediction of the small N-terminal helix between residues 2 and 5 for BPTI. The second is the weak prediction (confidence level less than 1) of an additional helix between residues 17 and 20 in the immunoglobulin binding domain of protein G. FIG. 14 exhibits a spike in the helix propensity for this region, although the conditions do not satisfy the criteria for assigning a helical segment.

5. Computational Complexity

The extension of our ab initio helix prediction approach to larger protein systems is facilitated through the use of distributed computing environments. The major expense of the overall approach involves multiple solutions of the nonlinear Poisson-Boltzmann equation for each conformation, which depends strongly on the number of ionizable groups. An estimate of the computational effort is made for a 128 processor (600 PIII) parallel machine running Linux.

For each oligopeptide, the set of in vacuo free energy calculations can be performed independently on single processors. To avoid significant idle time, the number of oligopeptides, which is on the order of the total number of residues in the sequence, should not exceed the number of available processors. As an example, a typical pentapeptide would require approximately 15 CPU hours on a single processor. On a 128 processor system, results for a full set of pentapeptides from a 68 residue sequence (or shorter) will complete in approximately 10 wallclock hours.

All additional calculations require the solution of the nonlinear Poisson-Boltzmann equation, which is carried out by finite difference routines implemented in the DELPHI package. Honig and Nicholls, *Science*, 268:11144–1149, 1995; Gilson and Honig, *Proteins*, 4:7, 1988. The calculation of $F_{solv}$ requires two calls to DELPHI, and the number of calls is independent of the number of titratable groups in the system. For each ionizable group six additional DELPHI calls are required, four reaction field calculations ($PS_i^+, PS_i^o, S_i^o, S_i^+$) and two permanent dipole calculations ($PS_i^+, PS_i^o$). Two of the six calculations involve only single residue conformations, rather than the full protein system. When multiple titratable groups are present, four additional DELPHI calls must be made for each pair of ionizable groups. The computational effort is summarized in Table 7.

Table 7: Total number of DELPHI calls required for calculation of $F_{solv}$, $\Delta G_j$ and $\Delta G_{jk}$ terms.

TABLE 7

| | No. ionizable groups | | | | | |
|---|---|---|---|---|---|---|
| | 1 | 2 | 3 | 4 | 5 | N |
| $F_{solv}$ | 2 | 2 | 2 | 2 | 2 | 2 |
| $\Delta G_j$ | 6 | 12 | 18 | 24 | 30 | 6N |
| $\Delta G_{jk}$ | 0 | 4 | 12 | 24 | 40 | 2N(N − 1) |
| Total | 8 | 18 | 32 | 50 | 72 | $2(N + 1)^2$ |

The set of DELPHI calls is performed for an ensemble of the lowest free energy conformers for each oligopeptide. For an ensemble of 5000 pentapeptide conformers the total CPU requirement is on the order about 0.5 wallclock hour on the 128 parallel processor machine. However, the computational requirements are dependent on the specific size and charge distribution of the system. When considering systems with multiple titration sites, the computational cost increases considerably. For a two titratable group pentapeptide, a system of 5000 conformers requires approximately 1.5 wallclock hours on a parallel machine, while approximately 3 wallclock hours is needed for a system with three ionizable groups.

When considering the total time to calculate helix propensities for a full protein sequence, DELPHI calculations are performed only for those segments with oligopeptides exhibiting strong helix propensities in the vacuum state are considered. For BPTI, 17 pentapeptides with ionizable side chains were included in this set. Overall, 1 day of wallclock time was required to perform the DELPHI calculations, in addition to about 1 day for the initial in vacuo free energy runs.

These values can also be used to estimate the total time to calculate free energies for oligopeptides of larger protein systems. A For the in vacuo free energy calculations the total wallclock time will always be 1 day as long as the number of processor exceeds the total number of oligopeptides, since each oligopeptide is run sequentially. When considering the DELPHI calculations, although the dependence is approximately linear, the actual result varies according to the number of residues with titratable side chains and their occurrence in the set of oligopeptides. If we consider a 100 residue sequence with a composition similar to BPTI, the number of wallclock days required for the DELPHI calculations will double for a 128 processor machine (2 days instead of 1). The time can be easily reduced to 1 wallclock day by doubling the number of available processors.

Example 2

Determination of Beta Strands and Sheets

1. Illustration of β-Strand Superstructure

The identification of β-strand superstructure is illustrated for several polypeptides, as shown in Tables 8 to 12. For the first three examples, the presence of helices was determined by the ab initio prediction method as described above, while the other helices were set according to the method of Kabsch and Sander, *Biopolymers*, 22:2577, 1983, as applied to the experimentally derived structure.

Table 8: Prediction of potential β strands for BPTI. The first row provides the single letter code for the amino acid sequence <SEQ ID NO:55>. The second row provides the classification of H,B,T,N residues. A contiguous block of X characters shows the predicted 3 strands, while S indicates a potential disulfide bridge forming residue, in the third row.

TABLE 8

| 1234567890 | 1234567890 | 1234567890 | 1234567890 | 1234567890 |
|---|---|---|---|---|
| RPDFCLEPPY | TGPCKARIIR | YFYNAKAGLC | QTFVYGGCRA | KRNNFKSAED |
| N--HNTTH | BTTHNBNHHN | HHHTBNBTHH | NBHHHTTHNB | NNTTHN-- |
| --S-- | -S-XXXX | XXX--XS | XXXXX-S- | ---- |

| 12345678 |
|---|
| CMRTCGGA |
| --HTTB |
| S-S- |

Table 9: Prediction of potential β strands for Protein G binding domain. The first row provides the single letter code for the amino acid sequence <SEQ ID NO:56>. The second row provides the classification of H,B,T,N residues. A contiguous block of X characters shows the predicted β strands in the third row.

TABLE 9

| 1234567890 | 1234567890 | 1234567890 | 1234567890 | 1234567890 |
|---|---|---|---|---|
| MTYKLILNGK | TLKGETTTEA | VDAATAEKVF | KQYANDNGVD | GEWTYDDATK |
| HBHNHHHTTN | BHNTNBBBNB | HT--- | --TTTHT | TNHBHTTBBN |
| XXXXXXX- | --XXXXX | X--- | ---- | -XXXX--X |

| 123456 |
|---|
| TFTVTE |
| BHBHBN |
| XXXXX- |

Table 10: Prediction of potential β strands for Chymotrypsin inhibitor. The first row provides the single letter code for the amino acid sequence <SEQ ID NO: 109>. The second row provides the classification of H,B,T,N residues. A contiguous block of X characters shows the predicted β strands in the third row.

TABLE 10

| 1234567890 | 1234567890 | 1234567890 | 1234567890 | 1234567890 |
|---|---|---|---|---|
| KTEWPELVGK | SVEEAKKVIL | QDKPEAQIIV | LPVGTIVTME | YRIDRVRLFV |
| NBNHTNHHTN | T--- | -NTNBNHHH | HTHTBHHBHN | HNHTNHNHHH |
| ---- | ---- | --XXXX | XXX-XXXXX | XXX-XXXXXX |

| 1234567890 | 123 | | | |
|---|---|---|---|---|
| DKLDNIAQVP | RVG | | | |
| TNHTTHBNHT | NHT | | | |
| --XXXX- | - | | | |

Table 11: Prediction of potential β strands for Small Nuclear Ribonucleoprotein Sm D3 (T0059 from CASP 3). The first row provides the single letter code for the amino acid sequence thereof:
MSIGVPIKVLHEAEGHIVTCETNTGEVYRGK-
LIEAEDNMNCQMSNITVTYRDGRVA-
QLEQVYIRGCKIRFLILPD <SEQ ID NO: 169>.

The second row provides the classification of H,B,T,N residues. A contiguous block of X characters shows the predicted β strands in the third row.

The superstructure based β strand predictions are summarized in Table 13. For BPTI two β strands are identified (i.e., 17–23 and 29–35), along with the 6 cystine residues belonging to potential disulfide bridges. Individual hydrophobic residues, such as residue 45, are also identified. For the binding domain of Protein G both the N-terminal and C-terminal domains, before and after the helix, provide two potential β strand segments (i.e., 1–7, 16–21, 42–45, 50–55). The same number of potential strands are predicted for Chymotrypsin Inhibitor 2 (i.e., 27–33, 36–43, 45–50,

TABLE 11

| 1234567890 | 1234567890 | 1234567890 | 1234567890 | 1234567890 |
|---|---|---|---|---|
| MSIGVPIKVL | HEAEGHIVTC | ETNTGEVYRG | KLIEAEDNMN | CQMSNITVTY |
| HTHT-- | -NTNHHBH | NBTBTNHHNT | NHHNBNTTHT | HNHTTHBHBH |
| ---- | --XXXXX | ---XXX- | XXX-XX | XXX-XXXXX |

| 1234567890 | 1234567890 | 12345 | | |
|---|---|---|---|---|
| RDGRVAQLEQ | VYIRGCKIRF | LILPD | | |
| NTTNHBNHNN | HHHN-HNH | HHHTT | | |
| X-XXXXX- | XXX--XXX | XXX- | | |

Table 12: Prediction of potential β strands for Cyanovirin-N (T0052 from CASP3). The first row provides the single letter code for the amino acid sequence thereof:
LGKFSQTCYNSAIQGSVLTSTCERTNGG-
YNTSSIDLNSVIENVDGSLKWQPSNFI-
ETCRNTQLAGSSELAAECKTRAQQ FVSTKINLD-
DHIANIDGTLKYE <SEQ ID NO: 170>.

The second row provides the classification of H,B,T,N residues. A contiguous block of X characters shows the predicted β strands, while S indicates a potential disulfide bridge forming residue, in the third row.

56–59), and it is significant to note that the second postulated β strand coincides with the reactive loop domain of the experimental structure. The predicted structures are also impressive for both the T0052 and T0059 sequences. The only major difference between the predicted and experimental β strand networks is the identification of an additional β strand (strand 6) for the superstructure of T0052.

Table 13: Postulated β strands from application of superstructure based β strand prediction approach. The N-terminal and C-terminal residue positions are given for each strand.

TABLE 12

| 1234567890 | 1234567890 | 1234567890 | 1234567890 | 1234567890 |
|---|---|---|---|---|
| LGKFSQTCYN | SAIQGSVLTS | TCERTNGGYN | TSSIDLNSVI | ENVDGSLKWQ |
| HTN--HHT | BBHNTTHHBB | BHNNBTTTHT | BBBHT-HH | NTHTTTHNHN |
| ---SXX | XXXX-XXXX | XSX--- | XXX--XX | X--XXXX |

| 1234567890 | 1234567890 | 1234567890 | 1234567890 | 1234567890 |
|---|---|---|---|---|
| PSNFIETCRN | TQLAGSSELA | AECKTRAQQF | VSTKINLDDH | IANIDGTLKY |
| TTTHHNBHNT | BNHBTTTNHB | BNHNBNBNNH | HBBNHT-N | HBTHTTBHNH |
| -XXXXSX- | -XXX-XXX | XXS--XX | XXXXX--X | XXXX-XXXX |

| 1 | | | | |
|---|---|---|---|---|
| E | | | | |
| N | | | | |
| - | | | | |

TABLE 13

| | N-Terminus | C-Terminus |
|---|---|---|
| BPTI | | |
| Strand 1 | 17 | 23 |
| Strand 2 | 29 | 35 |
| Protein G | | |
| Strand 1 | 1 | 7 |
| Strand 2 | 16 | 21 |
| Strand 3 | 42 | 45 |
| Strand 4 | 50 | 55 |
| Chymotrypsin | | |
| Strand 1 | 27 | 33 |
| Strand 2 | 36 | 43 |
| Strand 3 | 45 | 50 |
| Strand 4 | 56 | 59 |
| T0059 | | |
| Strand 1 | 16 | 20 |
| Strand 2 | 26 | 28 |
| Strand 3 | 31 | 33 |
| Strand 4 | 39 | 43 |
| Strand 5 | 46 | 51 |
| Strand 6 | 54 | 58 |
| Strand 7 | 61 | 63 |
| Strand 8 | 68 | 73 |
| T0052 | | |
| Strand 1 | 8 | 14 |
| Strand 2 | 17 | 23 |
| Strand 3 | 31 | 33 |
| Strand 4 | 39 | 41 |
| Strand 5 | 47 | 50 |
| Strand 6 | 54 | 59 |
| Strand 7 | 62 | 64 |
| Strand 8 | 68 | 73 |
| Strand 9 | 79 | 85 |
| Strand 10 | 90 | 94 |
| Strand 11 | 97 | 100 |

The application of the proposed β-sheet prediction approach relies on the identification of an appropriate hydrophobicity scale. Many attempts have been made to quantify hydrophobicity in terms of a single scale (Cornette et al., *J. Mol. Biol.*, 195:659, 1987), and the results have been controversial because different scales differ widely in the order in which the amino acids appear. This suggests that different scales may measure different properties more or less directly related to hydrophobicity. The proposed approach partially circumvents this problem in that the specification of the hydrophobic parameters applies only to those residues classified as hydrophobic. Therefore, there is no requirement that all amino acids be ordered in a linear way since the formulation deals with only the subset of hydrophobic residues. For illustrative purposes, the PRIFT hydrophobicity scale, which was recommended by Cornette et al., supra, is used. The values of the parameters are given in Table 14.

Table 14: Parameter values, $H_i$ for PRIFT hydrophobicity scale.

TABLE 14

| Residue | $H_i$ |
|---|---|
| Leu | 5.66 |
| Ile | 4.77 |
| Val | 4.67 |
| Phe | 4.44 |
| Met | 4.23 |
| Cys | 4.07 |
| Tyr | 3.23 |
| Trp | 1.04 |

2. BPTI

Both the residue-based and strand-based β sheet prediction methods were applied to bovine pancreatic trypsin inhibitor, BPTI, a small globular protein found in many tissues throughout the body. BPTI inhibits several of the serine protease proteins such as trypsin, kallikrein, chymotrypsin, and plasmin, and is a member of the pancreatic trypsin inhibitor (kunitz) family, which is a family of serine protease inhibitors. These proteins usually have conserved cysteine residues that participate in the formation of disulfide bonds. In particular, BPTI possesses three disulfide bonds, which are denoted as Cys5–Cys55, Cys14–Cys38, and Cys30–Cys51. The structure of the 58 amino acid residues chain of BPTI has been resolved through several methods, including X-ray crystallography (4PTI) (Deisenhofer and Steigemann, *Acta Crystallogr. Sect B*, 31:238–250, 1975) and a combination of X-ray and neutron diffraction experiments (5PTI) (Wlodawer et al., *J. Mol Biol.*, 180:301–329, 1984).

Table 15 classifies the hydrophobic residues according to their position in the sequence. The residue-to-residue contact formulation was applied to this set of hydrophobic residues through a two stage iteration. In the first iteration both disulfide bonding pairs and one antiparallel β sheet were identified. The subsequent stage predicted additional single residue-to-residue contacts. The results are summarized in Table 16.

Table 15: List of hydrophobic residues according to position in overall BPTI sequence. The classification identifies those residues belonging to predicted α-helical segments (A) and those that may form disulfide bridges (S).

TABLE 15

| Res | Num | Class | Res | Num | Class | Res | Num | Class |
|---|---|---|---|---|---|---|---|---|
| Phe | 4 | A | Cys | 5 | A, S | Leu | 6 | A |
| Tyr | 10 | | Cys | 14 | S | Ile | 18 | |
| Ile | 19 | | Tyr | 21 | | Phe | 22 | |
| Tyr | 23 | | Leu | 29 | | Cys | 30 | S |
| Phe | 33 | | Val | 34 | | Tyr | 35 | |
| Cys | 38 | S | Phe | 45 | | Cys | 51 | A, S |
| Met | 52 | A | Cys | 55 | A, S | | | |

Table 16: Results for residue contact formulation over 2 iterations for BPTI. The top three residue-to-residue contact solutions are given for each iteration. The overall best solution is given by the combined results of column 1.

TABLE 16

| 1 | | 2 | | 3 | |
|---|---|---|---|---|---|
| Iter 1 | | | | | |
| 5–55 | Cys-Cys | 5–51 | Cys-Cys | 5–38 | Cys-Cys |
| 14–38 | Cys-Cys | 14–38 | Cys-Cys | 14–55 | Cys-Cys |
| 30–51 | Cys-Cys | 30–55 | Cys-Cys | 30–51 | Cys-Cys |
| 18–34 | Ile-Val | 18–34 | Ile-Val | 18–34 | Ile-Val |
| 19–33 | Ile-Phe | 19–33 | Ile-Phe | 19–33 | Ile-Phe |
| 23–29 | Tyr-Leu | 23–29 | Tyr-Leu | 23–29 | Tyr-Leu |
| Iter 2 | | | | | |
| 22–45 | Phe-Phe | 21–45 | Tyr-Phe | 10–22 | Tyr-Phe |

Figure 16:
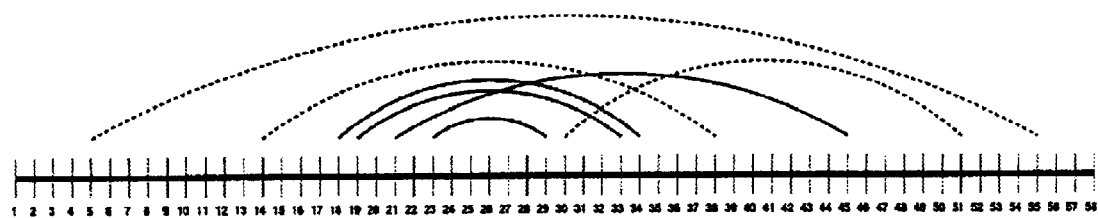
FIG. 16 shows a contact diagram for global optimum of residue contact formulation for BPTI. Disulfide bridges contacts are represented by dashed lines. The PRIFT hydrophobicity scale is used in this analysis (based on an extensive comparative study of several scales for the detection of amphipathic structures [Cornette et al., *J. Mol. Biol.* 195, 659 (1987)]), although several additional hydrophobicity scales were considered [Rose et al., Science 229, 834 (1985); Karplus, *Protein Science* 6, 1302 (1997)] and provided consistent results with those shown above.

The results indicate that the formation of an antiparallel β sheet defined by contacts between residues 18–34, 19–33 and 23–29 dominates the best three solutions for the first iteration. The difference between these solutions is the ordering of the three disulfide bridges, which alter the objective function through the addition of the $H_{ij}^{add}$ terms. For this example, the global optimum corresponds to the naturally defined configuration. Since the formation of the same β sheet is a common element of all three solutions, the results of the second iteration are identical for each case. Each solution represents a single residue contact, with the best solution predicting the expected proximity between residues 22 and 45. A contact diagram for the global optimum, which represents a combination of the results for both iterations, is given in FIG. 16.

The application of the strand-based formulation (Formulation 1) provides results in agreement with the residue-based formulation. As Table 8 shows, the strand identification protocol produces two distinct strands (residues 17–23 and residues 29–35), which correlate exactly to the hydrophobic contact domains provided by the first iteration of the residue contact formulation. For BPTI, inclusion of strand-to-strand contact energies is superfluous since the two strands define only one potential match. However, the combination of strand definitions and the $y_{ij}$ based objective function (Formulation 3) can be used to simultaneously predict disulfide bridge formation, β sheet formation and the formation of individual residue-to-residue contacts. The global optimum solution is provided in Table 17.

Table 17: Results for strand based formulation applied to BPTI using only residue-to-residue contact energies.

TABLE 17

| Strands | 1–2 | (17–23)–(29–35) |
|---|---|---|
| Residues | 5–55 | Cys-Cys |
|  | 14–38 | Cys-Cys |
|  | 30–51 | Cys-Cys |
|  | 18–34 | Ile-Val |
|  | 19–33 | Ile-Phe |
|  | 23–29 | Tyr-Leu |
|  | 22–45 | Phe-Phe |

3. Protein G Binding Domain

Protein G is a small globular protein produced by several Streptococcal species. The proteins are composed of two or three nearly identical domains of about 55 amino acids each. The system considered here is the immunoglobulin-binding domain from streptococcal protein G, a 56 amino acid polypeptide. The structure contains an efficiently packed hydrophobic core between a four-stranded β-sheet and a four-turn α-helix with an overall secondary structure of ββαββ. The formation of the β-sheet consists of two β hairpin turns, each connecting antiparallel strands. The first and last strands combine to form the final parallel β sheet to give the four-stranded configuration.

Table 18 provides the classification of hydrophobic residues according to their position in the sequence. The residue-based formulation was applied to this set of hydrophobic residues through a two stage iteration. The sequence is first partitioned into two such that the helix bisects the two subsequences. First, the formulation is used to identify an antiparallel sheet for the C-terminal half. For the second iteration, the entire sequence is considered, and a second β-sheet joining the two halves is identified. The global optimum result is summarized in Table 19.

Table 18: List of hydrophobic residues according to position in overall Immunoglobulin binding domain sequence. The classification identifies those residues belonging to predicted α-helical segments (A).

TABLE 18

| Res | Num | Class | Res | Num | Class | Res | Num | Class |
|---|---|---|---|---|---|---|---|---|
| Met | 1 |  | Tyr | 3 |  | Leu | 5 |  |
| Ile | 6 |  | Leu | 7 |  | Leu | 12 |  |
| Val | 21 |  | Val | 29 | A | Phe | 30 | A |
| Tyr | 33 | A | Val | 39 |  | Trp | 43 |  |
| Tyr | 45 |  | Phe | 52 |  | Val | 54 |  |

Table 19: Global optimum results for residue-based formulation as applied to Immunoglobulin binding domain of Protein G over 2 iterations.

TABLE 19

| Iter 1 | |
|---|---|
| 43–54 | Trp-Val |
| 45–52 | Tyr-Phe |
| Iter 2 | |
| 5–52 | Leu-Phe |
| 7–54 | Leu-Val |

Figure 17:
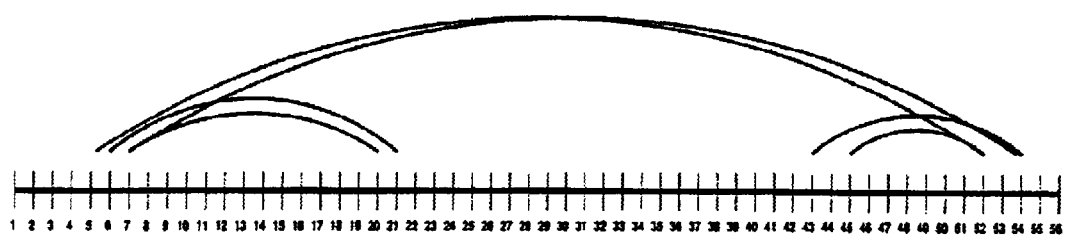
FIG. 17 shows a contact diagram for global optimum of strand-based formulation for Immunoglobulin binding domain of Protein G.

The identification of a more complete β-sheet configuration is obtained via the application of the strand-based formulation. The set of postulated β-strands consists of four potential strands, as shown in Table 10. Strands 1 and 2 are located before the helix, and encompass residues 1 through 7 and residue 16 through 21, respectively. The two C-terminal strands, strands 3 and 4, include residues 42 through 45 and residues 50 through 55, respectively. In particular, Formulation 1 predicts a global optimum configuration consistent with the experimental structure; that is, strands 1 and 2, 1 and 4 and 3 and 4 represent the strand-to-strand matches in the β sheet configuration. The results from Formulation 3 identify the residue matches between the strands, along with the same strand matches. In addition to the residue matches shown in Table 19, this prediction provides two contacts between strands 1 and 2, which corresponds to the proximity of residues 6 and 21 and 7 and 20. Although the match between 7 and 20 does not represent a true hydrophobic-hydrophobic contact, the presence of an alanine residue at position 20 provides a potential hydrophobic-bridge contact for the formation of this antiparallel β sheet. A schematic of the full set of residue contacts is shown in FIG. 17.

4. Chymotrypsin Inhibitor

Like BPTI, chymotrypsin inhibitors are serine protease inhibitors. Chymotrypsin inhibitor 2 commonly refers to the potato I family of trypsin inhibitors, which has been resolved experimentally using both crystallographic and NMR methods. Neglecting the unstructured set of residues near the N-terminus, the truncated 63 residue chain has a morphology consisting of several β strands, a helix and a reactive loop. The order of these secondary structural elements follows: strands, helix, strand, reactive loop, strands. The largest strands combine to form a packed hydrophobic core around the helix.

The hydrophobic residues are classified according to their position in the sequence in Table 15. The residue-to-residue contact formulation was applied to this set of hydrophobic residues for one iteration, which led to the identification of a parallel β sheet. The results are summarized in Table 21. An important observation is that the resulting β-sheet does not involve any residues belonging to the reactive loop. In addition, the second best solution also identifies an alternative β sheet configuration between similar regions of the sequence.

Table 20: List of hydrophobic residues according to position in overall Chymotrypsin Inhibitor sequence. The classification identifies those residues belonging to predicted α-helical segments (A).

TABLE 20

| Res | Num | Class | Res | Num | Class | Res | Num | Class |
|-----|-----|-------|-----|-----|-------|-----|-----|-------|
| Trp | 4   |       | Leu | 7   |       | Val | 8   |       |
| Val | 12  | A     | Val | 18  | A     | Ile | 19  | A     |
| Leu | 20  | A     | Ile | 28  |       | Ile | 29  |       |
| Val | 30  |       | Leu | 31  |       | Val | 33  |       |
| Ile | 36  |       | Val | 37  |       | Met | 39  |       |
| Tyr | 41  |       | Ile | 43  |       | Val | 46  |       |
| Leu | 48  |       | Phe | 49  |       | Val | 50  |       |
| Leu | 53  |       | Ile | 56  |       | Val | 59  |       |
| Val | 61  |       |     |     |       |     |     |       |

Table 21: Results for residue contact formulation over one iteration for Chymotrypsin Inhibitor 2. The top two residue-to-residue contact solutions are given.

TABLE 21

| 1 | | 2 | |
|---|---|---|---|
| Iter 1 | | | |
| 29–46 | Ile-Val | 28–46 | Ile-Val |
| 31–48 | Leu-Leu | 30–48 | Val-Leu |
| 33–50 | Val-Val | 31–49 | Leu-Phe |

Figure 18:
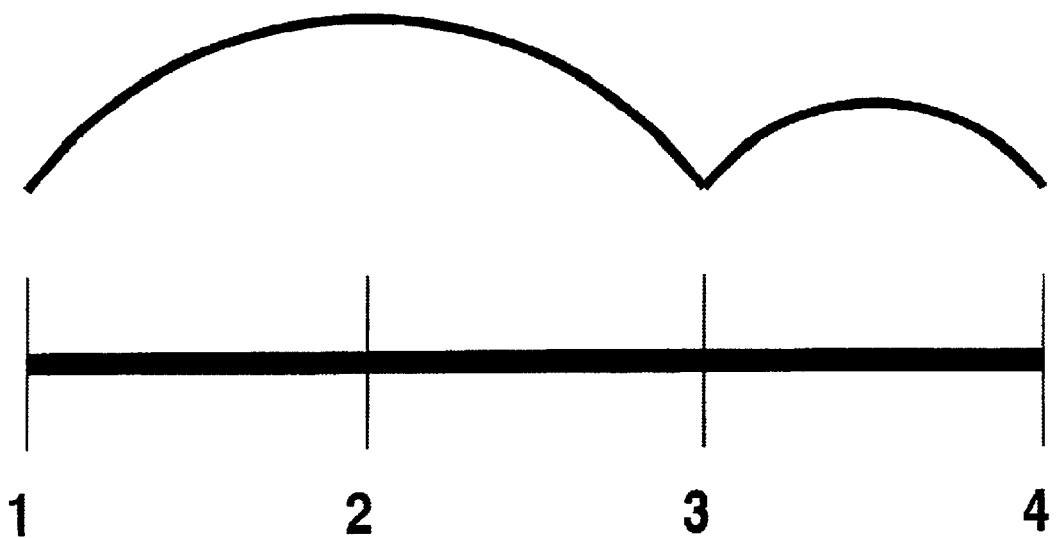
FIG. 18 shows a contact diagram for global optimum of strand-based formulation for Chymotrypsin Inhibitor.

The results of the strand-based formulation verify and expound on the predictions from the residue-based formulation. The superstructure of postulated strands include four independent strands, as shown in Table 10. Using Formulation 1, a parallel strand-to-strand contact is identified between strands 1 and 3, while strands 3 and 4 also provide a second match (see FIG. 18). Again, the reactive loop, which corresponds to the second postulated strand, does not participate in the overall β sheet configuration. This is due to the relatively low strand weight for postulated strand 2 when compared to the three other postulated strands. Formulation 3 predicts the same β sheet arrangement, and, in addition to the residue-based prediction results given in column 1 of Table 21, provides the residue-to-residue contacts of 46 to 59 and 49 to 56, which delimit the strand 3 and 4 match.

5. Small Nuclear Ribonucleoprotein Sm D3 (T0059 from CASP 3)

The target structure of the Sm D3 protein is consistent with the common core of typical Sm proteins. This structure involves a short N-terminal helix and a set of β strands forming antiparallel β sheets that fold upon itself to produce a barrel like structure. The overall topology resembles the common SH3 fold.

Figure 19:
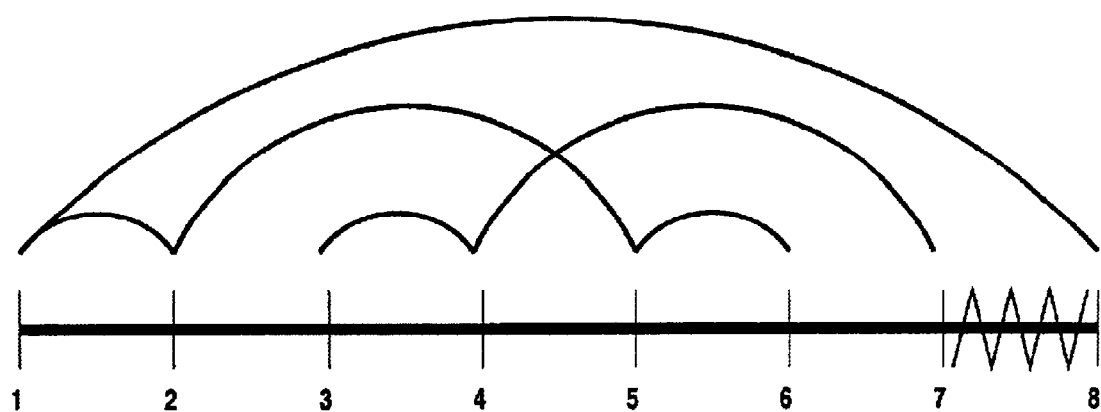
FIG. 19 shows a contact diagram for global optimum of residue contact formulation for Small Nuclear Ribonucleoprotein Sm D3 (T0059 from CASP 3). Disulfide bridges contacts are represented by dashed lines.

For systems such as T0059, the direct application of the Formulation 1 of the strand based models rapidly generates full β sheet configurations. For T0059, the location of the postulated strands shown in Table 11, replicates the experimental β strand arrangement. In the solution of Formulation 1 multiple global optima are identified, with one of the seven solutions corresponding to the true β sheet configuration shown in FIG. 19.

Table 22 shows the strand-to-strand contacts for all seven global optima. Several common characteristics are evident. For example, strand connections always form between strand 1 and strands 2 and 8. In addition, since the strand probabilities are additive, the number of occurences of each strand is the same in each solution. Each solution can then be used as a starting point for further analysis.

Table 22: Strand-to-strand contacts for multiple global optima of T0059.

TABLE 22

| Optimum | 1 | 2 | 3 | 4 | 5 | 6 | 7 |
|---------|---|---|---|---|---|---|---|
| Match 1 | 1–2 | 1–2 | 1–2 | 1–2 | 1–2 | 1–2 | 1–2 |
| Match 2 | 1–8 | 1–8 | 1–8 | 1–8 | 1–8 | 1–8 | 1–8 |
| Match 3 | 2–5 | 2–6 | 2–4 | 2–4 | 2–4 | 2–4 | 2–5 |
| Match 4 | 3–4 | 3–4 | 3–7 | 3–6 | 3–5 | 3–5 | 3–4 |
| Match 5 | 5–6 | 4–5 | 4–5 | 4–5 | 4–6 | 4–7 | 4–6 |
| Match 6 | 4–7 | 5–7 | 5–6 | 5–7 | 5–7 | 5–6 | 5–7 |

6. Cyanovirin-N (T0052 from CASP3)

Cyanovirin-N is a unique, 101 amino acid protein and a constituent of a cultured cyanobacterium, *Nostoc ellipsosporum*. Cynaovirin-N potently and irreversibly inactivates diverse primary strains of HIV-1, including M-tropic forms of HIV, as well as T-tropic and dual-tropic forms. The protein also blocks cell-to-cell transmission of HIV infection and is directly virucidal with an apparently extremely high binding affinity such that it interacts in an unusual manner with the viral envelope. The structure exhibits a novel β architecture, consisting of a double β sandwich. In addition, the sequence exhibits an internal symmetry with homologous N-terminal and C-terminal halves. Each domain consists of two β sheet configurations, one with three β strands starting from the N-terminus and the other with two β strands.

As with T0059, Formulation 1 of the strand-based models is used to predict a full β sheet architecture. The postulated β strand superstructure has strand 6 as an extra β strand in the postulated network.

Figure 20:
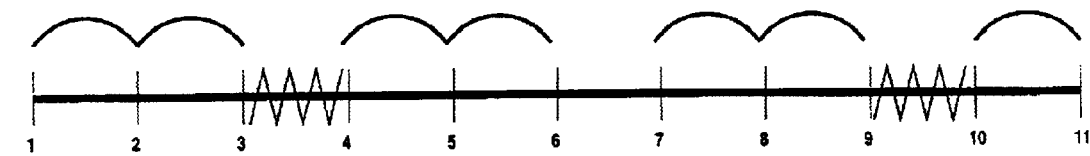
FIG. 20 shows a contact diagram for global optimum of residue contact formulation for Cyanovirin-N (T0052 from CASP 3). Disulfide bridges contacts are represented by dashed lines.

The application of Formulation 1 predicts a global optimum configuration similar to that of the experimentally determined β sheet architecture, as shown in FIG. 20. Specifically, the network provides four β sheet sandwiches, three with three β strands and one with two β strands. The minor inconsistency between the predicted and experimental configurations corresponds to the placement of the additional postulated strand, which is appended to the second β sheet sandwich. Therefore, without knowledge of possible symmetry conditions, the overall predicted structure is very similar to experimental results.

7. Comparison with Existing Methods

The results for the postulated superstructures were then compared to the PSIPRED method for secondary structure prediction. PSIPRED utilizes two feed-forward neural networks to perform an analysis on output obtained from PSI—BLAST (Position Specific Iterated—BLAST). Cross validation of the method indicates that PSIPRED is capable of achieving an average Q3 score of nearly 77 percent, which is the highest result for any published secondary structure prediction methods. The predictions are based on a standard three state model to indicate the location of helix, strand and coil fragments for a given sequence. It is important to note that PSIPRED can only predict the location of secondary structure in the overall sequence. In contrast, the presented ab initio approach predicts the location of potential β-strands as well the configuration of the overall β-sheet network.

In general, the PSIPRED β strand predictions are significantly different from those presented in Tables 8 to 12. The best correspondence is observed for BPTI, the Immunoglobulin binding domain of Protein G and Chymotrypsin Inhibitor 2. For these sequences, the superstructure based and PSIPRED predicted β strands typically overlap, with small deviations in the demarcation of the beginning and end residues of the strands. The PSIPRED results are summarized in Table 23. In the case of the Protein G binding domain protein, PSIPRED predicts a significantly shorter second β strand that is closer to the N-terminus, while for Chymotrypsin Inhibitor 2 an additional β strand is identified before the helix. In most cases, the confidence factor is extremely low.

Table 23: β strand predictions, along with average confidence factor (0 low, 9 high) for predicted strand, obtained from PSIPRED.

TABLE 23

|  | N-terminus | C-terminus | Confidence |
|---|---|---|---|
| BPTI |  |  |  |
| Strand 1 | 19 | 24 | 7.9 |
| Strand 2 | 29 | 35 | 5.4 |
| Protein G |  |  |  |
| Strand 1 | 2 | 7 | 7.3 |
| Strand 2 | 10 | 12 | 3.0 |
| Strand 3 | 43 | 44 | 2.0 |
| Strand 4 | 51 | 54 | 3.8 |
| Chymotrypsin |  |  |  |
| Strand 1 | 7 | 8 | 3.0 |
| Strand 2 | 27 | 32 | 8.0 |
| Strand 3 | 36 | 39 | 3.8 |
| Strand 4 | 45 | 50 | 8.2 |
| Strand 5 | 56 | 57 | 3.0 |

For the two longer protein sequences, the results from the two approaches are more disparate. In contrast to the eight postulated strands for the superstructure based approach, the PSIPRED method predicts only six β strands for Sm D3 protein. However, further analysis reveals that the reduction in the number of strands is due to the consolidation of two sets of strands; in particular, strands 2 and 3, and strands 4 and 5. For the novel β architecture of Cyanovirin-N the sparisty of the PSIPRED results are inexplicable and are directly attributable to the database dependence of the approach. This is further evidenced by the low confidence factor for the prediction of the strands. In total, only partial segments from 6 out of the 11 β strands predicted by the superstructure based approach are identified.

8. Parametric Analysis

To gauge the robustness of the approach, the formulations were also tested with several different parameter sets. The values of the hydrophobic parameters for five additional sets are provided in Table 24.

Table 24: Hydrophobic parameter set values. For each parameter set the rank, from highest to lowest, of the residue is provided in the following column.

TABLE 24

| Residue | 1 |  | 2 |  | 3 |  | 4 |  | 5 |  |
|---|---|---|---|---|---|---|---|---|---|---|
| Leu | 4.68 | 4 | 5.55 | 4 | 4.68 | 5 | 3.27 | 5 | 4.10 | 2 |
| Ile | 4.95 | 2 | 6.05 | 3 | 4.94 | 4 | 4.02 | 2 | 3.88 | 3 |
| Val | 3.36 | 7 | 4.38 | 7 | 4.03 | 6 | 3.52 | 4 | 3.38 | 6 |
| Phe | 4.92 | 3 | 6.33 | 1 | 5.97 | 1 | 4.02 | 2 | 3.46 | 4 |
| Met | 3.38 | 6 | 6.22 | 2 | 4.55 | 6 | 3.27 | 5 | 3.43 | 5 |
| Cys | 4.24 | 5 | 4.80 | 5 | 5.45 | 3 | 4.77 | 1 | 1.20 | 8 |
| Tyr | 2.64 | 8 | 1.96 | 8 | 2.99 | 7 | 1.01 | 8 | 2.81 | 7 |
| Trp | 6.19 | 1 | 4.42 | 6 | 5.84 | 2 | 3.27 | 5 | 4.11 | 1 |

Example 3

Derivation of Restraints and Prediction of Polypeptide Tertiary Structure

The global optimization algorithm was tested on Compstatin, a synthetic 13-residue (ICVVQDWGUHRCT) cyclic peptide (disulfide bridge between the $Cys^2$ and $Cys^{12}$ residues) that binds to C3 (third component of complement) and inhibits complement activation. Two-dimensional NMR techniques (Morikis et al., *Protein Sci.*, 7:619–627, 1998) yield a total of 30 backbone sequential (including $H^\beta$—backbone), 23 medium and long range (including disulfide) and 82 intra-residue NOE restraints. In addition, 7 φ angle and 2 $_{\chi 1}$ angle dihedral restraints are available. In Morikis et al., supra, traditional distance geometry-simulated annealing protocol was utilized to minimize the associated target function in the Cartesian coordinate space using the program X-PLOR. NOE distance and dihedral angle restraints were modeled using a quadratic square well potential, while van der Waals overlaps were prevented through the use of a simple quartic potential function.

The NMR refinement protocols resulted in a family of 21 structures with similar geometries for the $Gln^5-Gly^8$ region. A representative structure was obtained by averaging the coordinates of the individually refined structures and then subjecting this structure to further refinement to release geometric strain produced by the averaging process. The formation of a type I β-turn was identified as a common characteristic for these structures.

1. Local Minimization

The consistency of the ensemble of Compstatin solution structures was determined by evaluating distance restraints for each of the original 21 structures (accession number 1a1p at the Brookhaven Protein Data Bank, http://www.pdb.bnl.gov), as well as the average Compstatin conformation. In considering distance restraints, only backbone sequential and medium/long range NOEs were considered. That is, the 82 intra-residue restraints were neglected since they are less likely to effect the overall fold of the Compstatin peptide. This results in a total of 52 restraints, with an additional restraint on the distance between the sulfur atoms forming the disulfide bridge. In order to quantify these results the violation energy, $E_{VIO}$, which can be calculated by summing Equations 3 and 4, was calculated for each of the original PDB structures. In these calculations, the value of the weighting factor ($A_j$) was assumed to be constant and set equal to 50 kcal/mol/Å$^2$.

Figure 21:
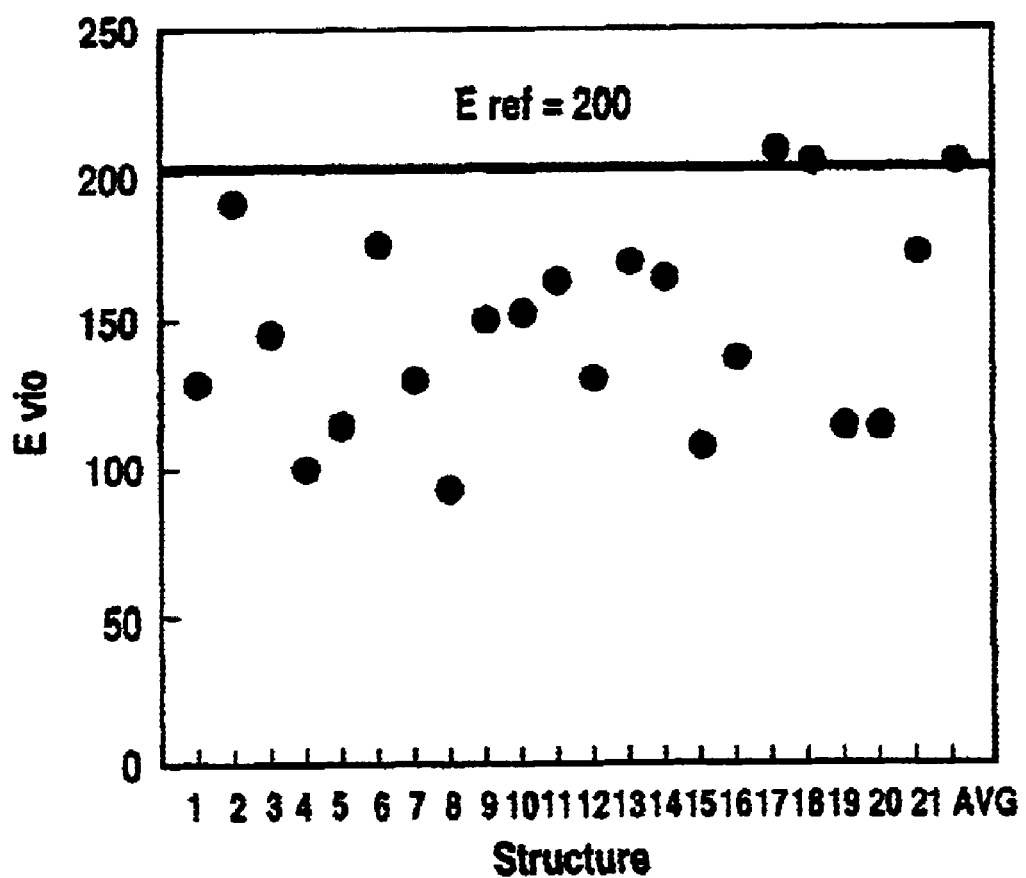
FIG. 21 shows violation energy, $E_{VIO}$, for original Compstatin PDB structures.

The results of the analysis, shown graphically in FIG. 21, indicate that the average structure ([Compstatin]) possesses the third largest violation energy, whereas the smallest value is provided by structure 8 (<Compstatin>$_8$) These quantities provide a range of comparison for violation energies and were used to set the constraint parameter, $E^{ref}$, to 200 kcal/mol. This value is chosen so that the sum of the violation energies will necessarily result in an improvement over the violation energy for the average Compstatin structure.

To measure the performance of the proposed global optimization approach, the ensemble and average Compstatin structures (<Compstatin> and [Compstatin]) were then used as starting points for local minimization. Since these calculations are performed in the torsion angle space, which requires fixing bond lengths and bond angles to equilibrium values, the corresponding Compstatin PDB structures could only be used to derive torsion angle values. These dihedral angles were then used as input to directly evaluate the corresponding force field energy. Differences in bond lengths and bond angles propagate through the generation of the corresponding ECEPP/3 structure, which produces an inherent RMSD between the PDB structure and the ECEPP/3 generated structure. For example, when using the set of dihedral angles calculated from the [Compstatin]

Figure 22:
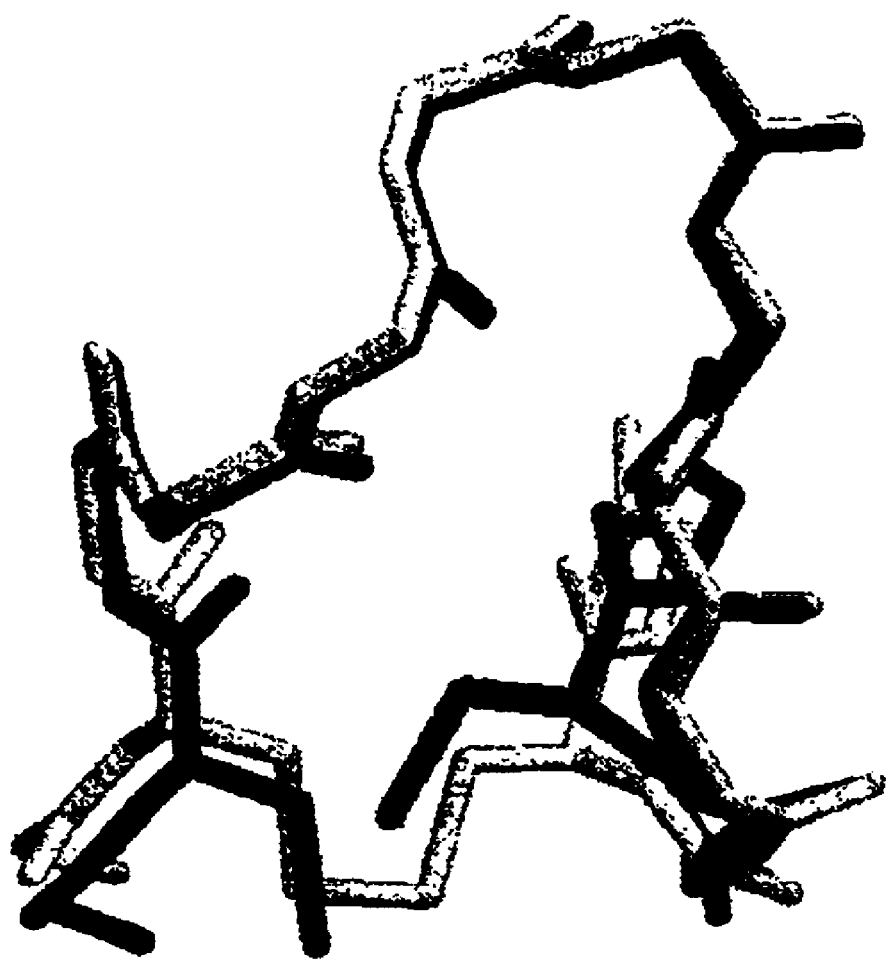
FIG. 22 shows a superposition of [Compstatin]$_{Orig}$ structure (in light grey) and corresponding ECEPP/3 structure (in black) using calculated dihedral angles ([Compstatin]$_{ECEPP}$)

PDB, the ECEPP/3 structure possesses a 0.581 Å all atom RMSD (all heavy atoms in backbone and side chains) with respect to the original [Compstatin] structure, with a corresponding ECEPP/3 energy of 519.2 kcal/mol. In addition, due to the differences in bond lengths and angles, the total distance violation for the ECEPP/3 structure ([Compstatin]$_{ECEPP}$) increases from 6.9 to 8.7 Å, which results in a subsequent increase in violation energy to 315 kcal/mol. The superposition of the original and ECEPP/3 [Compstatin] conformations is shown in FIG. 22.

Figure 23:
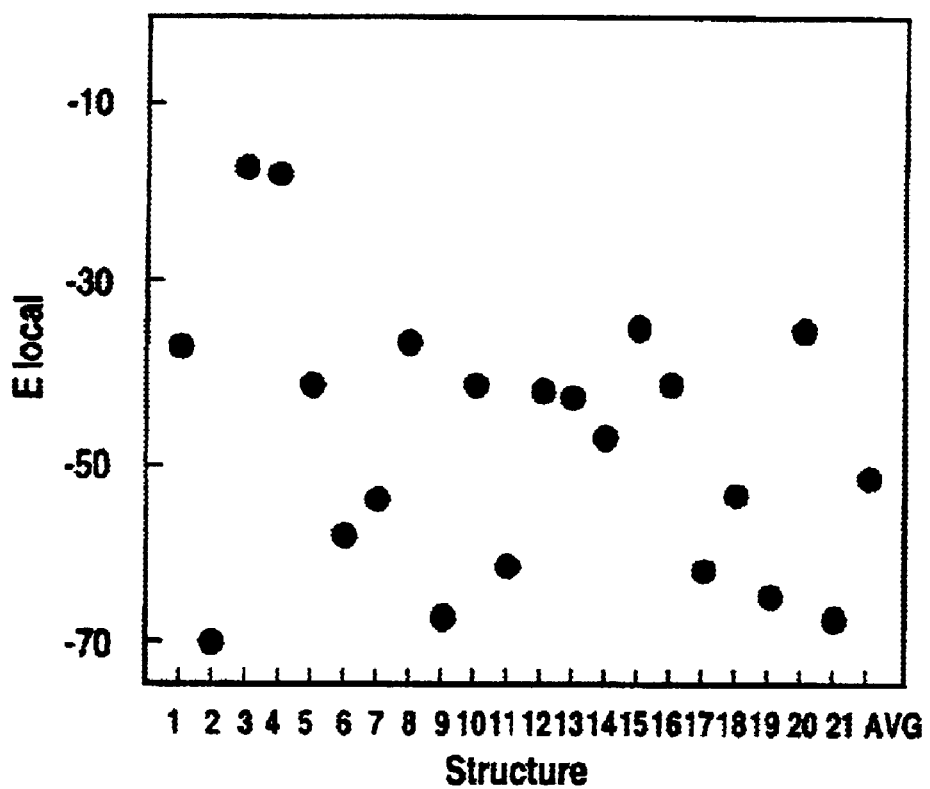
FIG. 23 shows locally minimized energy, $E_{ECEPP/3}$, for Compstatin structures.

Due to the relatively large distance violations and energies obtained after transformation of PDB to PACK (ECEPP/3) structures, the 22 structures were then subjected to local minimization. The problem formulation for local minimization uses the set of 53 restraints for the constraint function, a constant 50 kcal/mol/Å weighting factor ($A_f$) and a constraint parameter, $E^{ref}$, equal to 200 kcal/mol. In all cases, the corresponding violation energy reached the upper bound value of 200 kcal/mol. The corresponding total distance violations increased, with an average value of 6.766 Å. The smallest distance violation (5.873 Å) was reported for structure number 10 (<Compstatin>$_{10}^{Local}$), whereas the corresponding energy for this structure (−41.685 kcal/mol) was only slightly above the average energy of −47.75 kcal/mol. The lowest energy structures (−71.613 for <Compstatin>$_2^{Local}$, −68.704 kcal/mol for <Compstatin>$_{21}^{Local}$, −67.653 kcal/mol for <Compstatin>$_9^{Local}$) provided above average values for total distance violation (6.963 Å, 6.832 Å, 7.120 Å, respectively). In addition, the conformation obtained from the average Compstatin structure ([Compstatin]) exhibited near average values for energy (−52.283 kcal/mol) and total distance violations (6.392 Å). The range of ECEPP/3 energies after local minimization are shown in FIG. 23.

The structural characteristics of these locally minimized structures were quantified using RMSD (root mean squared deviation) calculations. For the original PDB structures, comparison with the average Compstatin structure provided RMSD values between 1–2 Å for only backbone atoms. As expected, these structures possess common structural features. However, when comparing original PDB structures and their locally minimized counterparts, most RMSD values are larger than 2 Å, indicating that significant conformational change occur during local minimization. This is due to both the reduced set of NOE restraints in the constraint function and the role of the detailed energy force field. In contrast, the RMSD values for the β-turn region remain consistently low when comparing the original PDB structures to their locally minimized counterparts. These results indicate that the β-turn is a conserved structural feature, even with the addition of the detailed energy model.

2. Global Minimization

The constrained global optimization approach was first applied to Compstatin structure prediction without the use of TAD. A subset of 26 (all ϕ and ψ) torsion angle, from a total of 73, were treated globally, while the remaining were allowed to vary locally. As was the case for local minimization, the same set of restraints were used to formulate the nonlinear constraint, with a constant 50 kcal/mo/Å weighting factor and a constraint parameter equal to 200 kcal/mol. The lowest energy structure satisfying the constraint functions provided an ECEPP/3 energy of −85.71 kcal/mol, an energy value more than 15 kcal/mol lower than those values provided by local minimization. The global minimization required approximately 40 CPU hours on a HP C160. The total distance violation equaled 6.690 Å which is near the average distance violation for the local minimum structures.

Figure 24:
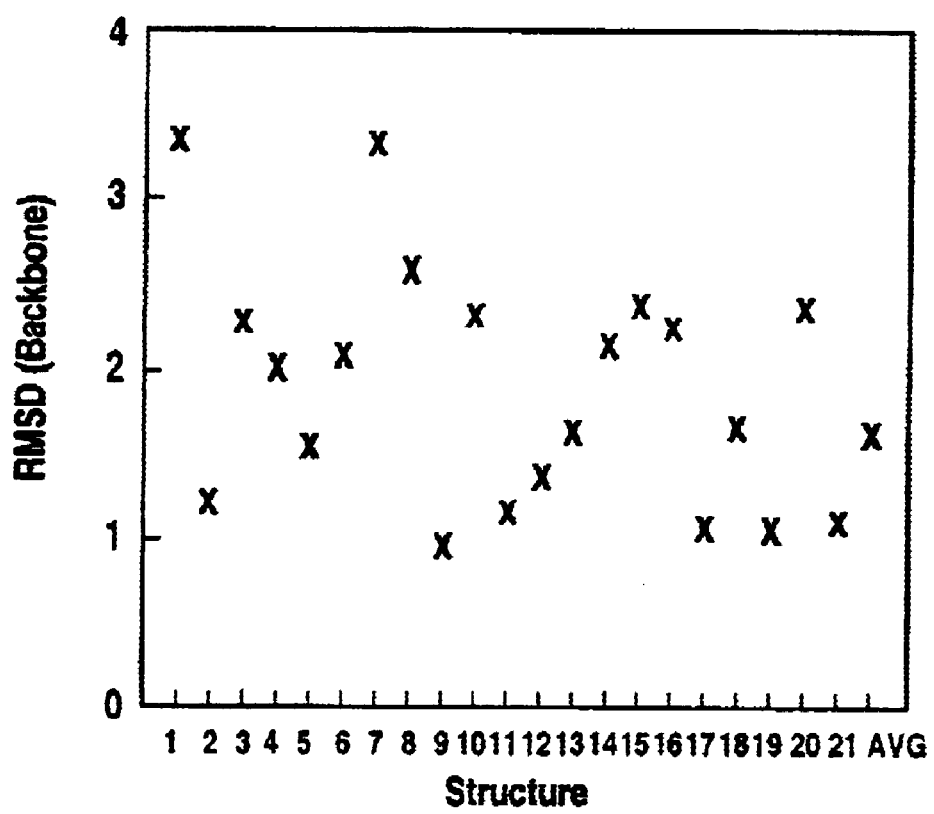
FIG. 24 shows RMSD values for backbone when comparing global minimum energy structure to locally minimized PDB structures.
Figure 25:
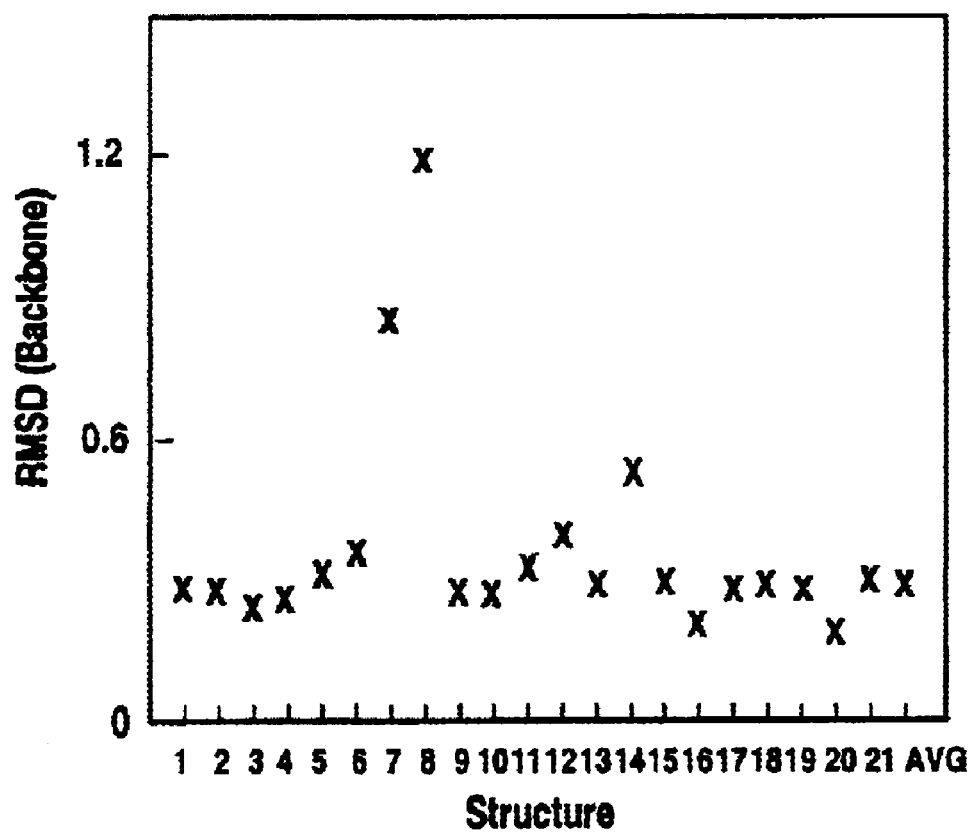
FIG. 25 shows RMSD values for $Gln^5$-$Gly^8$ backbone when comparing global minimum energy structure to locally minimized PDB structures.
Figure 26A:
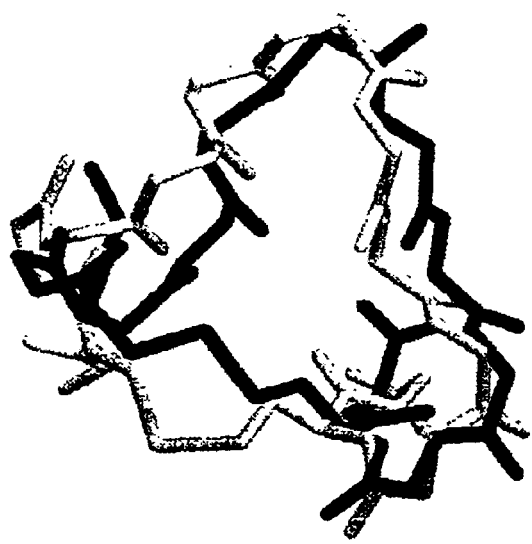
FIG. 26A shows the full backbone atom structure, while FIG. 26B compares only the β-turn region.
Figure 26B:
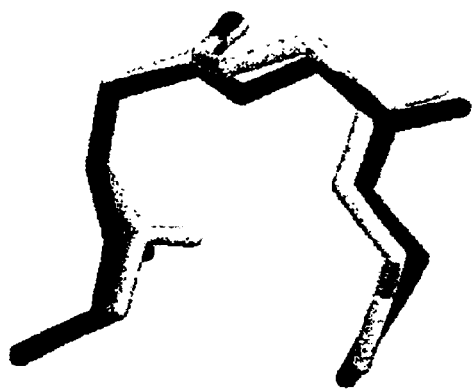
FIG. 26 shows superposition of global minimum (in black) and [Compstatin]$^{Local}$ (in light grey) structures.

RMSD calculations were performed to again quantify the structural differences between the global minimum energy structure and the other Compstatin structures. RMSD values between the full backbone and the β-turn segments of the 22 locally minimized PDB structures and the global minimum energy structure are plotted in FIGS. 24 and 25, respectively. When comparing full backbone RMSD values, the <Compstatin>$_9^{Local}$, <Compstatin>$_{21}^{Local}$, <Compstatin>$_{19}^{Local}$ and <Compstatin>$_{17}^{Local}$ provide the best agreement with the global minimum energy structure. These structures also correspond to four of the lowest energy local minimum, indicating that some of the lowest energy conformers exhibit similar backbone structural characteristics. In contrast, the lowest energy local minimum, <Compstatin>$_2^{Local}$, is less similar to the global minimum energy structure. For the ,β-turn segment, the correlation between low RMSD values and low energy local minima does not exist. This observation, coupled with the relatively low RMSD values between all structures, indicates that the β-turn structure is a characteristic for all conformers, including the global minimum energy structure. Plots for superpositioning (backbone atoms) of the average local minimum energy structure [Compstatin]$^{Local}$ and the global minimum energy structure are given in FIG. 26.

3. Global Optimization and Torsion Angle Dynamics

The modified constrained global optimization approach was also applied to the Compstatin structure prediction problem using the same constraint function and parameters. The goal of introducing TAD as a component of the upper bound solution approach is to increase the number of feasible points available for initialization of the constrained local minimization. Initially TAD is used in combination with simple van der Waals overlap restraints to drive the distance violations to zero. Taken independently, this methodology is comparable to the typical implementation of TAD for NMR structure prediction. *J. Mol. Biol.*, 273:283–298, 1997.

To gauge the performance of the combined αBB and TAD constrained approach, a comparison was made to an independent TAD method (DYANA, see Güntert, supra) for solving distance restraint problems. The same dihedral angle and 53 medium and long range distance restraints were considered, along with additional distance restraints to prevent van der Waals overlaps. The coupled simulated annealing/TAD protocol was applied to a starting sample of 1000 randomly generated structures, from which a subset consisting of 20 conformers exhibiting the best target values were used to initialize a second set of runs. The five conformations with the best target function values were selected for further analysis, including initialization for constrained local minimizations with $E_{ECEPP/3}$. The DYANA conformers satisfy the corresponding constraint, although their energy values are more than 70 kcal/mol higher than that of the global minimum energy structure. An analysis of the structural characteristics also indicates that the type I β-turn does not form along the Gln$^5$–Gly$^8$ b backbone for these structures. These results reflect the potential deficiencies of the independent TAD algorithm; that is, the simplified force field term is insufficient for sparse sets of distance restraints.

Figure 27:
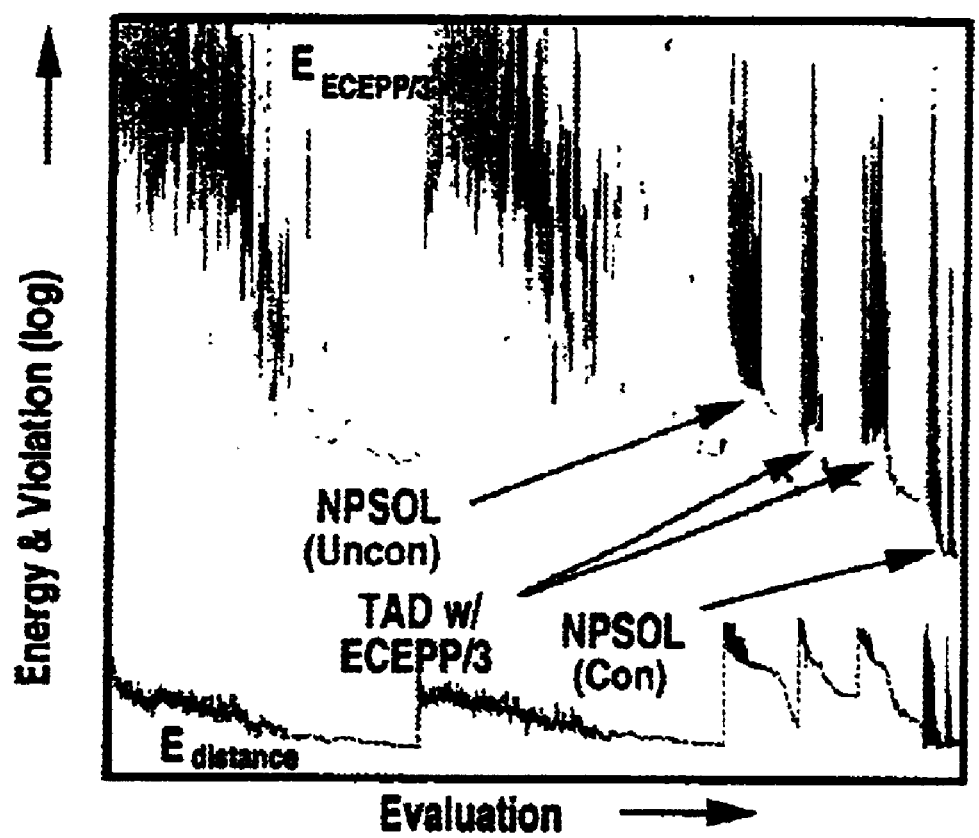
FIG. 27 shows a log plot of $E_{ECEPP/3}$ and $E^{distance}$ during a typical solution to the upper bounding problem for C3.

The use of TAD in the context of the global optimization approach surmounts this difficulty by using an iterative TAD scheme with two forms of the target function. The first set of TAD runs focuses on the reduction of the distance violations, while employing a simplified forcefield in the form of additional distance restraints to avoid atomic overlaps. This approach mimics the effects of a typical TAD approach for structure prediction. To ensure that these conformers provide low energy, this step is then followed by unconstrained minimization with a hybrid distance and ECEPP/3 energy objective function. If the ECEPP/3 energy is acceptably low, the algorithm proceeds to the constrained local minimization step, otherwise an iterative set of TAD runs are performed with readjustment of the relative weight of the distance and ECEPP/3 terms. FIG. 27 shows a typical sequence for both the ECEPP/3 and distance violations energy during one solution of the upper bounding problem for Compstatin.

Figure 28:
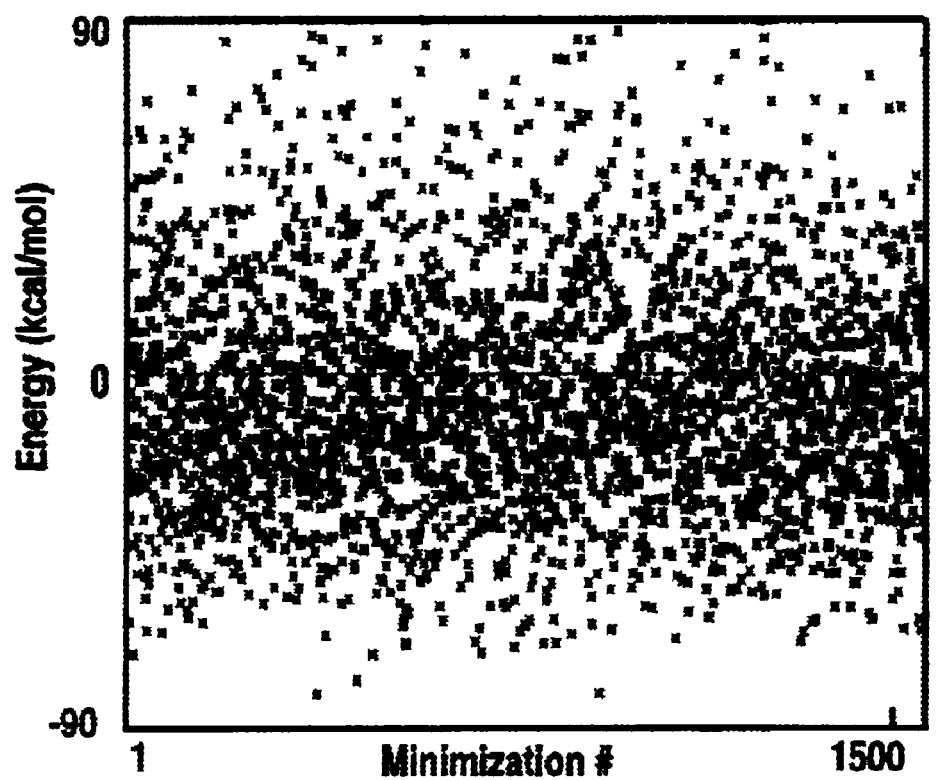
FIG. 28 shows energy values for Compstatin conformers obtained from combined constrained global optimization and TAD algorithm.

The results of the combined constrained global optimization and TAD algorithm can be assessed by examining the sequence of ECEPP/3 energies obtained from the solution of the upper bounding problems, as depicted in FIG. 28. When compared to the original algorithm, the TAD implementation augments the number of feasible starting points by more than a factor of two. This enhancement leads to earlier identification of low energy conformers. In particular, conformers with energies less than −70 kcal/mol, and thus lower in energy than the locally minimized PDB structures, are identified within the first 10 iterations of the global optimization approach. This property has important algorithmic implications, including the ability to fathom regions based on the current estimate of the global minimum. In general, the TAD enhanced search provides more consistent and denser population of low energy conformers.

Both experimental and theoretical methods exist for the prediction of protein structures. In both cases, additional restraints on the molecular system can be derived and used to formulate a nonconvex optimization problem. In this work, the traditional unconstrained problem was recast as a constrained global optimization problem, and applied to protein structure prediction using NMR data. Both the formulation and solution approach of this method differ from traditional techniques, which generally rely on the optimization of penalty-type target function using SA/MD protocols.

As a first step, the penalty type restraint functions were replaced by nonlinear constraints, which can be individually enumerated for all or subsets of the distance restraints. In addition, the objective function was transformed to a full atom force field potential, a modification that should be particularly useful for systems possessing sparse set of restraints. To solve this reformulated molecular structure prediction problem the concepts of a deterministic global optimization approach, αBB, were applied. This methodology can be used to develop theoretical guarantees for convergence to the global minimum of nonconvex constrained problems. The algorithm was further enhanced by modifying the upper bounding solution approach to include an iterative scheme involving TAD.

The approach was applied to the Compstatin structure prediction problem using both the original TAD approach and the coupled αBB-TAD approach. When considering basic structural features, such as the formation of a type I β-turn, the predicted structure was found to agree with results based on X-PLOR. However, constrained global optimization was able to identify conformers with significantly lower energies than those obtained from either local minimization or independent TAD algorithms. In particular, the coupled αBB-TAD implementation consistently produced dense populations of low energy conformers.

4. Application to BPTI Tertiary Structure Prediction

Figure 29:
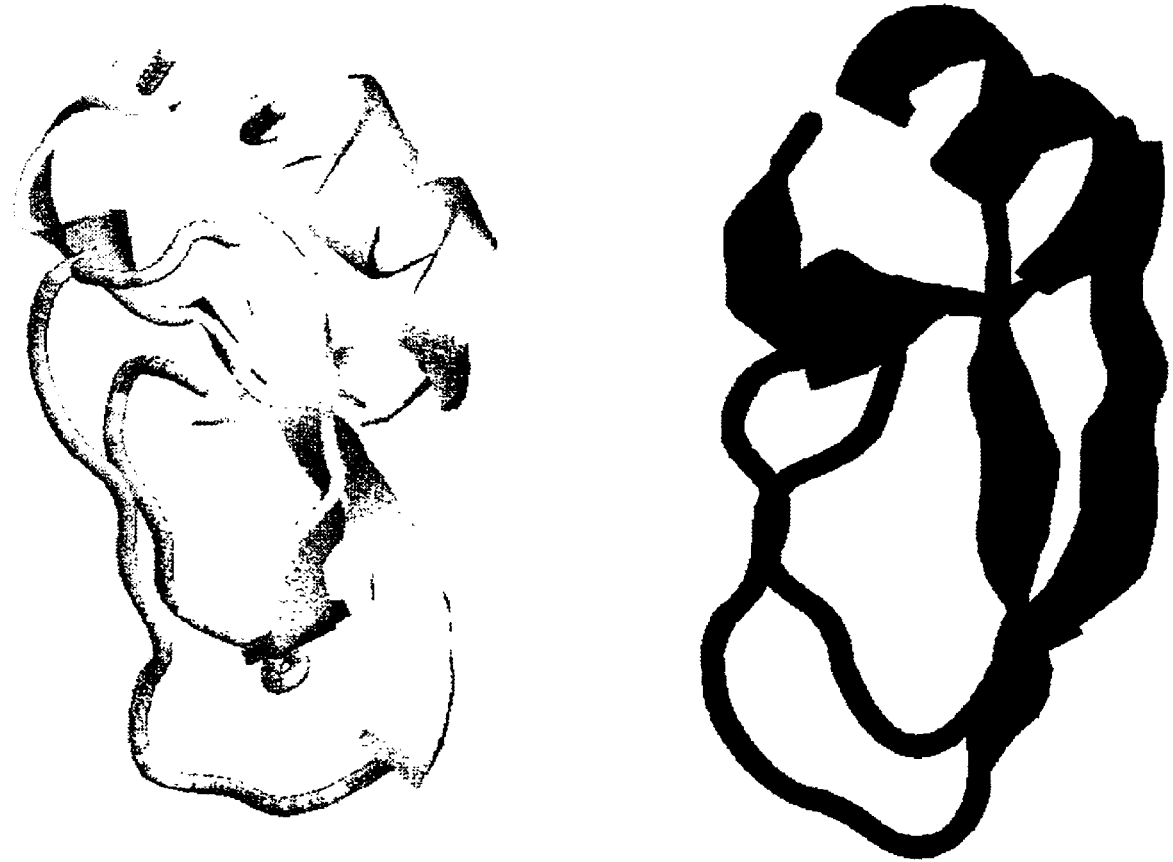
FIG. 29 shows a comparison of predicted tertiary structure (in black) of BPTI and experimentally derived structure (in grey). The structures begin with the N-termini at the upper right hand corner of the figure and end with the C-termini at the upper left hand corner of the figure.
Figure 6:
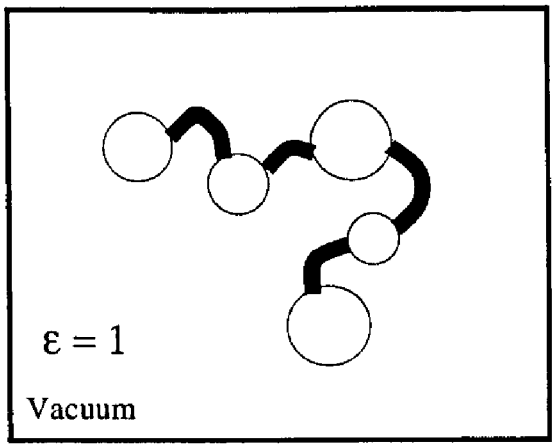
Figure 6:
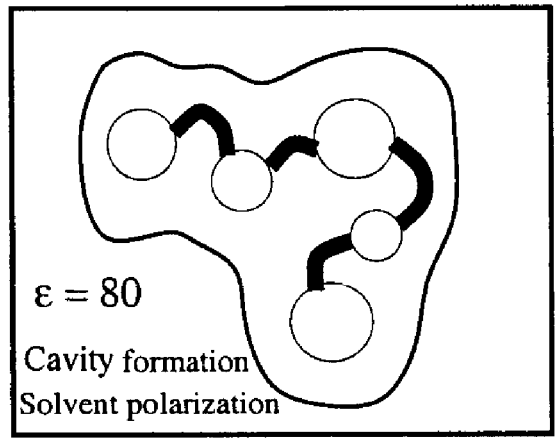
Figure 6:
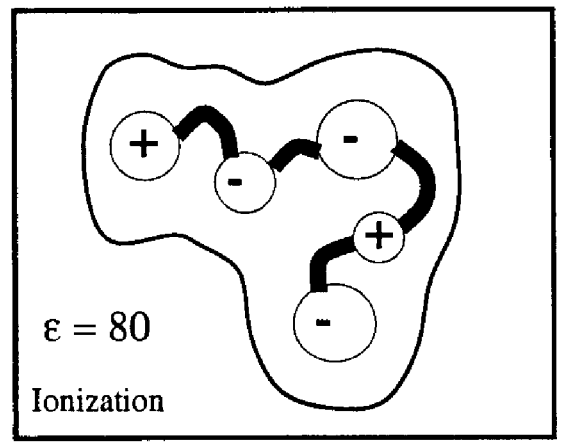

For the BPTI tertiary structure, the α-helix and β-sheet prediction results were used to bound dihedral angles for 30 of the 58 total residues. Residues 2–5 and 47–54 were constrained to the helical φ-ψ region ([−85, −55] for Φ, [−50, −10] for ψ), while the β-strands between residues 17–23, 29–35 and 44–46 were assigned φ-ψ bounds consistent with extended conformations ([−155, −75] for φ, [110, 180] for ψ). Distance restraints included 32 lower and upper $C^\alpha$–$C^\alpha$ distance restraints representing the predicted α-helix (5.5–6.5 Å) and β-sheet (4.5–6.5 Å) configuration, as well as six additional restraints (2.01–2.03 Å for sulfur atoms) to enforce the disulfide bridge network. During the course of the global optimization search, the branch and bound tree was formed by partitioning domains belonging to selected backbone variables of the undefined (coil) residues, while the remaining variables were treated locally. A significant sample of low energy structures with $C^\alpha$ RMSD (root mean squared deviation) values below 6.0 Å was identified along with the global minimum energy structure. The lowest energy structure, with an energy of −428.0 kcal/mol, also provided the best superposition with the crystallographic structure, with a 4.0 Å RMSD (see FIG. 29). Individual comparisons of the two helical, three strand and three loop segments demonstrated larger RMSD values for loops, undoubtedly a result of the lack of restraint information for these segments.

Although preferred embodiments of the subject invention have been described in some detail, it is understood that variations can be made without departing from the spirit and the scope of the invention as defined by the appended claims.

We claim:

1. A method of determining the existence and location of alpha helix regions of a polypeptide having an amino acid sequence by classifying individual residues in the overall sequence as helical or non-helical comprising:

(a) defining a first segment of said amino acid sequence having a length, between 5 and about 15 residues;

(b) partitioning the amino acid sequence into overlapping segments such that consecutive segments possess common core of at least four amino acid residues;

(c) for overlapping segments comprising the common core, before "performing atomistic modeling " performing atomistic modeling upon each segment to assay the free energy of each segment;

(d) generating an ensemble of low energy conformations for each segment;

(e) adjusting the ensemble for each segment to reflect a determination of entropic and free energy contributions for each segment;

(f) modifying the ensemble for each segment to reflect the contributions to free energy accorded by at least one of cavity formation, solvation, and ionization;

(g) ascertaining the equilibrium probabilities for helical clusters in each of the overlapping segments.

(h) determining probability for each residue of being involved in an alpha helix region from the average of equilibrium probabilities of those overlapping segments in which the residue constitutes a core position.

2. The method of claim 1 wherein the defining of further segments is performed iteratively and subsequent steps (c) through (h) are performed on all segments thus defined.

3. The method of claim 1, wherein each segment has a length of 5 amino acid residues.

4. The method of claim 1, wherein each segment has a length of 7 amino acid residues.

5. The method of claim 1, wherein each segment has a length of 9 amino acid residues.

6. The method of claim 2, wherein each segment has a length of 5 amino acid residues.

7. The method of claim 2, wherein each segment has a length of 7 amino acid residues.

8. The method of claim 2, wherein each segment has a length of 9 amino acid residues.

9. The method of any of claims 1–8, wherein the atomistic modeling is performed with a force field.

10. The method of any of claims 1–8, wherein the force field is an Empirical Conformational Energy Program for Peptides/3 (ECEPP/3) force field.

* * * * *

UNITED STATES PATENT AND TRADEMARK OFFICE
CERTIFICATE OF CORRECTION

PATENT NO.     : 6,832,162 B2
DATED          : December 14, 2004
INVENTOR(S)    : Christodoulos A. Floudas et al.

It is certified that error appears in the above-identified patent and that said Letters Patent is hereby corrected as shown below:

Title page,
Item [56], References Cited, OTHER PUBLICATIONS:
"Adjiman C. et al." reference (third occurrence), after "vol. 22," insert -- No. 9, --.
"Baldwin R. et al." reference (second occurrence), delete "77-73." and insert -- 77-83. --.
"Bryant, Z. et al." reference, delete "α-Hairpin" and insert -- β-Hairpin --.
"Gilson M. et al." reference (second occurrence), delete " "Calculating" and insert
-- "Calculation of --.
"Gronenborn, A. et al." reference, delete "immunoglobulin" and insert -- immunoglobin --.
"Güntert, P. et al." reference, delete " "Torison" and insert -- Torsion --.
"Jackson, S. et al." reference, delete "2:" and insert -- 2. --.
"Kabsch, W. et al." reference, delete "receognition" and insert -- recognition --.
"Pande, V. et al." reference, delete "aβ-hairpin" and insert -- a β-hairpin --.
"Yang, A. et al." reference, delete "$Pk_aS$" and insert -- $pK_aS$ --.

Figure 6:
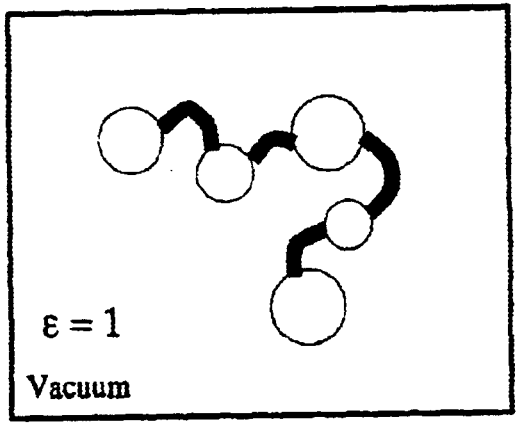
FIG. 6 shows an overall thermodynamic process of calculating the free energy for a system undergoing the transition from an isolated to a solvated and ionized environment.
Figure 6:
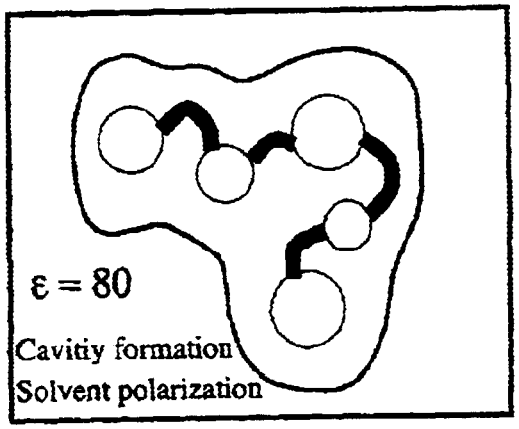
Figure 6:
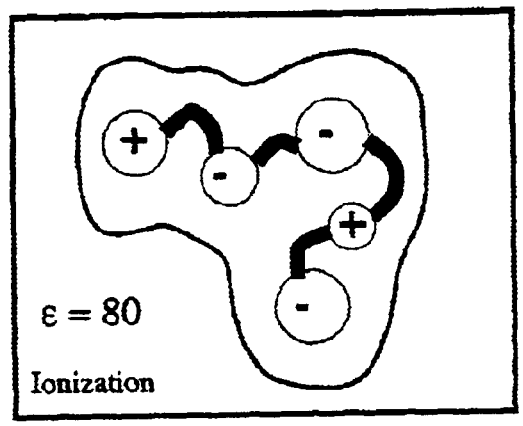

Drawings,
FIG. 6, delete "Cavitiy" and insert -- Cavity --. A replacement sheet for Figure 6 is attached.

Column 1,
Line 8, before "No. R01 GM52032," insert -- Grant --.

Column 2,
Line 34, delete "Nemethy" and insert -- Némethy --.

Column 3,
Lines 22-24, delete " $F_{total}F_{vac}^{har}+F_{cavity}+F_{solv}+F_{ionize}$, " and insert -- $F_{total} = F_{vac}^{har} + F_{cavity} + F_{solv} + F_{ionize}$, --.

Line 25, delete "$F_{sol}$" and insert -- $F_{solv}$ --.

Column 4,
Lines 33-34, delete " $[(\Sigma_{k, P(i) \leq P(k) \leq P(j)} H_k)/P(j)-P(i))]$. " and insert -- $[(\Sigma_{k, P(i) \leq P(k) \leq P(j)} H_k)/P(j) - P(i))]$. --.

Lines 36-40, delete " $\max \sum_i \sum_{j, P(i)+2 < P(j)} (H_i + H_j + H_{ij}^{add}) y_{ij}$ " and insert -- $\max' \sum_i \sum_{j, P(i)+2 < P(j)} (H_i + H_j + H_{ij}^{add}) y_{ij}$ --.

UNITED STATES PATENT AND TRADEMARK OFFICE
CERTIFICATE OF CORRECTION

PATENT NO. : 6,832,162 B2
DATED : December 14, 2004
INVENTOR(S) : Christodoulos A. Floudas et al.

It is certified that error appears in the above-identified patent and that said Letters Patent is hereby corrected as shown below:

Column 4 (cont'd),
Lines 46-48, delete " $y_{ij}+y_{kl} \leq 1 \, \forall P(i)+P(j) \neq P(k)+P(l), y_{ij}$ OR $y_{kl \notin \{Cys, Cys\}}$ " and insert -- $y_{ij}+y_{kl} \leq 1 \, \forall P(i)+P(j) \neq P(k)+P(l), y_{ij}$ OR $y_{kl} \notin \{Cys, Cys\}$ --.

Lines 56-57, delete " $y_{ij}+y_{kl} \leq 1 \, \forall P(k)-P(i) \neq P(j), y_{ij}$ OR $y_{kl} \notin \{Cys, Cys\}$ " and insert -- $y_{ij}+y_{kl} \leq 1 \, \forall P(k)-P(i) \neq P(l) - P(j), y_{ij}$ OR $Y_{kl} \notin \{Cys, Cys\}$ --.

Column 5,
Line 19, delete " $\min_{\varphi} \quad E_{ECEPP}/3$ " and insert -- $\min_{\varphi} \quad ' \quad E_{ECEPP}/3$ --.

Line 25, delete "i=1,. . .,$N_{100}$" and insert -- i=1,...,$N_{\phi}$ --.
Line 26, after "$\phi_i^L$ and $\phi_i^U$" insert -- representing lower --.

Column 7,
Line 1, delete " $\Delta G_j^{rxfn \, field}(PS_i^o/S_1^o),$ " and insert -- $\Delta G_j^{rxn \, field}(PS_i^o/S_i^o),$ --.

Line 10, delete "(FIG. 1B)" and insert -- (FIG. 11B) --.

Column 9,
Line 49, after "cases" insert -- , --.

Column 10,
Line 25, delete "Bank." and insert -- Bank). --.

Column 13,
Line 25, after "then" insert -- be --.

Column 14,
Lines 62-63, delete " $Z=\exp^{-[(E-TS)/kBT)]}=\exp^{-[E/(kBT)] \, \exp[S/(kB)]}$ " and insert -- $Z =\exp^{-[(E-TS)/kBT)]}=\exp^{-[E/(kBT)]} \exp^{[S/(kB)]}$ --.

Column 15,
Line 6, delete "E($\theta_7$)," and insert -- E($\theta_\gamma$), --.
Line 8, delete "$N_{74}$" and insert -- $N_\theta$ --.

Line 32, delete " $S_\gamma^{har} \propto -k_B \, \ln[Det \, (H(\theta_\gamma))]$ " and insert -- $S_\gamma^{har} \propto -k_B \ln[Det \, (H(\theta\gamma))]$ --.

UNITED STATES PATENT AND TRADEMARK OFFICE
CERTIFICATE OF CORRECTION

PATENT NO.    : 6,832,162 B2
DATED         : December 14, 2004
INVENTOR(S)   : Christodoulos A. Floudas et al.

It is certified that error appears in the above-identified patent and that said Letters Patent is hereby corrected as shown below:

Column 17,
Line 3, delete "268:11144-1149," and insert -- 268:1144-1149, --.

Line 42, delete " $F_{total}=F_{vac}^{har}+F_{cavity}+F_{solv}+F_{ionize}$ " and insert -- $F_{vac}^{har} + F_{cavity} + F_{solv} + F_{ionize}$ --.

Column 18,
Line 27, delete "$F_{ionize}(pH)=kT \ln Z$" and insert -- $F_{ionize}(pH) = kT \ln Z$ --.

Column 19,
Line 26, delete "$\Delta G^{irxn\ field}$" and insert -- $\Delta G_j^{rxn\ field}$ --.
Line 26, delete "Poisson-Bo" and insert -- Poisson-Boltzmann --.
Line 47, delete "$(PS_i^o/S_i^+)$" and insert -- $(PS_i^o/S_i^o)$ --.
Line 60, delete "$\Delta\Delta G_j^{perm\ dipole}=\Delta G_j^{perm\ dipole}(PS_j/S_i^+)-\Delta G_j^{perm\ dipole}(PS_o^+S^{o+})$" and insert
-- $\Delta\Delta G_j^{perm\ dipole}=\Delta G_j^{perm\ dipole}(PS_i^+/S_i^+)-\Delta G_j^{perm\ dipole}(PS_i^{o+}S_i^o)$ --.
Line 65, delete "$\Delta\Delta G^{jperm\ dipole}$" and insert -- $\Delta\Delta G_j^{perm\ dipole}$ --.

Column 20,
Line 26, delete "$\Delta G_{jk}=\Delta G_{jk}(PS_i^{j+,k+})+\Delta G_{jk}(PS_i^{jo,ko})-\Delta G_{jk}(PS_i^{j+,ko})-\Delta G_{jk}(Ps_i^{jo,k+})(26)$"
and insert -- $\Delta Gj_k = \Delta G_{jk}(PS_i^{j+,k+}) + \Delta G_{jk}(PS_i^{jo,ko})-\Delta G_{jk}(PS_i^{j+,ko})-\Delta G_{jk}(Ps_i^{jo,k+})\ (26)$ --.

Column 23,
Lines 15-16, delete "conditions" and insert -- conditions: --.

Column 24,
Line 63, delete " $y_{ij}+y_{kl} \leq 1\ \forall P(i)+P(j) \neq P(k)+P(l),\ y_{ij}\ OR\ y_{kl} \notin \{Cys, Cys\}$ " and insert -- $y_{ij}+y_{kl}\leq 1\ \forall P(i)+P(j)\neq P(k)+P(l),\ y_{ij}\ OR\ y_{kl}\notin \{Cys, Cys\}$ --.

Column 25,
Line 8, delete " $y_{ij}+y_{kl} \leq 1\ \forall P(k)-P(i) \neq P(l)-P(j),\ y_{ij}\ OR\ y_{kl} \notin \{Cys, Cys\}$ " and insert -- $y_{ij}+y_{kl}\leq 1\ \forall P(k)-P(i)\neq P(l)-P(j),\ y_{ij}\ OR\ y_{kl}\notin \{Cys, Cys\}$ --.

Lines 40-44, delete " $\sum_{i\in\{Cys\}}\sum_{j\in\{Cys\},P(i)+7<P(j)} y_{ij} \leq N_{SS}$ " and insert -- $\sum_{i\in\{Cys\}}\sum_{j\in\{Cys\},P(i)+7<P(j)} y_{ij} \leq N_{SS}$ --.

Column 26,
Line 56, delete "$w_{si,sj}\leqq DS_{si,sj}$" and insert -- $w_{si,sj}\leq DS_{si,sj}$ --.

UNITED STATES PATENT AND TRADEMARK OFFICE
CERTIFICATE OF CORRECTION

PATENT NO. : 6,832,162 B2
DATED : December 14, 2004
INVENTOR(S) : Christodoulos A. Floudas et al.

It is certified that error appears in the above-identified patent and that said Letters Patent is hereby corrected as shown below:

Column 27,
Line 33, delete " $y_{ij} \leq w_{si,sj}\ \forall\ P^{beg}(si)\ y_{ij} \leq N_{ss} \leq P(i) \leq P^{end}(si), P^{beg}(sj) \leq P(j) \leq P^{end}(sj)$ "

and insert -- $y_{ij} \leq w_{si,sj}\ \forall\ P^{beg}(si) \leq P(i) \leq P^{end}(si)\,,\ P^{beg}(sj) \leq P(j) \leq P^{end}(sj)$ --.

Column 34,
Line 26, delete "(D)AEs)." and insert -- (DAEs). --.

Line 40, delete "θ:" and insert -- $\ddot{\theta}$ : --.

Line 43, delete " $M(\theta)\theta + C(\theta, \dot{\theta}) = 0$ " and insert -- $M(\theta)\ddot{\theta} + C(\theta, \dot{\theta}) = 0$ --.

Line 47, delete "and θ" and insert -- and $\ddot{\theta}$ --.

Line 61, delete "calculate θ" and insert -- calculate $\ddot{\theta}$ --.

Column 35,
Line 58, delete "$Z_k$" and insert -- $z_k$ --.

Line 62, delete " $G_k = P_k H_k^T D_l^{-1}$ " and insert -- $G_k = P_k H_k^T D_k^{-1}$ --.

Column 36,
Line 4, delete " $P_{k-1} \leftarrow P_{k-1} + \phi_k(P_k - G_k H_k^T P_k)\phi_k^T$ " and insert -- $P_{k-1} \leftarrow P_{k-1} + \varphi_k(P_k - G_k H_k^T P_k)\varphi_k^T$ --.

Line 6, delete " $z_{k-1} \leftarrow z_{k-1}\phi_k(z_k + P_k a_k + G_k \varepsilon_k)$ " and insert -- $z_{k-1} \leftarrow z_{k-1} + \varphi_k(z_k + P_k a_k + G_k \varepsilon_k)$ --.

Line 12, delete " $\alpha_k = \phi_k^T \alpha_{k-1}$ " and insert -- $\alpha_k = \varphi_k^T \alpha_{k-1}$ --.

Line 14, delete " $\theta_k = \varepsilon_k D_k^{-1} - G_k \alpha_k$ " and insert -- $\ddot{\theta}_k = \varepsilon_k D_k^{-1} - G_k \alpha_k$ --.

Line 18, delete " $\alpha_k \leftarrow \alpha_k + H_k \theta_k + a_k$ " and insert -- $\alpha_k \leftarrow \alpha_k + H_k \ddot{\theta}_k + a_k$ --.

Line 52, delete "θ," and insert -- $\ddot{\theta}$, --.

Column 39,
Lines 36 and 55, delete "a helix" and insert -- α helix --.

Column 48,
Line 38, delete "a helical" and insert -- α helical --.

UNITED STATES PATENT AND TRADEMARK OFFICE
CERTIFICATE OF CORRECTION

PATENT NO. : 6,832,162 B2
DATED : December 14, 2004
INVENTOR(S) : Christodoulos A. Floudas et al.

It is certified that error appears in the above-identified patent and that said Letters Patent is hereby corrected as shown below:

Column 49,
Line 50, delete "Iterated=13 BLAST)." and insert -- Iterated=13-BLAST). --.

Column 51,
Line 43, delete "systems.A For" and insert -- systems. For --.
Column 52, Line 24, delete "3 strands," and insert -- β strands, --.

Column 55,
Line 52, delete "Comette et al.," and insert -- Cornette et al., --.

Column 62,
Line 67, delete "[Compstatin]" and insert -- [$\overline{C}$ompstatin] --.

Column 63,
Line 59, delete "mo/Å" and insert -- mol/Å --.

Column 64,
Line 16, delete ",β-turn" and insert -- β-turn --.

Column 66,
Line 21, delete "Φ," and insert -- φ, --.

Column 115,
Line 44, delete "segments." and insert -- segments, and --.

Signed and Sealed this

Thirty-first Day of January, 2006

JON W. DUDAS
*Director of the United States Patent and Trademark Office*

**Initial Conformer
Free energy based
on vacuum potential**

$$F_{cavity} = \gamma(SA) + b$$
$$F_{solv} = F_{polar}(\varepsilon=80)$$
$$\quad - F_{polar}(\varepsilon=1)$$

$$F_{ionize}(pH) = kT \ln(Z)$$